US012636304B2

(12) United States Patent (10) Patent No.: US 12,636,304 B2
Rice et al. (45) Date of Patent: May 26, 2026

(54) METABOLICALLY STABILIZED DOUBLE STRANDED mRNA

(71) Applicant: University of Iowa Research Foundation, Iowa City, IA (US)

(72) Inventors: Kevin G. Rice, Iowa City, IA (US); Samuel T. Crowley, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 235 days.

(21) Appl. No.: 17/235,535

(22) Filed: Apr. 20, 2021

(65) Prior Publication Data

US 2021/0236533 A1 Aug. 5, 2021

Related U.S. Application Data

(62) Division of application No. 16/090,468, filed as application No. PCT/US2017/025527 on Mar. 31, 2017, now Pat. No. 11,007,213.

(60) Provisional application No. 62/317,142, filed on Apr. 1, 2016, provisional application No. 62/335,186, filed on Apr. 1, 2016.

(51) Int. Cl.
| | |
|---|---|
| *A61K 31/713* | (2006.01) |
| *A61K 39/00* | (2006.01) |
| *A61K 39/12* | (2006.01) |
| *C07H 21/02* | (2006.01) |
| *C12N 15/67* | (2006.01) |

(52) U.S. Cl.
CPC .... *A61K 31/713* (2013.01); *A61K 39/001191* (2018.08); *A61K 39/12* (2013.01); *C07H 21/02* (2013.01); *C12N 15/67* (2013.01); *A61K 2039/53* (2013.01)

(58) Field of Classification Search
None
See application file for complete search history.

(56) References Cited

U.S. PATENT DOCUMENTS

| | | | |
|---|---|---|---|
| 9,868,692 | B2 | 1/2018 | Benenato |
| 10,064,959 | B2 | 9/2018 | Schrum et al. |
| 10,266,485 | B2 | 4/2019 | Benenato |
| 10,442,756 | B2 | 10/2019 | Benenato et al. |
| 10,577,403 | B2 | 3/2020 | De Fougerolles et al. |
| 10,702,600 | B1 | 7/2020 | Ciaramella et al. |
| 10,703,789 | B2 | 7/2020 | De Fougerolles et al. |
| 11,007,213 | B2 | 5/2021 | Rice et al. |
| 2014/0328825 | A1 | 11/2014 | Meis et al. |
| 2014/0371302 | A1 | 12/2014 | Afeyan et al. |
| 2019/0111070 | A1 | 4/2019 | Rice et al. |
| 2022/0296632 | A1 | 9/2022 | Uchida et al. |
| 2024/0350621 | A1 | 10/2024 | Rice |

FOREIGN PATENT DOCUMENTS

| | | | | |
|---|---|---|---|---|
| WO | WO-2007024708 A2 | 3/2007 | | |
| WO | WO-2013016297 A2 * | 1/2013 | .............. | A61P 37/06 |
| WO | WO-2013185067 A1 | 12/2013 | | |
| WO | WO-2017173354 A2 | 10/2017 | | |
| WO | WO-2017173354 A3 | 10/2017 | | |
| WO | WO-2023014974 A1 | 2/2023 | | |

OTHER PUBLICATIONS

Kotterman et al., 2014 (Nature Reviews, vol. 15, p. 445-451).*
Shim et al., 2017 (Current Gene Therapy, vol. 17, No. 5, p. 1-18).*
Lenzi et al., 2014 (NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16).*
Kotterman et al., 2014 (Nature Reviews, vol. 15, p. 445-451) (Year: 2014).*
Lenzi et al., 2014 (NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16) (Year: 2014).*
Shim et al., 2017 (Current Gene Therapy, vol. 17, No. 5, p. 1-18) (Year: 2017).*
Burgess et al. Nature Reviews Genetics 13.11 (2012): 757-757. (Year: 2012).*
"U.S. Appl. No. 16/090,468, 312 Amendment filed Feb. 2, 2021", 3 pgs.
"U.S. Appl. No. 16/090,468, 312 Amendment filed Feb. 9, 2021", 3 pgs.
"U.S. Appl. No. 16/090,468, Examiner Interview Summary mailed Feb. 3, 2021", 3 pgs.
"U.S. Appl. No. 16/090,468, Non Final Office Action mailed Jun. 9, 2020", 17 pgs.
"U.S. Appl. No. 16/090,468, Notice of Allowance mailed Jan. 13, 2021", 10 pgs.
"U.S. Appl. No. 16/090,468, Preliminary Amendment filed Oct. 1, 2018", 7 pgs.
"U.S. Appl. No. 16/090,468, Response filed May 1, 2020 to Restriction Requirement mailed Feb. 13, 2020", 7 pgs.
"U.S. Appl. No. 16/090,468, Response filed Nov. 2, 2020 to Non Final Office Action mailed Jun. 9, 2020", 9 pgs.
"U.S. Appl. No. 16/090,468, Restriction Requirement mailed Feb. 13, 2020", 8 pgs.
"International Application Serial No. PCT/US2017/025527, International Preliminary Report on Patentability mailed Oct. 11, 2018", 9 pgs.
"International Application Serial No. PCT/US2017/025527, International Search Report mailed Jan. 11, 2018", 7 pgs.

(Continued)

*Primary Examiner* — Maria Marvich
*Assistant Examiner* — Brendan Thomas Tinsley
(74) *Attorney, Agent, or Firm* — Schwegman Lundberg & Woessner, P.A.

(57) ABSTRACT

Double stranded mRNA, e.g., produced in vitro, as well as method of making and using the ds mRNA, are provided. For example, the disclosure provides a method of expressing a prophylactic or therapeutic protein in mammalian cells in vivo, that includes introducing a composition comprising ds mRNA that encodes a protein to the mammalian cells in an amount effective to express the protein in vivo.

16 Claims, 10 Drawing Sheets

Specification includes a Sequence Listing.

(56) References Cited

OTHER PUBLICATIONS

"International Application Serial No. PCT/US2017/025527, Written Opinion mailed Jan. 11, 2018", 7 pgs.

Anneke, Brummer, et al., "MicroRNA binding sites in the coding region of mRNAs Extending the repertoire of post-transcriptional gene regulation Problems & Paradigm", Bioessays, vol. 36 No. 6, (Jun. 1, 2014), 617-626.

Bin, Li, et al., "Effects of Chemically Modified Messenger RNA on Protein Expression", Bioconjugate Chemistry, vol. 27 No. 3, (Mar. 16, 2016), 849-853.

Crowley, Samuel T., et al., "Efficient Expression of mRNA PEG-Peptide Polyplexes in Mouse Liver", (2015), 2 pgs.

Ginn, S. L., et al., "Gene therapy clinical trials worldwide to 2012—an update.", J Gene Med, 15(2), (2013), 65-77.

Kahn, Jeffrey S., et al., "Recombinant vesicular stomatitis virus expressing respiratory syncytial virus (RSV) glycoproteins: RSV fusion protein can mediate infection and cell fusion", Virology 254.1, (1999), 81-91.

Karpala, A J, et al., "Imune responses to dsRNA Implications for gene silencing technology", Immunology and Cell Bio, Carlton AU, vol. 83 No. 3, (Jun. 1, 2005), 211-216.

Liu, et al., "Structural Basis of Toll-Like Receptor 3 Signaling with Double-Stranded RNA" Science, vol. 320, (Apr. 18, 2008), 379-381.

M, Caskey, et al., "Synthetic double-stranded RNA induces innate ininune responses similar to a live viral vaccine in humans", The Journal of Immunology, vol. 181 No. 1, (Nov. 7, 2011), 276-2366.

Poliskey, Jacob, et al., "Development of Stabilized mRNA Nanoparticles for in Vivo Gene Delivery (Poster)", University of Iowa Center for Biocatalysisand Biotechnology., (2015), 1 pg.

Sahin, Ugur, et al., "mRNA-based therapeutics—developing a new class of drugs", Nature reviews Drug discovery 13.10, (2014), 759-780.

Takahashi, Kazutoshi, et al., "Induction of pluripotent stem cells from mouse embryonic and adult fibroblast cultures by defined factors", cell 126.4, (2006), 663-676.

Tatyana, O Kabilova, et al., "Imunotherapy of hepatocellular carcinoma with small double-stranded RNA", BMC Cancer Biomed Central London GB, vol. 14 No. 1, (May 18, 2014), 338.

Weide, Benjamin, et al., "Direct injection of protamine-protected mRNA: results of a phase 1/2 vaccination trial in metastatic melanoma patients", Journal of Immunotherapy 32.5, (2009), 498-507.

Zhou, Hongyan, et al., "Generation of induced pluripotent stem cells using recombinant proteins", Cell stem cell 4.5, (2009), 381.

"International Application Serial No. PCT/US2022/039577, International Search Report mailed Nov. 28, 2022", 6 pgs.

"International Application Serial No. PCT/US2022/039577, Written Opinion mailed Nov. 28, 2022", 9 pgs.

Anderson, Bart R., et al., "Incorporation of pseudouridine into mRNA enhances translation by diminishing PKR activation", Nucleic Acids Research, vol. 38, No. 17, (May 10, 2010), 5884-5892.

Bayat, Maryam, et al., "Essential considerations during vaccine design against COVID-19 and review of pioneering vaccine candidate platforms", International Immunopharmacology 97, 107679, (Apr. 2021), 1-15.

Chen, Nanhua, et al., "RNA Sensors of the Innate Immune System and Their Detection of Pathogens", IUBMB Life vol. 69, No. 5, (May 2017), 297-304.

Corbett, Kizzmekia, et al., "SARS-CoV-2 mRNA vaccine design enabled by prototype pathogen preparedness", Nature, Nature Publishing Group UK, London, vol. 586, No. 7830, (Aug. 5, 2020), 21 pgs.

Gebre, Makda S., et al., "Novel approaches for vaccine development", Cell 184, (Mar. 18, 2021), 1589-1603.

Karikó, Katalin, et al., "Incorporation of Pseudouridine Into mRNA Yields Superior Nonimmunogenic Vector with Increased Translational Capacity and Biological Stability", Molecular Therapy vol. 16 No. 11, (Nov. 2008), 1833-1840.

Karikó, Katalin, et al., "Suppression of RNA Recognition by Toll-like Receptors: The Impact of Nucleoside Modification and the Evolutionary Origin of RNA", Immunity, vol. 23, (Aug. 2005), 165-175.

Kato, Hiroki, et al., "Length-dependent recognition of double-stranded ribonucleic acids by retinoic acid-inducible gene-I and melanoma differentiation-associated gene 5", J. Exp. Med. vol. 205 No. 7, (2008), 1601-1610.

Linares-Fernandez, Sergio, et al., "Tailoring mRNA Vaccine to Balance Innate/Adaptive Immune Response", Trends in Molecular Medicine, vol. 26, No. 3, (Mar. 2020), 311-323.

Mu, Xin, et al., "An origin of the immunogenicity of in vitro transcribed RNA", Nucleic Acids Research vol. 46, No. 10, (Mar. 9, 2018), 5239-5249.

Muramatsu, Hiromi, et al., "Lyophilization provides long-term stability for a lipid nanoparticle-formulated, nucleoside-modified mRNA vaccine", Molecular Therapy, vol. 30 No. 5, (May 2022), 1-11.

Park, Jung Woo, et al., "mRNA vaccines for COVID-19: what, why and how", International Journal of Biological Sciences, vol. 17, (2021), 1446-1460.

Pollard, Charlotte, et al., "Type I IFN Counteracts the Induction of Antigen-Specific Immune Responses by Lipid-Based Delivery of mRNA Vaccines", Molecular Therapy vol. 21 No. 1, (Jan. 2013), 251-259.

Rice, Kevin G., "Producing Better Gene-Based Messages Against Coronavirus", College of Pharmacy—The University of Iowa, Retrieved from Internet. URL: <https://pharmacy.uiowa.edu/news/2020/08/producing-better-gene-based-messages-against-coronavirus>, (Aug. 7, 2020), 5 pgs.

Teijaro, John R., et al., "COVID-19 vaccines: modes of immune activation and future challenges", Nature reviews. Immunology vol. 21,4, (Mar. 2021), 195-197.

Tockary, Theofilus A, et al., "Tethering designer short double-stranded RNA to mRNA for co-delivery ofmolecularly-targeted adjuvants and antigens towards cancer vaccination", bioRxiv, preprint, [Online] Retrieved from the internet: <https://www.biorxiv.org/content/10.1101/2022.01.18.476829v1.full.pdf>, (Jan. 21, 2022), 1-25.

Uchida, Satoshi, et al., "Designing immunostimulatory double stranded messenger RNA with maintained transnational activity through hybridization with poly A sequences for effective vaccination", Biomaterials, vol. 150, Amsterdam, NL, (Jan. 1, 2018), 17 pgs.

Ueyama, Hiroyuki, et al., "DNA binding behavior of peptides carrying acridinyl units: First example of effective poly-intercalation", Nucleic Acids Research Supplement No. 1, (Feb. 2001), 163-164.

Ueyama, Hiroyuki, et al., "Novel synthesis of a tetra-acridinyl peptide as a new DNA polyintercalator", Nucleic Acids Symposium Series No. 44, (2000), 133-134.

Verbeke, Rein, et al., "The dawn of mRNA vaccines: The COVID-19 case", Journal of Controlled Release 333, (Mar. 2021), 511-520.

Vogel, Annette B, et al., "BNT162b vaccines protect rhesus macaques from SARS-CoV-2", Nature, vol. 592, No. 7853, (Feb. 1, 2021), 35 pgs.

Wesselhoeft, R. Alexander, et al., "Engineering circular RNA for potent and stable translation in eukaryotic cells", Nat Commun. 9(1):2629, (Jul. 6, 2018), 1-10.

Wesselhoeft, R. Alexander, et al., "RNA Circularization Diminishes Immunogenicity and Can Extend Translation Duration In Vivo", Molecular Cell 74, (May 2019), 508-520.

Beck, Jan D., et al., "mRNA therapeutics in cancer immunotherapy", Molecular Cancer (2021) 20:69, 24 pgs.

Crooke, Stanley T., et al., "Antisense technology: an overview and prospectus", Nature Reviews Drug Discovery 20(6), (Jun. 2021), 427-453.

Feng, Rundong, et al., "RNA Therapeutics—Research and Clinical Advancements", Frontiers in Molecular Biosciences, vol. 8, Article 710738, (Sep. 2021).

Gao, Minsong, "Synthetic modified messenger RNA for therapeutic applications", Acta Biomaterialia 131 (2021), 15 pgs.

(56)         References Cited

OTHER PUBLICATIONS

Hou, Xucheng, et al., "Lipid nanoparticles for mRNA delivery", Nature Review Materials, vol. 6, (Dec. 2021), 1078-1094.

Migliorati, Julia M., et al., "Absorption, Distribution, Metabolism, and Excretion of US Food and Drug Administration—Approved Antisense Oligonucleotide Drugs", Drug Metabolism & Disposition 50, (Jun. 2022), 888-897.

"International Application Serial No. PCT/US2022/039577, International Preliminary Report on Patentability mailed Feb. 15, 2024", 11 pgs.

Pardi, Norbert, et al., "Expression kinetics of nucleoside-modified mRNA delivered in lipid nanoparticles to mice by various routes", Journal of Controlled Release 217, (Aug. 2015), 345-351.

Awasthi, S., "Nucleoside-modified mRNA encoding HSV-2 glycoproteins C, D, and E prevents clinical and subclinical genital herpes", Science Immunology, vol. 4, Issue 39, Sep. 13, 2019.

Bahl, Kapil, "Preclinical and Clinical Demonstration of Immunogenicity by mRNA Vaccines against H10N8 and H7N9 Influenza Viruses", Molecular Therapy, vol. 25, Issue 6, Jun. 7, 2017, 1316-1327.

Baumhover, Nicholas J., "Synthesis and in vitro testing of new potent polyacridine-melittin gene delivery peptides", Bioconjugate Chem. 2010, 21, 1, 74-83, 2010, 25 pgs.

Chantal, Pichon, "Mannosylated and Histidylated LPR Technology for Vaccination with Tumor Antigen mRNA", https link.springer.com content pdf 10.1007%2F978-1-62703-260-5_16.pdf, 2013, 247-274.

Corey, Lawrence, "A strategic approach to COVID-19 vaccine RandD", Science, vol. 368, Issue 6494, May 11, 2020, 948-950.

Crowley, S T, "Efficient expression of stabilized mRNA PEG-peptide polyplexes in liver", Gene Therapy vol. 22, Jun. 30, 2015, 993-999.

Diken, M., "Selective uptake of naked vaccine RNA by dendritic cells is driven by macropinocytosis and abrogated upon DC maturation", Gene Therapy vol. 18, Mar. 3, 2011, 702-708.

Fernandez, C A, "Metabolically stabilized long-circulating PEGylated polyacridine peptide polyplexes mediate hydrodynamically stimulated gene expression in liver", Gene Therapy vol. 18, 2011, 23-37.

Gomez-Aguado, I., "Nanomedicines to Deliver mRNA State of the Art and Future Perspectives", Nanomaterials, 102, 2020, 42 pgs.

Hassett, Kimberly J., "Optimization of Lipid Nanoparticles for Intramuscular Administration of mRNA Vaccines", Molecular Therapy Nucleic Acids, Apr. 15, 2019, 1-11.

Jagger, Brett W., "Protective Efficacy of Nucleic Acid Vaccines Against Transmission of Zika Virus During Pregnancy in Mice", The Journal of Infectious Diseases, vol. 220, Issue 10, Nov. 15, 2019, 1577-1588.

John, Shinu, "Multi-antigenic human cytomegalovirus mRNA vaccines that elicit potent humoral and cell-mediated immunity", Vaccine, vol. 36, Issue 12, Mar. 14, 2018, 1689-1699.

Khargharia, Sanjib, "PEG length and chemical linkage controls polyacridine peptide DNA polyplex pharmacokinetics, biodistribution, metabolic stability and in vivo gene expression", Journal of Controlled Release, vol. 170, Issue 3, pp. 325-333, Sep. 28, 2013, 18 pgs.

Kizzire, K, "High-affinity PEGylated polyacridine peptide polyplexes mediate potent in vivo gene expression", Gene Therapy vol. 20, pp. 407-416, 2013, 23 pgs.

Le Moignic, A., "Preclinical evaluation of mRNA trimannosylated lipopolyplexes as therapeutic cancer vaccines targeting dendritic cells", Journal of Controlled Release, vol. 278, May 28, 2018, 110-121.

Lutz, Johannes, "Unmodified mRNA in LNPs constitutes a competitive technology for prophylactic vaccines", npj Vaccines vol. 2, Article No. 29, 2017, 9 pgs.

Meyer, Michelle, "Modified mRNA-Based Vaccines Elicit Robust Immune Responses and Protect Guinea Pigs From Ebola Virus Disease", The Journal of Infectious Diseases, vol. 217, Issue 3, Feb. 1, 2018, 451-455.

Pardi, N., "mRNA vaccines—a new era in vaccinology", Nature Reviews | Drug Discovery, Apr. 2018, 19 pgs.

Pardi, Norbert, "Recent advances in mRNA vaccine technology", Current Opinion in Immunology, Aug. 2020, 14-20.

Pardi, Norbert, "Nucleoside-modified mRNA vaccines induce potent T follicular helper and germinal center B cell responses", J Exp Med 2018 215 6, May 8, 2018, 1571-1588.

Pardi, Norbert, "Zika virus protection by a single low-dose nucleoside-modified mRNA vaccination", Nature vol. 543, Feb. 2, 2017, 248-251.

Pardi, Norbert, "Nucleoside-modified mRNA immunization elicits influenza virus hemagglutinin stalk-specific antibodies", Nature Communications vol. 9, Article No. 3361, Aug. 22, 2018, 12 pgs.

Perche, Federico, "Selective gene delivery in dendritic cells with mannosylated and histidylated lipopolyplexes", Journal of Drug Targeting, vol. 19, 2011, 315-325.

Perche, Federico, "Enhancement of dendritic cells transfection in vivo and of vaccination against B16F10 melanoma with mannosylated histidylated lipopolyplexes loaded with tumor antigen messenger RNA", Nanomedicine Nanotechnology, Biology and Medicine, vol. 7, Issue 4, Aug. 2011, 445-453.

Poliskey, Jacob A., "Metabolically stabilized double-stranded mRNA polyplexes", Gene Therapy vol. 25, Aug. 28, 2018, 473-484.

Richner, Justin M., "Modified mRNA Vaccines Protect against Zika Virus Infection", Mar. 9, 2017, 25 pgs.

Richner, Justin M., "Vaccine Mediated Protection Against Zika Virus-Induced Congenital Disease", Cell, vol. 170, Issue 2p273-283.e12, Jul. 13, 2017, 24 pgs.

Roth, Claude, "A Modified mRNA Vaccine Targeting Immunodominant NS Epitopes Protects Against Dengue Virus Infection in HLA Class I Transgenic Mice", Front. Immunol, vol. 10, Jun. 21, 2019, 14 pgs.

Selmi, Abderraouf, "Uptake of synthetic naked RNA by skin-resident dendritic cells via macropinocytosis allows antigen expression and induction of T-cell responses in mice", Cancer Immunology, Immunotherapy, vol. 65, Jul. 15, 2016, 1075-1083.

Semple, Sean C., "Rational design of cationic lipids for siRNA delivery", Nature Biotechnology, vol. 28, Jan. 17, 2010, 172-176.

Uchida, Satoshi, "Designing immunostimulatory double stranded messenger RNA with maintained translational activity through hybridization with poly A sequences for effective vaccination", Biomaterials, vol. 150, Jan. 2018, 162-170.

Vanblargan, Laura A., "An mRNA Vaccine Protects Mice against Multiple Tick-Transmitted Flavivirus Infections", Cell Reports, vol. 25, Issue 12, Dec. 18, 2018, 3382-3392.

Wu, Fan, "A new coronavirus associated with human respiratory disease in China", Nature. 12, vol. 579, e-pub Feb. 3, 2020, Mar. 2020, 265-269.

Zhang, J., "Progress and Prospects on Vaccine Development against SARS-CoV-2", Vaccines 2020, 12 pgs.

* cited by examiner

```
                        SEQUENCE LISTING

<160> NUMBER OF SEQ ID NOS: 15

<210> SEQ ID NO 1
<211> LENGTH: 1524
<212> TYPE: DNA
<213> ORGANISM: Artificial Sequence
<220> FEATURE:
<223> OTHER INFORMATION: A synthetic nucleic acid sequence

<400> SEQUENCE: 1
agcagacaga ggactctcat taaggaaggt gtcctgtgcc ctgaccctac aagatgccaa      60
gagaagatgc tcacttcatc tatggttacc ccaagaaggg gcacggccac tcttacacca     120
cggctgaaga ggccgctggg atcggcatcc tgacagtgat cctgggagtc ttactgctca     180
tcggctgttg gtattgtaga agacgaaatg gatacagagc cttgatggat aaaagtcttc     240
atgttggcac tcaatgtgcc ttaacaagaa gatgcccaca agaagggttt gatcatcggg     300
acagcaaagt gtctcttcaa gagaaaaact gtgaacctgt ggttcccaat gctccacctg     360
cttatgagaa actctctgca gaacagtcac caccaccttta ttcaccttaa gagccagcga     420
gacacctgag acatgctgaa attatttctc tcacactttt gcttgaattt aatacagaca     480
tctaatgttc tcctttggaa tggtgtagga aaaatgcaag ccatctctaa taataagtca     540
gtgttaaaat tttagtaggt ccgctagcag tactaatcat gtgaggaaat gatgagaaat     600
attaaattgg gaaaactcca tcaataaatg ttgcaatgca tgatactatc tgtgccagag     660
gtaatgttag taaatccatg gtgttatttt ctgagagaca gaattcaagt gggtattctg     720
gggccatcca atttctcttt acttgaaatt tggctaataa caaactagtc aggttttcga     780
accttgaccg acatgaactg tacacagaat tgttccagta ctatggagtg ctcacaaagg     840
```

-continued

```
atactttttac aggttaagac aaagggttga ctggcctatt tatctgatca agaacatgtc      900
agcaatgtct ctttgtgctc taaaattcta ttatactaca ataatatatt gtaaagatcc      960
tatagctctt tttttttgag atggagtttc gctttgttg cccaggctgg agtgcaatgg      1020
cgcgatcttg gctcaccata acctccgcct cccaggttca agcaattctc ctgccttagc      1080
ctcctgagta gctgggatta caggcgtgcg ccactatgcc tgactaattt tgtagtttta      1140
gtagagacgg ggtttctcca tgttggtcag gctggtctca aactcctgac ctcaggtgat      1200
ctgcccgcct cagcctccca aagtgctgga attacaggcg tgagccacca cgcctggctg      1260
gatcctatat cttaggtaag acatataacg cagtctaatt acatttcact tcaaggctca      1320
atgctattct aactaatgac aagtattttc tactaaacca gaaattggta gaaggattta      1380
aataagtaaa agctactatg tactgcctta gtgctgatgc ctgtgtactg ccttaaatgt      1440
acctatggca atttagctct cttgggttcc caaatccctc tcacaagaat gtgcagaaga      1500
aatcataaag gatcagagat tctg                                            1524

<210> SEQ ID NO 2
<211> LENGTH: 2384
<212> TYPE: DNA
<213> ORGANISM: Artificial Sequence
<220> FEATURE:
<223> OTHER INFORMATION: A synthetic nucleic acid sequence

<400> SEQUENCE: 2
tattgagttc ttcaaacatt gtagcctctt tatggtctct gagaaataac taccttaaac       60
ccataatctt taatacttcc taaactttct taataagaga agctctattc ctgacactac      120
ctctcatttg caaggtcaaa tcatcattag ttttgtagtc tattaactgg gtttgcttag      180
gtcaggcatt attattacta accttattgt taatattcta accataagaa ttaaactatt      240
aatggtgaat agagtttttc actttaacat aggcctatcc cactggtggg atacgagcca      300
attcgaaaga aaagtcagtc atgtgctttt cagaggatga aagcttaaga taaagactaa      360
aagtgtttga tgctggaggt gggagtggta ttatataggt ctcagccaag acatgtgata      420
atcactgtag tagtagctgg aaagagaaat ctgtgactcc aattagccag ttcctgcaga      480
ccttgtgagg actagaggaa gaatgctcct ggctgttttg tactgcctgc tgtggagttt      540
ccagacctcc gctggccatt tccctagagc ctgtgtctcc tctaagaacc tgatggagaa      600
ggaatgctgt ccaccgtgga gcggggacag gagtccctgt ggccagcttt caggcagagg      660
ttcctgtcag aatatccttc tgtccaatgc accacttggg cctcaatttc ccttcacagg      720
ggtggatgac cgggagtcgt ggccttccgt cttttataat aggacctgcc agtgctctgg      780
caacttcatg ggattcaact gtggaaactg caagtttggc ttttggggac caaactgcac      840
agagagacga ctcttggtga gaagaaacat cttcgatttg agtgccccag agaaggacaa      900 atttttttgcc tacctcactt tagcaaagca taccatcagc tcagactatg tcatccccat      960
agggacctat ggccaaatga aaaatggatc aacacccatg tttaacgaca tcaatattta      1020
tgacctcttt gtctggatgc attattatgt gtcaatggat gcactgcttg ggggatctga      1080
aatctggaga gacattgatt ttgcccatga agcaccagct tttctgcctt ggcatagact      1140
cttcttgttg cggtgggaac aagaaatcca gaagctgaca ggagatgaaa acttcactat      1200
tccatattgg gactggcggg atgcagaaaa gtgtgacatt tgcacagatg agtacatggg      1260
aggtcagcac cccacaaatc ctaacttact cagcccagca tcattcttct cctcttggca      1320
```

```
gattgtctgt agccgattgg aggagtacaa cagccatcag tctttatgca atggaacgcc    1380
cgagggacct ttacggcgta atcctggaaa ccatgacaaa tccagaaccc caaggctccc    1440
ctcttcagct gatgtagaat tttgcctgag tttgacccaa tatgaatctg gttccatgga    1500
taaagctgcc aatttcagct ttagaaatac actggaagga tttgctagtc cacttactgg    1560
gatagcggat gcctctcaaa gcagcatgca caatgccttg cacatctata tgaatggaac    1620
aatgtcccag gtacagggat ctgccaacga tcctatcttc cttcttcacc atgcatttgt    1680
tgacagtatt tttgagcagt ggctccgaag gcaccgtcct cttcaagaag tttatccaga    1740
agccaatgca cccattggac ataaccggga atcctacatg gttcctttta taccactgta    1800
cagaaatggt gatttcttta tttcatccaa agatctgggc tatgactata gctatctaca    1860
agattcagac ccagactctt ttcaagacta cattaagtcc tatttggaac aagcgagtcg    1920
gatctggtca tggctccttg gggcggcgat ggtaggggcc gtcctcactg ccctgctggc    1980
agggcttgtg agcttgctgt gtcgtcacaa gagaaagcag cttcctgaag aaaagcagcc    2040
actcctcatg gagaaagagg attaccacag cttgtatcag agccatttat aaaaggctta    2100
ggcaatagag tagggccaaa aagcctgacc tcactctaac tcaaagtaat gtccaggttc    2160
ccagagaata tctgctggta tttttctgta aagaccattt gcaaaattgt aacctaatac    2220
aaagtgtagc cttcttccaa ctcaggtaga acacacctgt ctttgtcttg ctgttttcac    2280
tcagcccttt taacattttc ccctaagccc atatgtctaa ggaaaggatg ctatttggta    2340
atgaggaact gttatttgta tgtgaattaa agtgctctta tttt                     2384
```

```
<210> SEQ ID NO 3
<211> LENGTH: 1580
<212> TYPE: DNA
<213> ORGANISM: Artificial Sequence
<220> FEATURE:
<223> OTHER INFORMATION: A synthetic nucleic acid sequence

<400> SEQUENCE: 3
cccacactcc cgcctgttgc cctgaccaga gtcatcatgc ctcttgagca gaggagtcag      60
cactgcaagc ctgaagaagg ccttgaggcc cgaggagagg ccctgggcct ggtgggtgcg     120
caggctcctg ctactgagga gcaggaggct gcctcctcct cttctactct agttgaagtc     180
accctggggg aggtgcctgc tgccgagtca ccagatcctc cccagagtcc tcagggagcc     240
tccagcctcc ccactaccat gaactaccct ctctggagcc aatcctatga ggactccagc     300
aaccaagaag aggaggggcc aagcaccttc cctgacctgg agtccgagtt ccaagcagca     360
ctcagtagga aggtggccga gttggttcat tttctgctcc tcaagtatcg agccagggag     420
ccggtcacaa aggcagaaat gctggggagt gtcgtcggaa attggcagta tttctttcct     480
gtgatcttca gcaaagcttt cagttccttg cagctggtct ttggcatcga gctgatggaa     540
gtggacccca tcggccactt gtacatcttt gccacctgcc tgggcctctc ctacgatggc     600
ctgctgggtg acaatcagat catgcccaag gcaggcctcc tgataatcgt cctggccata     660
atcgcaagag agggcgactg tgcccctgag gagaaaatct gggaggagct gagtgtgtta     720
gaggtgtttg aggggaggga agacagtatc ttggggggatc ccaagaagct gctcacccaa     780
catttcgtgc aggaaaacta cctggagtac cggcaggtcc ccggcagtga tcctgcatgt     840
tatgaattcc tgtggggtcc aagggccctc gttgaaacca gctatgtgaa agtcctgcac     900
catatggtaa agatcagtgg aggacctcac atttcctacc cacccctgca tgagtgggtt     960
ttgagagagg gggaagagtg agtctgagca cgagttgcag ccagggccag tgggaggggg    1020
```

-continued

```
tctgggccag tgcaccttcc ggggccgcat cccttagttt ccactgcctc ctgtgacgtg      1080
aggcccattc ttcactcttt gaagcgagca gtcagcattc ttagtagtgg gtttctgttc      1140
tgttggatga ctttgagatt attctttgtt tcctgttgga gttgttcaaa tgttcctttt      1200
aacggatggt tgaatgagcg tcagcatcca ggtttatgaa tgacagtagt cacacatagt      1260
gctgtttata tagtttagga gtaagggtct tgttttttac tcaaattggg aaatccattc      1320
cattttgtga attgtgacat aataatagca gtggtaaaag tatttgctta aaattgtgag      1380
cgaattagca ataacataca tgagataact caagaaatca aaagatagtt gattcttgcc      1440
ttgtacctca atctattctg taaaattaaa caaatatgca aaccaggatt tccttgactt      1500
ctttgagaat gcaagcgaaa ttaaatctga ataaataatt cttcctcttc aaaaaaaaaa      1560
aaaaaaaaaa aaaggccaca                                                  1580
```

```
<210> SEQ ID NO 4
<211> LENGTH: 1629
<212> TYPE: DNA
<213> ORGANISM: Artificial Sequence
<220> FEATURE:
<223> OTHER INFORMATION: A synthetic nucleic acid sequence

<400> SEQUENCE: 4
gttggcagag gtggcggcgg cggcatgggt gccccgacgt tgccccctgc ctggcagccc        60
tttctcaagg accaccgcat ctctacattc aagaactggc ccttcttgga gggctgcgcc       120
tgcaccccgg agcggatggc cgaggctggc ttcatccact gccccactga gaacgagcca       180
gacttggccc agtgtttctt ctgcttcaag gagctggaag ctgggagcc agatgacgac        240 cccatagagg aacataaaaa gcattcgtcc ggttgcgctt tcctttctgt caagaagcag       300
tttgaagaat taacccttgg tgaatttttg aaactggaca gagaaagagc caagaacaaa       360
attgcaaagg aaaccaacaa taagaagaaa gaatttgagg aaactgcgaa gaaagtgcgc       420
cgtgccatcg agcagctggc tgccatggat tgaggcctct ggccggagct gcctggtccc       480
agagtggctg caccacttcc agggtttatt ccctggtgcc accagccttc ctgtgggccc       540
cttagcaatg tcttaggaaa ggagatcaac attttcaaat tagatgtttc aactgtgctc       600
ttgttttgtc ttgaaagtgg caccagaggt gcttctgcct gtgcagcggg tgctgctggt       660
aacagtggct gcttctctct ctctctctct tttttggggg ctcatttttg ctgttttgat       720
tcccgggctt accaggtgag aagtgaggga ggaagaaggc agtgtccctt ttgctagagc       780
tgacagcttt gttcgcgtgg gcagagcctt ccacagtgaa tgtgtctgga cctcatgttg       840
ttgaggctgt cacagtcctg agtgtggact tggcaggtgc ctgttgaatc tgagctgcag       900
gttccttatc tgtcacacct gtgcctcctc agaggacagt ttttttgttg ttgtgttttt       960 ttgtttttt ttttttggta gatgcatgac ttgtgtgtga tgagagaatg gagacagagt      1020
ccctggctcc tctactgttt aacaacatgg ctttcttatt ttgtttgaat tgttaattca      1080
cagaatagca caaactacaa ttaaaactaa gcacaaagcc attctaagtc attggggaaa      1140
cggggtgaac ttcaggtgga tgaggagaca gaatagagtg ataggaagcg tctggcagat      1200
actccttttg ccactgctgt gtgattagac aggcccagtg agccgcgggg cacatgctgg      1260
ccgctcctcc ctcagaaaaa ggcagtggcc taaatccttt ttaaatgact tggctcgatg      1320
ctgtggggga ctggctgggc tgctgcaggc cgtgtgtctg tcagcccaac cttcacatct      1380
gtcacgttct ccacacgggg gagagacgca gtccgcccag gtccccgctt tctttggagg      1440
```

-continued

```
cagcagctcc cgcagggctg aagtctggcg taagatgatg gatttgattc gccctcctcc    1500
ctgtcataga gctgcagggt ggattgttac agcttcgctg gaaacctctg gaggtcatct    1560
cggctgttcc tgagaaataa aaagcctgtc atttcaaaca caaaaaaaaa aaaaaaaaaa    1620
aaaaaaaaa                                                            1629

<210> SEQ ID NO 5
<211> LENGTH: 1725
<212> TYPE: DNA
<213> ORGANISM: Artificial Sequence
<220> FEATURE:
<223> OTHER INFORMATION: A synthetic nucleic acid sequence

<400> SEQUENCE: 5
atggagctgc tgatccacag gttaagtgca atcttcctaa ctcttgctat taatgcattg      60
tacctcacct caagtcagaa cataactgag gagtttacc aatcgacatg tagtgcagtt      120
agcagaggtt attttagtgc tttaagaaca ggttggtata ccagtgtcat aacaatagaa      180
ttaagtaata taaaagaaac caaatgcaat ggaactgaca ctaaagtaaa acttataaaa      240
caagaattag ataagtataa gaatgcagtg acagaattac agctacttat gcaaacaca      300 ccagctgcca acaaccgggc cagaagagaa gcaccacagt atatgaacta tacaatcaat      360
accactaaaa acctaaatgt atcaataagc aagaagagga aacgaagatt tctgggcttc      420
ttgttaggtg taggatctgc aatagcaagt ggtatagctg tatccaaagt tctacacctt      480
gaaggagaag tgaacaagat caaaaatgct ttgttatcta caaacaaagc tgtagtcagt      540
ctatcaaatg gggtcagtgt tttaaccagc aaagtgttag atctcaagaa ttacataaat      600
aaccaattat tacccatagt aaatcaacag agctgtcgca tctccaacat tgaaacagtt      660
atagaattcc agcagaagaa cagcagattg ttggaaatca acagagaatt cagtgtcaat      720
gcaggtgtaa caacaccttt aagcacttac atgttaacaa acagtgagtt actatcattg      780
atcaatgata tgcctataac aaatgatcag aaaaaattaa tgtcaagcaa tgttcagata      840
gtaaggcaac aaagttattc tatcatgtct ataataaagg aagaagtcct tgcatatgtt      900
gtacagctac ctatctatgg tgtaatagat acaccttgct ggaaattaca cacatcacct      960
ctatgcacca ccaacatcaa agaaggatca aatatttgtt aacaaggac tgatagagga     1020 tggtattgtg ataatgcagg atcagtatcc ttctttccac aggctgacac ttgtaaagta     1080
cagtccaatc gagtattttg tgacactatg aacagtttga cattaccaag tgaagtcagc     1140
ctttgtaaca ctgacatatt caattccaag tatgactgca aaattatgac atcaaaaaca     1200
gacataagca gctcagtaat tacttctctt ggagctatag tgtcatgcta tggtaaaact     1260
aaatgcactg catccaacaa aaatcgtggg attataaaga cattttctaa tggttgtgac     1320
tatgtgtcaa acaaaggagt agatactgtg tcagtgggca cactttata ctatgtaaac     1380 aagctggaag gcaagaacct ttatgtaaaa ggggaaccta ataaaatta ctatgaccct     1440 ctagtgtttc cttctgatga gtttgatgca tcaatatctc aagtcaatga aaaaatcaat     1500
caaagtttag cttttattcg tagatctgat gaattactac ataatgtaaa tactggcaaa     1560
tctactacaa atattatgat aactacaatt attatagtaa tcattgtagt attgttatca     1620
ttaatagcta ttggtttgct gttgtattgc aaagccaaaa acacaccagt tacactaagc     1680
aaagaccaac taagtggaat caataatatt gcattcagca aatag                     1725

<210> SEQ ID NO 6
<211> LENGTH: 3681
```

-continued

<212> TYPE: DNA
<213> ORGANISM: Artificial Sequence
<220> FEATURE:
<223> OTHER INFORMATION: A synthetic nucleic acid sequence

<400> SEQUENCE: 6

```
gtgagcagaa tccatgtgca aggagagcag gcagttcagg acgagggtga gctggtctct      60
gcaggtttag tgctgtggca ctgtgcctgg tatatgctcc cggcaacttc tcctgactct     120
gccttcagac gagacttgga agacagtcac atctcagcag ctcctctgcc gttatccagc     180
ctgcctctga caagaaccca atgcccaacc ctaggccagc caagcctatg gctccttcct     240
tggcccttgg cccatcccca ggagtcttgc caagctggaa gactgcaccc aagggctcag     300
aacttctagg gaccaggggc tctgggggac ccttccaagg tcgggacctg cgaagtgggg     360
cccacacctc ttcttccttg aaccccctgc caccatccca gctgcagctg cctacagtgc     420
ccctagtcat ggtggcaccg tctggggccc gactaggtcc ctcaccccac ctacaggccc     480
ttctccagga cagaccacac ttcatgcatc agctctccac tgtggatgcc catgcccaga     540
cccctgtgct ccaagtgcgt ccactggaca acccagccat gatcagcctc ccaccacctt     600
ctgctgccac tggggtcttc tccctcaagg cccggcctgg cctgccacct gggatcaatg     660
tggccagtct ggaatgggtg tccagggagc cagctctact ctgcaccttc ccacgctcgg     720
gtacacccag gaaagacagc aaccttttgg ctgcacccca aggatcctac ccactgctgg     780
caaatggagt ctgcaagtgg cctggttgtg agaaggtctt cgaggagcca gaagagtttc     840
tcaagcactg ccaagcagat catctcctgg atgagaaagg caaggcccag tgcctcctcc     900
agagagaagt ggtgcagtct ctggagcagc agctggagct ggaaaaggag aagctgggag     960
ctatgcaggc ccacctggct gggaagatgg cgctggccaa ggctccatct gtggcctcaa    1020
tggacaagag ctcttgctgc atcgtagcca ccagtactca gggcagtgtg ctcccggcct    1080
ggtctgctcc tcgggaggct ccagacggcg gcctgtttgc agtgcggagg cacctctggg    1140
gaagccatgg caatagttcc ttcccagagt tcttccacaa catggactac ttcaagtacc    1200
acaatatgcg accccctttc acctatgcca cccttatccg atgggccatc ctggaagccc    1260
cggagaggca gaggacactc aatgaaatct accattggtt tactcgcatg ttcgcctact    1320
tcagaaacca ccccgccacc tggaagaatg ccatccgcca caacctgagc ctgcacaagt    1380
gctttgtgcg agtggagagc gagaagggag cagtgtggac cgtagatgaa tttgagtttc    1440
gcaagaagag gagccaacgc cccaacaagt gctccaatcc ctgcccttga cctcaaaacc    1500
aagaaaaggt gggcggggga gggggccaaa accatgagac tgaggctgtg ggggcaagga    1560
ggcaagtcct acgtgtacct atggaaaccg ggcgatgatg tgcctgctat cagggcctct    1620
gctccctatc tagctgccct cctagatcat atcatctgcc ttacagctga gaggggtgcc    1680
aatcccagcc tagcccctag ttccaaccta gccccaagat gaactttcca gtcaaagagc    1740
cctcacaacc agctatacat atctgccttg gccactgcca agcagaaaga tgacagacac    1800
catcctaata tttactcaac ccaaacccta aaacatgaag agcctgcctt ggtacattcg    1860
tgaactttca aagttagtca tgcagtcaca catgactgca gtcctactga ctcacacccc    1920
aaagcactca cccacaacat ctggaaccac gggcactatc acacataggt gtatatacag    1980
acccttacac agcaacagca ctggaacctt cacaattaca tccccccaaa ccacacaggc    2040
ataactgatc atacgcagcc tcaagcaatg cccaaaatac aagtcagaca cagcttgtca    2100
gaacacgctc gtgtgcacgt acacacatgc agcccctcca ctctatctcc tgagttccat    2160
```

-continued

```
gaatacacac cgactctcca agatgtaccc cacgtctcac ttgccactga ccccagttcc    2220
ctacccacaa gccccaatcc atgcctaagc gtggcccaca gaagaacttc tcttttattt    2280
gggatccaag gccctggcc cccagtgccc atccaataaa ctgtggtcag ctggacaatc    2340
accctgatca gatatgggaa catataagca gacagctggg tttaagatcc cagcaggaga    2400
aagcggatac caaatgaaag agagtgctag aacaggtgcc tcagcactgt ctccagcacc    2460
ccaaattcct gcctgtggtt aggagacatc catcagggct ctaggcctct cggacccggc    2520
ccaagaggcc agcattctcc tggcgaaggg ctcggtagtc ctcacagatc ttctccaggt    2580
tgctcaaagt cttcttgccc atctctgtct caatctaaga aaacaggatg cacacttctt    2640
cagcccctgc aggctgcccc tctactgaac tcctccctgc tcctcctatt cccgtaacag    2700
cagcctgttc cttcccatca ctgggcttct gggtatgtcc ttccctccac tccacctaaa    2760
gcagcaactt ctgccatggg ctctgggagg cattaggagc cgcaagctaa aagccagggc    2820
tcagagtagg ctactggcta gcttcaggtc ccaggcacag tgggcacgaa ggcaaagcct    2880
ctagctgtta gttgtctggt ttcaaagact ctcagcgcaa aacaaggaac tatcccctgg    2940
cctgtctcca ttccccttac cagtcccagg tctcacctgc tcctcaagat ctcgaacttc    3000
cctcatgata gtgcctgtgt cctcaatggt ctggatgagc tgactgcaat tctggagaca    3060
gcaagaatac aaggcttgca cctatgctgg ccctctccag ccaacccacc aggcacatgg    3120
ctcccctcac ctcatgcagg gcagctaggt acttgtaggc tttccgaaca gcatcatcct    3180
tcttagcatc ctgataagac aaaggggatc tccgagatat cagcaagcca ttccccctttt    3240 tccactactc tatgcccta taagaccacc ctttactagt actttgcctt catcctccac    3300
agagcaaagc taggccccaa gcaacagtgc acctaaagga ctcacagagg ggcaggcaac    3360
aactcagtcc cgcctccacc ctcccggagg ccagcctgct ccataccttg aacacaagct    3420
catcagtcac tgcaaatgtc cggtcgagct tcccagagag agagttgatt tccttctgca    3480
gttcctttgt gtccgacaag atctggtaga aaccagggta actatcagtg cacatcttgg    3540
gcaaggtagc tgatcagtga taacactcac gtgcctatac ttacatccag tcagggccca    3600
tgtcgctgtg ttggggtgac tattatgtgt tggagtgtgc ctgaacagct ctgcctagta    3660
gtgagcataa agtccctgtg t                                              3681
```

<210> SEQ ID NO 7
<211> LENGTH: 11664
<212> TYPE: DNA
<213> ORGANISM: Artificial Sequence
<220> FEATURE:
<223> OTHER INFORMATION: A synthetic nucleic acid sequence

<400> SEQUENCE: 7

```
ggtaccatgt ctatcctgac cctaagatta gttcctcggg tttgaggatt gcagcaacac     60
tgaccgttca ggccctggtc aaggtggggc tgctgcttct ccttggcttt ctttccaagg    120
agccaccaag aggcagaaag aaatgaagag acacaaagca aggcagaata gcacttcgga    180
tgacactgtc cgcattgccc gacagatatg gcactagact gcagccaaag gactctctga    240
aactattaac aaggttgtga gaacttgtga ccagtctgtg aggtgctgtg tctgggtgtc    300
atgtcactgg ggacatcatc agtgtcacca gtggcacagt ggaatgcctg gtgagctgag    360
acacacaaat gaggcaggcg tggtgggcac acacctgtaa tcccaacgga acgtaaacct    420
ggtatggcag tgctcacctg tatgtggtgg cactcaggaa gtggaggcag gagcattagg    480
agtctaaggt catcctcagc tacattgaca aatctgagac cagcctgggc gacatgagtc    540
```

-continued

```
cttgtgttaa aaaaaaaaaa aaaaaaaaaa aaaaaaaaag agagagagag agagagagag      600
agaatcagac agtggtggtg catgctttta atccagcact tgggaggcag aggcaaacag      660
attactgtga gatcaaggcc agcctggtct tcagagcaag ttccaggaca agcagggcta      720
catagaaaaa acccgtctct ataaacaaac aaaacaaaac aaaacaaaaa aaagcagatc      780
tcgtgactct ctgaagaagg ccatttcccg ccagtccttg gggttagccg taagtagcag      840
gctgtagtgt ctcgaggcca caaaaactag gagaaccctg ggaccacttc cagggtgtcg      900
ttttacatca catgtccaac tatttacctt catcttgggg ctagctccca ccccatacag      960
cctgtgagtg ctggaggact ttctagggag cctccgtagg aaaggcactg gcaggtctca     1020
gaaaaggatc ggggtcctga tgggggggcg ggggtcagta gtgcctaatg cactcagaca     1080
agcaccggcg ctgcagccag ccctgaactg cttttttctct aagcccagcc aggtgtggac     1140
atagcctcag aggaccacgt gtcagctgaa tcccatctca tgcccaggag gggtgactgg     1200
gagagatggg catctgcttc tgggtaaagc tacctaagag ccacagggga cacagaaatc     1260
tcagcctcac agggcacttt cctgtttgtc taatgctcct ctccctagca ccagccagga     1320
gtctatagaa tcagaggatt ttaaagtaag ggggagtgg gaggtcggtt ggccccagga     1380
gcaccctaag tgtgcccttc cggcacttac cctgcgtcaa gagccaggaa ggaagctctc     1440
aagggcgttg cataagagta gaggattgag aagcctgggg tggggctaga gaggctcatt     1500
ctgaccccac tcagcatccc ttgcacagtc cagagcgtgg ggatcaaacg agaccccctt     1560
gtttgacggt gaacaaagtc aggctgaggg ggttcgggaa gggggtaaag gactaggaac     1620
cgacatcggc cagcacacgg gaggtggaca ggggtgtccc tgctgagaag acctggaggg     1680
ctctcaagac acaggcaaac actgaggtca gcctgttccc atggagtcca gcccccaggt     1740
cctctcccct actataagag cccatgactc aagtagggta ctaagcagta ggcagccatg     1800
gccaagtcgc acctactgca gtggctactg ctgcttccta ccctctgctg cccaggtgca     1860
ggtgagtccc cggcctccct cacagaggcc tctccagcac ttactgagtc agctccgtgc     1920
ccagaaagac cccagtctgc acataatcca gaatttaaac gccagttagc tgagcacag     1980 agaagtccta gggcctcatc caaggtcaca gttagtggat ggatgttgaa gcaggaggac     2040
tcagagctgc ctggcagaag caatggccac tcctttgcaa tgaaactggg ttggaggtgg     2100
ggtggaggca gggtgccgag tgtatgctgg atcctgatga gagttgctct gaccccaact     2160
ccagctatca cgtcggcctc atccctggag tgtgcacaag gccctcaatt ctggtgccaa     2220
agcctggagc atgcagtgca gtgcagagcc ctggggcact gcctgcagga agtctggggg     2280
catgcaggag ctgtgagtag caccaagcgg gcactggaaa tccagggagg aggaactggg     2340
gtggattctg agcggacctt aggaaattgg agttcccaca aggctggggt ggcagggaat     2400
gatggaatgg tatagtgtga caggaaatgg tgggcagagt acaatagaag gaaacatggt     2460
ggaatgagat gaatggggtg ggcatggtgg gtaagacagg gtggatgtgt gggtaagaca     2520
gggtggatgt ggtgggtaag acagggtaga tgtggtgggt aagagggggt gagcatgtgg     2580
gtaagatggg gtggctgggg tgagatggac aagatggaat agaacagggt ggatcaagtg     2640
ggtggcacag aatgggatgg aatttgcaca atggatgag atgggatgat gggtgggtag     2700
ccttaaggta cctgtcagcc tgtgtctgag aaagcctcaa tccctggagt taggagcatg     2760
cccccaactc attagcctca cttgagaccc tttcttccag aatgacctgt gccaagagtg     2820
tgaggatatt gtccacctcc tcacaaagat gaccaaggaa gatgctttcc aggtaatggg     2880
```

-continued

```
aaacggtaca gtgtgatctg gtagaggcct ggcgtcaggg gactctggtg ggggcagacc    2940
tcagaaagac caggctaatc ctcccttctc tgctctccca ggaagcaatc cggaagttcc    3000
tggaacaaga atgtgatatc cttcccttga agctgcttgt gccccggtgt cgccaagtgc    3060
ttgatgtcta cctgcccctg gttattgact acttccagag ccagattgtg aggaccctga    3120
cctacctgcc gcacagtgca tgtgcctaag tggccactta cctatataag tggcacccca    3180
acacatgcac acacacacat acacacccac agacgcaata agacacacac acacacacgt    3240
acacacacac acacacacac acacacacac acacacttcc cactacagcc acaggaagct    3300
cagtctcttc atccagatac ccaaatcaga gcctgcctgc tcagcatact acagacattg    3360
agacccgccc tccatcccct cacccacaca tgcccacatt cttattgtca cacaatatgc    3420
tcacacacac tcactctttc cagacacatg ctcccaggcc ctacacagcc ccatctctct    3480
gtctttgtcc ctttcatagt gtcctaagat gcagtacttc acccagcctg ctccccataa    3540
ccccaggctc aaagactgtg gcccttgtcc ctgaatatga acctgggcag agaggggttc    3600
cctccttacc ctaaaacccc tcacctgttc catgccctag aaccccaaag ccatctgcaa    3660
tcatgtaggc ctgtgcccac gtgggcaggc taagccagaa cagaatccag ggatgccgga    3720
tgccgttcca aaccctctgc tggacaagct ggtcctccct gtgctgccag gagccctctt    3780
ggcaaggcct gggcctcaca ctcaggtaag ccagtccatt cccagcagct gctgggaatc    3840
cagaaggcta gcatggccgc tgagacgcgt gggcacccag agaggctgag ctcaaactag    3900
gaggcagaga tggcaaggtc aggcaaggtc acacaaccga ggtagctccc agcctaacca    3960
cacttcaccg cttccttcct caggacttct ctgagcaaca gctccccatt cccctgccct    4020
tctgctggct ttgcagaact ctgatcaagc gggttcaagc cgtgatcccc aaggtaagga    4080
ccacacagag ctcagagggg cccccaatag ctggcacctt cctccacctc aacactccaa    4140
gaaggctgtg aggagttaga tgaggagaca cccacacatt gctcctaccc aaggaacctt    4200
gaggctcagg tatgggaggt taggtcagag ccaccttctc ttccaacaga tcaccatcgg    4260
aaggctgaga agcactggtt gtcactgtag gaaaaaagta cattaatttc tcaaaaaaaa    4320
aaaaaaacag ttcatcaata gtaagcatct cttctgtcct ccaaatccat ggtagcctct    4380
gccagtgcct tgtcagatga ggattgttct ccccacaaat ggtcatggcc tatcaacact    4440
aacactaagc ccacatcagt cataaagaca acagggcaca cagtcaagcc tttctgaagc    4500
ctgtgtgatg gaaggaacgt gcagactata gagcaggatg agctgagggg tcgcacagat    4560
aaaaatggta acagacaggt cagccaggga gaggctctga agagggtaac aactaagcca    4620
agatctagga gaaaacaagg tccccagggg ccaaggacat ccatccatca ataaaaaatg    4680
agctcaatca gatgttggag ggagggactc tgtaaggagg gaccaggagc aggggggcagc    4740 gtttgggggtg taaatgatag ataaatgcct ttaaaatgag ctcagagggc taggaagatg    4800
gctcggtgag tacagtcctt gctgaacctg agttcagata cttgcaccct cataaaagtt    4860
ggggggtggg ctggagacat ggctcagtag ttaagagcac tgactgctct tctagaggtc    4920
ctgagttcaa ttcccagcaa ccacttggtg gctcacaacc acctataatg ggatctgatg    4980
ccctcttctg gtgtgtctga acttacatac ataaaataaa aataaaagtt gggggttgct    5040
cacagtcagc taatggatgg atcataggge tcccaatgga ggagctagag aaagtagcca    5100
aggagctaaa gggatctgca accctatagg tggaacaaca ttatgagcta accagtaccc    5160
cggagctctt gactctagct gcatatatat caaaagatgg cctagtcggc catcactgga    5220
aagagaggcc cattggactt gcaaacttta tatgccccag tacaggggaa taccagggcc    5280
```

-continued

```
aaaaaggggg agtgggtggg caggggagtg ggggtgggtg gatatggggg acttttggta   5340
tagcattgga aatgtaaatg agttaaatac ctaataaaaa atggaaaaaa aaaaagttgg   5400
gggttagcaa tgaacatttg taaccctaca cactaggtag tcagaaatag gcagatccct   5460
agagcatgct ggccagccag tctagccaaa tggatgagct tcagggttag tgtgagacct   5520
tgtctcaaaa aaaaaaaaaa aaaaaaaaaa aatggacggc ctgaagattc ggatcgacag   5580
ttaggaacat ttgctgcttt tcagaagagt gagttgggta cccagcacca ctgtcaggca   5640
gctcacaacc ccctgtaact gctgctctag ggaatccaat gccctcttct ggcagccaag   5700
ggcaccagca catatgtggc attcatatac tcagatacac agacatatgt aaaaataaaa   5760
ataaatcttt agaaaataat taggtaggga gtgaagtgac taaggaagac actcaatctt   5820
ggctctggcc tccacacaca tgtgcacatg tacttaaaca tctacgtgca aaacaaacaa   5880
acaaacaccc agccgtatca atgtgaacat cactgaggac cgaaggcatg agcaagactg   5940
ttaagagaca atgtatagac agatggagat ggcatcagaa ttgctgagag gggacaggca   6000
gccaacgggg gaccgtgctg cattgccagg gaagccaaga gagaagggtg tttgactgat   6060
tgaaaggcag ctgaaccatc aggcagggtg agagttaggc aggggatgtg gaagtgttcc   6120
aaaaagggga gcaggcatgg tgaggcttcc taaggtcaga agccattcta gcgtgttctc   6180
caggcagcag ggaccagaga gaggataagg ccagggaaag aggcatgggt ggaggtaatc   6240
caggagtgaa gaccatttca ccaatgagca gcttggtcat tgactacagt gactattgat   6300
ttacatcacc atgacaggag agccatgtgt gggtcaatga taacaggtgg gtctcttaag   6360
tgaagtgccc catttgggag ccatcacact ccaggggtgt ccatattctg agtcctcccc   6420
ctgcctcaac ctcctggcac tggggctagc tggtcacatg ggctgaataa ggagtaaagg   6480
aaaaagccac accctggtga cctctgtcac ccttcagcta gagcctgctt ggaattggag   6540
ttgaggtagg agatgtgctg gctttcccag gggttccaaa agccaaagac atgtcagctc   6600
tgggggccag cagaaggaac tgcctgtctt cctgatgcat aagcatggga aggtaggtgg   6660
ccctcggtca gggaatgggt ttgaattggg tcaggctgtt agatgccatg gccttgcagc   6720
cccctttcaa atgactcaag cctttagagc tagatctata tttggtgtca actgcagatt   6780
ctctcagtga ctccgggtgc acctgagacc cctgctgtct tggatgctca gtgacctgtg   6840
gacagaactg ctctttccta gaagggagaa aggggatgca tctggggtgc ccactcagtt   6900
gggcacagtg acatcgtgcc agaagaaggt tctatggttg tcctttctcc accttcaccc   6960
cagggtgtgc tggctgtggc tgtgtcccag gtgtgccacg tggtacccct ggtggtgggt   7020
ggcatctgcc agtgcctggc tgagcgctac acagttctcc tgctagacgc actgctgggc   7080
cgtgtggtgc cccagctagt ctgtggcctt gtcctccgat gttccactga ggatgccatg   7140
ggccctggta agacttgccc gtccctcccc cctccccaac tcacatccct ccagtgcaca   7200
tgggagggaa catggacaag gtggggttca ggaaccaaca cttttttttaa actatttatt   7260 tctatggata tggctgcttt tatttatata gctgaggctg gctttgaact cctaatttcc   7320
cttcctcagc cattcaaatg ttaggaaagg ctagcaatga ctgtactcag cttctagctc   7380
tctccaagtg gacttctccc agttgagtta aagagtgatg ggggaggggt ggggaacagg   7440
gcaggaccct gggagaaggc taagttcttt ttttgctcca gcttggacat ctatataccc   7500
catgtatgcc tggctcccac agaggccata aaggatgtca aatcccctag aattggaata   7560
actgacagtt atgagccatc atgtggggct ctgggaatcg aacctcagcc ctctggaaga   7620
```

-continued

```
gcagccagtg ctcttaacca cggaaccatc tctccagccc cagaaccaac acttgtacaa      7680
gacagtcctg ggggaaagat taaaacagag tcttactaca tagcacaggt tggcctcgag      7740
cttggtgcaa tcctcctgcc tcagcctctc aaatactggc atgacaaggt atgtgcctcc      7800
atacccagct tgctggacaa ttctaactgc tttctcttta gccctccctg ctgtggagcc      7860
tctgatagaa gaatggccac tacaggacac tgagtgccat ttctgcaagt ctgtgatcaa      7920
ccaggcctgg aacaccagtg aacaggctat gccacaggca atgcaccagg cctgccttcg      7980
cttctggcta gacaggcaaa aggtaggggg cccacgggtt ggatgtatgt catatgtgtg      8040
atggtgccga gctagaagag actttgtagc tagacacacg cacgatgctg gttcccagcc      8100
tggtggacag gcatgtgggt cagacaatga tgggattgta acaaatttaa ctggctagga      8160
gacatcatgg acccaaggct ttggactatg gaacatcagc aggccttctt tatggactaa      8220
gcacaagaaa agtcctgtta gtcccaacag gaaagggtca tactgccctt tcttggtttc      8280
actcgatggt gtgtttgcca cactgttctc ccagtgtgcc atgtcacccc catgatgggt      8340
ggtagcattt gacagtacct agcaggcacc agaaaatgag aaaagccagg gtcagctgga      8400
gcagaaaaag aacttagcct tttcccaggg tcctgttctg ccccaccctg ctcactctgt      8460
agaagtcctg caggagagag ctggaagctg gtaccatagt gctagcctgt aattctaaca      8520
tttggaaagg ctgaagaagg agaaatggga gttcaaagcc agcctcagct atataaataa      8580
tgagttcagg gtcagcctgg gctacatgag accctgtctg gtgaaaggag acagagatag      8640
gaaagaacat gaggcttggg taaggctcac tggcatggcc acaaccaagt ttgatccctg      8700
ggatccgtat ggtaaacaaa gagaatcaac tcctgtaaac tttccttatg aacacacaca      8760
cacacgaaaa cataattttg aagccaggct gtggtggtgc acacctttag tcctagccct      8820
tgggaggcag aagcagatgg atctaagttt gagcccagcc tggtctacag tgtgagctcc      8880
aggacagcca gggttacaca gagaaaccct gtctcacaaa accaaaaaga aatcaacaac      8940
cacaaagaac tgaacagata gttccttaag cctgtgatga atcccctcac tacagtggga      9000
ctttctttag agagggtcct atgtaactta aaccgcctcc acctcctttg tactgagact      9060
acaggcaggt accactactg agtttcatgt agttctgaag ttgaaactaa aggtttcatg      9120
catgctaggc aaccatgaga cgatgctaag ctgcaagcct gctccagctc caaggccctg      9180
gcttcctcca aagcctggtt tcagccaaac ttagatagag tccctttttt taagactcat      9240
tttatttgtg tttttagtgc atgtatgtat ggacatcatg tgtgtgtggt gccgggggga      9300 ggggtcaga agaggccatc agattccctg gaactggagt tgagtggtta taagccgtcc      9360
ttcctgtcct ccaaagagca gcaagtgcct aaccccgag ccatcagcca ttcagccctt      9420
cggttgagtc tttaatggtc agccaggcac tgatggaaaa acacaaaccc acagtccgga      9480
gtggcagagt gaggtagaac gccagatctg caggttaagt tctctcctag aggggggtct      9540
acatattgtg tctttcctca gtgtgaacag tttgtggaac agcacatgcc ccagctgctg      9600
gccctggtgc ctaggagcca ggatgcccac atcacctgcc aggtatgccc actcttcagc      9660
tggtcccagg agtcccctct gctcccacag tcccaccctc cttggtctat gatcctcaag      9720
agccccattt cttggatcca ggaagcctag ggctcagaag cccagaacta agtgtaccca      9780
tagaacaggc tttggacttg gagcagaaaa gaacacatac tgattaggtg ggaggggcaa      9840
gttcatgatg gatgggcagc tgggggctgg ggtatgatgc tccttattgc atgtggtgtg      9900
tttagtgacc agtttgttct atggtggggc tatagtatga ggtgggggtc ccactaagtc      9960
ccaaggccat tgacttaggg aatggcacaa ggggttctga aggtgaaggt gaagtgagag     10020
```

```
ttgtctccat agccttgaga attagacgta gaaagctgag gcccacgtgc tgtctccaac   10080
aggcccttgg cgtatgtgag gccccggcta gccctctgca gtgcttccaa accccacacc   10140
tctgagaacg cggtctccag gtgagtccag cctcctgggg agagagagga atgggtcttt   10200
gcttgctaag gtttgggaac aagatggtca tcctgcccac ttctgtggac tgtgtcatcc   10260
tacctctgcc aggcacagtt ccaggctcct cggggtctcc agtggttcca tcaggaaaag   10320
gcagtctttt ggacctatcg tcactccttg ctctcccacc ccatccagcc ctccacagct   10380
tctatctaag gcttcatcac atctgagctg cctgacctta aagatactcc atgttcgagc   10440
aatggccaac atttcttact tcactgtctc ggctgtctct ccctcagatg ccagcagcac   10500
catggtcacc tgacctcacc ctgcccaggc tccctgtttt ctaagccaga aatagctctg   10560
acaccagagt caggaaatga catggggagt gtggggcgag aaaggcaaca gtctctcaag   10620
tgaccctgac agtaatctgg tccaggtcac aatgtactta aagccagcgc tcgctgggta   10680
gtcatttatc catttgttcc catttgtgaa aatctgctgg tgtgcacagc tggcccacca   10740
cttctaatgc gaggaaggac cccagcactg tcacagccac tgtgggcaga ggggcacttc   10800
aagtcagtaa gtcccttggg ggccaattta atgtctcccc tcccatcccc catcaagtcc   10860
atctgggtgc gcgaagggag gcaatccagg agtcaccttt ttctagctct cagggctcta   10920
ggccttgcct gctgaagaag gaattgtgag agactccctg agttctggtc ccaactctgc   10980
tatcaacagt cagtggatcc cccgggaaaa tcgcacagcc cccacccttt gcgatatcac   11040
taaactagct gcaagtagcc caatgaaggg aacttcggca cttatgaact gtcaccatca   11100
cagtgacagt gaccctactc ccaccagtag ctactctcct tgaaaaagac cttacctccc   11160
accctaatgc tacttccttt cccacagcag cctgctccag aggacaagcc tcagcctgca   11220
ccctcagccc tgtgtcagtc tgtatgtccc agctctaact acagaccacc accaccacca   11280
ccaccaccac caccaccacc accaccacca ccaccaccac caccaccacc accacagtgg   11340
tttctggctc cccccggtga tggggggcgg caggcccacg tcctctggaa gccttcagaa   11400
ggggcttcgg gccttcgcct ccaccagagc caagccagct cccatagctc ccacagccca   11460
cagggactga gaagaactgt tgtggctcca agaagacatc gggtagaagc tgggtatagc   11520
cacaccaacc ccttgctaac atttctatga aatccaaact tgagaagaat aaagaatggg   11580
aacatggagc attattctaa gggctgtggg cgaggcgcag tgacagggca ctttcctagc   11640
aagcaggaaa cctgggttgg atcc                                          11664
```

<210> SEQ ID NO 8
<211> LENGTH: 1083
<212> TYPE: DNA
<213> ORGANISM: Artificial Sequence
<220> FEATURE:
<223> OTHER INFORMATION: A synthetic nucleic acid sequence

<400> SEQUENCE: 8

```
atggcgggac acctggcttc ggatttcgcc ttctcgcccc ctccaggtgg tggaggtgat     60
gggccagggg ggccggagcc gggctgggtt gatcctcgga cctggctaag cttccaaggc    120
cctcctggag ggccaggaat cgggccgggg gttgggccag gctctgaggt gtgggggatt    180
cccccatgcc ccccgccgta tgagttctgt gggggatgg cgtactgtgg gccccaggtt    240
ggagtggggc tagtgcccca aggcggcttg gagacctctc agcctgaggg cgaagcagga    300
gtcggggtgg agagcaactc cgatggggcc tccccggagc cctgcaccgt cacccctggt    360
```

-continued

```
gccgtgaagc tggagaagga gaagctggag caaaacccgg aggagtccca ggacatcaaa      420
gctctgcaga aagaactcga gcaatttgcc aagctcctga agcagaagag gatcaccctg      480
ggatatacac aggccgatgt ggggctcacc ctgggggttc tatttgggaa ggtattcagc      540
caaacgacca tctgccgctt tgaggctctg cagcttagct tcaagaacat gtgtaagctg      600
cggcccttgc tgcagaagtg ggtggaggaa gctgacaaca atgaaaatct tcaggagata      660
tgcaaagcag aaaccctcgt gcaggcccga aagagaaagc gaaccagtat cgagaaccga      720
gtgagaggca acctggagaa tttgttcctg cagtgcccga aacccacact gcagcagatc      780
agccacatcg cccagcagct tgggctcgag aaggatgtgg tccgagtgtg gttctgtaac      840
cggcgccaga agggcaagcg atcaagcagc gactatgcac aacgagagga ttttgaggct      900
gctgggtctc ctttctcagg gggaccagtg tcctttcctc tggcccccag gccccatttt      960
ggtaccccag gctatgggag ccctcacttc actgcactgt actcctcggt ccctttccct     1020 gaggggggaag cctttccccc tgtctccgtc accactctgg gctctcccat gcattcaaac   1080
tga                                                                  1083
```

<210> SEQ ID NO 9
<211> LENGTH: 954
<212> TYPE: DNA
<213> ORGANISM: Artificial Sequence
<220> FEATURE:
<223> OTHER INFORMATION: A synthetic nucleic acid sequence

<400> SEQUENCE: 9

```
atgtacaaca tgatggagac ggagctgaag ccgccgggcc cgcagcaaac ttcggggggc       60
ggcggcggca actccaccgc ggcggcggcc ggcggcaacc agaaaaacag cccggaccgc      120
gtcaagcggc ccatgaatgc cttcatggtg tggtcccgcg ggcagcggcg caagatggcc      180
caggagaacc ccaagatgca caactcggag atcagcaagc gcctgggcgc cgagtggaaa      240
cttttgtcgg agacggagaa gcggccgttc atcgacgagg ctaagcggct gcgagcgctg      300
cacatgaagg agcacccgga ttataaatac cggccccggc ggaaaaccaa gacgctcatg      360
aagaaggata gtacacgct gccccggcggg ctgctggccc ccggcggcaa tagcatggcg      420
agcggggtcg gggtgggcgc cggcctgggc gcgggcgtga accagcgcat ggacagttac      480
gcgcacatga cggctggag caacggcagc tacagcatga tgcaggacca gctgggctac      540
ccgcagcacc cgggcctcaa tgcgcacggc gcagcgcaga tgcagcccat gcaccgctac      600
gacgtgagcg ccctgcagta caactccatg accagctcgc agacctacat gaacggctcg      660
cccacctaca gcatgtccta ctcgcagcag ggcacccctg gcatggctct tggctccatg      720
ggttcggtgg tcaagtccga ggccagctcc agccccctg tggttacctc ttcctcccac      780
tccagggcgc cctgccaggc cggggacctc cgggacatga tcagcatgta tctccccggc      840
gccgaggtgc cggaacccgc cgccccagc agacttcaca tgtcccagca ctaccagagc      900
ggcccggtgc ccggcacggc cattaacggc acactgcccc tctcacacat gtga           954
```

<210> SEQ ID NO 10
<211> LENGTH: 1440
<212> TYPE: DNA
<213> ORGANISM: Artificial Sequence
<220> FEATURE:
<223> OTHER INFORMATION: A synthetic nucleic acid sequence

<400> SEQUENCE: 10

```
atgaggcagc cacctggcga gtctgacatg gctgtcagcg acgcgctgct cccatctttc       60
```

-continued

```
tccacgttcg cgtctggccc ggcgggaagg gagaagacac tgcgtcaagc aggtgccccg      120
aataaccgct ggcgggagga gctctcccac atgaagcgac ttcccccagt gcttcccggc      180
cgcccctatg acctggcggc ggcgaccgtg gccacagacc tggagagcgg cggagccggt      240
gcggcttgcg gcggtagcaa cctggcgccc ctacctcgga gagagaccga ggagttcaac      300
gatctcctgg acctggactt tattctctcc aattcgctga cccatcctcc ggagtcagtg      360
gccgccaccg tgtcctcgtc agcgtcagcc tcctcttcgt cgtcgccgtc gagcagcggc      420
cctgccagcg cgccctccac ctgcagcttc acctatccga tccgggccgg gaacgacccg      480
ggcgtggcgc cgggcggcac gggcggaggc ctcctctatg gcagggagtc cgctccccct      540
ccgacggctc ccttcaacct ggcggacatc aacgacgtga gcccctcggg cggcttcgtg      600
gccgagctcc tgcggccaga attggacccg gtgtacattc cgccgcagca gccgcagccg      660
ccaggtggcg ggctgatggg caagttcgtg ctgaaggcgt cgctgagcgc ccctggcagc      720
gagtacggca gcccgtcggt catcagcgtc agcaaaggca gccctgacgg cagccacccg      780
gtggtggtgg cgccctacaa cggcgggccg ccgcgcacgt gccccaagat caagcaggag      840
gcggtctctt cgtgcaccca cttgggcgct ggaccccctc tcagcaatgg ccaccggccg      900
gctgcacacg acttccccct ggggcggcag ctccccagca ggactacccc gaccctgggt      960
cttgaggaag tgctgagcag cagggactgt caccctgccc tgccgcttcc tcccggcttc     1020
catccccacc cggggcccaa ttacccatcc ttcctgcccg atcagatgca gccgcaagtc     1080
ccgccgctcc attaccaaga gctcatgcca cccggttcct gcatgccaga ggagcccaag     1140
ccaaagaggg gaagacgatc gtggccccgg aaaaggaccg ccacccacac ttgtgattac     1200
gcgggctgcg gcaaaaccta cacaaagagt tcccatctca aggcacacct gcgaacccac     1260
acaggtgaga aaccttacca ctgtgactgg gacggctgtg gatggaaatt cgcccgctca     1320
gatgaactga ccaggcacta ccgtaaacac acggggcacc gcccgttcca gtgccaaaaa     1380
tgcgaccgag cattttccag gtcggaccac ctcgccttac acatgaagag gcattttaa      1440
```

```
<210> SEQ ID NO 11
<211> LENGTH: 1365
<212> TYPE: DNA
<213> ORGANISM: Artificial Sequence
<220> FEATURE:
<223> OTHER INFORMATION: A synthetic nucleic acid sequence

<400> SEQUENCE: 11
```

```
ctggattttt ttcgggtagt ggaaaaccag cagcctcccg cgacgatgcc cctcaacgtt       60
agcttcacca acaggaacta tgacctcgac tacgactcgg tgcagccgta tttctactgc      120
gacgaggagg agaacttcta ccagcagcag cagcagagcg agctgcagcc cccggcgccc      180
agcgaggata tctggaagaa attcgagctg ctgcccaccc cgcccctgtc ccctagccgc      240
cgctccgggc tctgctcgcc ctcctacgtt gcggtcacac ccttctccct tcggggagac      300
aacgacggcg gtggcgggag cttctccacg gccgaccagc tggagatggt gaccgagctg      360
ctgggaggag acatggtgaa ccagagtttc atctgcgacc cggacgacga gaccttcatc      420
aaaaacatca tcatccagga ctgtatgtgg agcggcttct cggccgccgc caagctcgtc      480
tcagagaagc tggcctccta ccaggctgcg cgcaaagaca gcggcagccc gaaccccgcc      540
cgcggccaca gcgtctgctc cacctccagc ttgtacctgc aggatctgag cgccgccgcc      600
tcagagtgca tcgacccctc ggtggtcttc ccctaccctc tcaacgacag cagctcgccc      660
```

-continued

```
aagtcctgcg cctcgcaaga ctccagcgcc ttctctccgt cctcggattc tctgctctcc      720
tcgacggagt cctccccgca gggcagcccc gagccctgg tgctccatga ggagacaccg       780
cccaccacca gcagcgactc tgaggaggaa caagaagatg aggaagaaat cgatgttgtt      840
tctgtggaaa agaggcaggc tcctggcaaa aggtcagagt ctggatcacc ttctgctgga      900
ggccacagca aacctcctca cagcccactg gtcctcaaga ggtgccacgt ctccacacat      960
cagcacaact acgcagcgcc tccctccact cggaaggact atcctgctgc caagagggtc      1020
aagttggaca gtgtcagagt cctgagacag atcagcaaca accgaaaatg caccagcccc      1080
aggtcctcgg acaccgagga gaatgtcaag aggcgaacac acaacgtctt ggagcgccag      1140
aggaggaacg agctaaaacg gagctttttt gccctgcgtg accagatccc ggagttggaa      1200
aacaatgaaa aggcccccaa ggtagttatc cttaaaaaag ccacagcata catcctgtcc      1260
gtccaagcag aggagcaaaa gctcatttct gaagaggact tgttgcggaa acgacgagaa      1320
cagttgaaac acaaacttga acagctacgg aactcttgtg cgtaa                      1365
```

```
<210> SEQ ID NO 12
<211> LENGTH: 4107
<212> TYPE: DNA
<213> ORGANISM: Artificial Sequence
<220> FEATURE:
<223> OTHER INFORMATION: A synthetic nucleic acid sequence

<400> SEQUENCE: 12
```

```
atggataaga aatactcaat aggcttagat atcggcacaa atagcgtcgg atgggcggtg       60
atcactgatg aatataaggt tccgtctaaa aagttcaagg ttctgggaaa tacagaccgc      120
cacagtatca aaaaaaatct tatagggggct ctttttatttg acagtggaga gacagcggaa     180
gcgactcgtc tcaaacggac agctcgtaga aggtatacac gtcggaagaa tcgtatttgt      240
tatctacagg agatttttttc aaatgagatg gcgaaagtag atgatagttt ctttcatcga      300
cttgaagagt cttttttggt ggaagaagac aagaagcatg aacgtcatcc tattttttgga      360 aatatagtag atgaagttgc ttatcatgag aaatatccaa ctatctatca tctgcgaaaa      420 aaaattggtag attctactga taaagcggat ttgcgcttaa tctatttggc cttagcgcat      480
atgattaagt ttcgtggtca ttttttgatt gagggagatt taaatcctga taatagtgat      540
gtggacaaac tatttatcca gttggtacaa acctacaatc aattatttga agaaaaccct      600
attaacgcaa gtggagtaga tgctaaagcg attctttctg cacgattgag taaatcaaga      660
cgattagaaa atctcattgc tcagctcccc ggtgagaaga aaaatggctt atttgggaat      720
ctcattgctt tgtcattggg tttgaccccct aattttaaat caaattttga tttggcagaa      780
gatgctaaat tacagctttc aaaagatact tacgatgatg atttagataa tttattggcg      840
caaattggag atcaatatgc tgatttgtt ttggcagcta agaatttatc agatgctatt      900
ttactttcag atatcctaag agtaaatact gaaataacta aggctcccct atcagcttca      960
atgattaaac gctacgatga acatcatcaa gacttgactc ttttaaaagc tttagttcga      1020
caacaacttc agaaaagta aagaaaatc tttttttgatc aatcaaaaaa cggatatgca      1080
ggttatattg atgggggagc tagccaagaa gaatttatat aatttatcaa accaatttta      1140
gaaaaaatgg atggtactga ggaattattg gtgaaactaa atcgtgaaga tttgctgcgc      1200
aagcaacgga cctttgacaa cggctctatt ccccatcaaa ttcacttggg tgagctgcat      1260
gctattttga aagacaaga agactttttat ccattttttaa aagacaatcg tgagaagatt      1320
gaaaaaatct tgacttttcg aattccttat tatgttggtc cattggcgcg tggcaatagt      1380
```

-continued

```
cgttttgcat ggatgactcg gaagtctgaa gaaacaatta ccccatggaa ttttgaagaa      1440
gttgtcgata aaggtgcttc agctcaatca tttattgaac gcatgacaaa ctttgataaa      1500
aatcttccaa atgaaaaagt actaccaaaa catagtttgc tttatgagta ttttacggtt      1560
tataacgaat tgacaaaggt caaatatgtt actgaaggaa tgcgaaaacc agcatttctt      1620
tcaggtgaac agaagaaagc cattgttgat ttactcttca aaacaaatcg aaaagtaacc      1680
gttaagcaat taaaagaaga ttatttcaaa aaaatagaat gttttgatag tgttgaaatt      1740
tcaggagttg aagatagatt taatgcttca ttaggtacct accatgattt gctaaaaatt      1800
attaaagata aagatttttt ggataatgaa gaaaatgaag atatcttaga ggatattgtt      1860
ttaacattga ccttatttga agatagggag atgattgagg aaagacttaa aacatatgct      1920
cacctctttg atgataaggt gatgaaacag cttaaacgtc gccgttatac tggttgggga      1980
cgtttgtctc gaaaattgat taatggtatt agggataagc aatctggcaa aacaatatta      2040 gatttttttga aatcagatgg ttttgccaat cgcaatttta tgcagctgat ccatgatgat      2100
agtttgacat ttaaagaaga cattcaaaaa gcacaagtgt ctggacaagg cgatagttta      2160
catgaacata ttgcaaattt agctggtagc cctgctatta aaaaaggtat tttacagact      2220
gtaaaagttg ttgatgaatt ggtcaaagta atggggcggc ataagccaga aaatatcgtt      2280
attgaaatgg cacgtgaaaa tcagacaact caaaagggcc agaaaaattc gcgagagcgt      2340
atgaaacgaa tcgaagaagg tatcaaagaa ttaggaagtc agattcttaa agagcatcct      2400
gttgaaaata ctcaattgca aaatgaaaag ctctatctct attatctcca aaatggaaga      2460
gacatgtatg tggaccaaga attagatatt aatcgtttaa gtgattatga tgtcgatcac      2520
attgttccac aaagtttcct taaagacgat tcaatagaca ataaggtctt aacgcgttct      2580
gataaaaatc gtggtaaatc ggataacgtt ccaagtgaag aagtagtcaa aaagatgaaa      2640
aactattgga gacaacttct aaacgccaag ttaatcactc aacgtaagtt tgataattta      2700
acgaaagctg aacgtggagg tttgagtgaa cttgataaag ctggttttat caaacgccaa      2760
ttggttgaaa ctcgccaaat cactaagcat gtggcacaaa ttttggatag tcgcatgaat      2820
actaaatacg atgaaaatga taaacttatt cgagaggtta aagtgattac cttaaaatct      2880
aaattagttt ctgacttccg aaaagatttc caattctata agtacgtga  gattaacaat      2940 taccatcatg cccatgatgc gtatctaaat gccgtcgttg gaactgcttt gattaagaaa      3000
tatccaaaac ttgaatcgga gtttgtctat ggtgattata agtttatga  tgttcgtaaa      3060 atgattgcta agtctgagca agaaataggc aaagcaaccg caaatatttt cttttactct      3120
aatatcatga acttcttcaa aacagaaatt acacttgcaa atggagagat tcgcaaacgc      3180
cctctaatcg aaactaatgg ggaaactgga gaaattgtct gggataaagg gcgagatttt      3240
gccacagtgc gcaaagtatt gtccatgccc caagtcaata ttgtcaagaa aacagaagta      3300
cagacaggcg gattctccaa ggagtcaatt ttaccaaaaa gaaattcgga caagcttatt      3360
gctcgtaaaa aagactggga tccaaaaaaa tatggtggtt ttgatagtcc aacggtagct      3420
tattcagtcc tagtggttgc taaggtggaa aaagggaaat cgaagaagtt aaaatccgtt      3480
aaagagttac tagggatcac aattatggaa agaagttcct ttgaaaaaaa tccgattgac      3540 ttttttagaag ctaaaggata taaggaagtt aaaaaagact taatcattaa actacctaaa      3600
tatagtcttt ttgagttaga aaacggtcgt aaacggatgc tggctagtgc cggagaatta      3660
caaaaaggaa atgagctggc tctgccaagc aaatatgtga ttttttata tttagctagt      3720
```

-continued

```
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactga                                         4107
```

<210> SEQ ID NO 13
<211> LENGTH: 4104
<212> TYPE: DNA
<213> ORGANISM: Artificial Sequence
<220> FEATURE:
<223> OTHER INFORMATION: A synthetic nucleic acid sequence

<400> SEQUENCE: 13

```
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tataggggct ctttttatttg acagtggaga gacagcggaa     180
gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt cttttttggt ggaagaagac aagaagctga acgtcatcct attttttggaa     360 atatagtaga tgaagttgct tatcatgaga aatatccaac tatctacatc tgcgaaaaaa     420
attggtagat tctactgata aagcggattt gcgcttaatc tatttggcct tagcgcatat     480
gattaagttt cgtggtcatt ttttgattga gggagattta aatcctgata atagtgatgt     540
ggacaaacta tttatccagt tggtacaaac ctacaatcaa ttatttgaag aaaaccctat     600
taacgcaagg ggagtagatg ctaaagcgat tctttctgca cgattgagta aatcaagacg     660
attagaaaat ctcattgctc agctccccgg tgagaagaaa aatggcttat ttgggaatct     720
cattgctttg tcattgggtt tgacccctaa ttttaaatca aattttgatt ggcagaaga     780 tgctaaatta cagctttcaa aagatactta cgatgatgat ttagataatt tattggcgca     840
aattggagat caatatgctg atttgttttt ggcagctaag aatttatcag atgctatttt     900
actttcagat atcctaagag taaatactga ataactaag gctcccctat cagcttcaat     960
gattaaacgc tacgatgaac atcatcaaga cttgactctt ttaaaagctt tagttcgaca    1020
acaacttcca gaaaagtata agaaatctt ttttgatcaa tcaaaaaacg gatatgcagg    1080
ttatattgat gggggagcta gccaagaaga attttataaa tttatcaaac caattttaga    1140
aaaaatggat ggtactgagg aattattggt gaaactaaat cgtgaagatt tgctgcgcaa    1200
gcaacggacc tttgacaacg ctctattcc ccatcaaatt cacttgggtg agctgcatgc    1260
tattttgaga agacaagaag actttttatcc attttttaaaa gacaatcgtg agaagattga    1320
aaaaatcttg acttttcgaa ttccttatta tgttggtcca ttggcgcgtg gcaatagtcg    1380
ttttgcatgg atgactcgga agtctgaaga aacaattacc ccatggaatt ttgaagaagt    1440
tgtcgataaa ggtgcttcag ctcaatcatt tattgaacgc atgacaaact ttgataaaaa    1500
tcttccaaat gaaaaagtac taccaaaaca tagtttgctt tatgagtatt ttacggttta    1560
taacgaattg acaaaggtca atatgttac tgaaggaatg cgaaaccag catttctttc    1620 aggtgaacag aagaaagcca ttgttgattt actcttcaaa acaaatcgaa aagtaaccgt    1680
```

-continued

```
taagcaatta aaagaagatt atttcaaaaa aatagaatgt tttgatagtg ttgaaatttc     1740
aggagttgaa gatagattta atgcttcatt aggtacctac catgatttgc taaaaattat     1800
taaagataaa gatttttttgg ataatgaaga aaatgaagat atcttagagg atattgtttt     1860
aacattgacc ttatttgaag atagggagat gattgaggaa agacttaaaa catatgctca     1920
cctctttgat gataaggtga tgaaacagct taaacgtcgc cgttatactg gttggggacg     1980
tttgtctcga aaattgatta atggtattag ggataagcaa tctggcaaaa caatattaga     2040
ttttttgaaa tcagatggtt ttgccaatcg caattttatg cagctgatcc atgatgatag     2100
tttgacattt aaagaagaca ttcaaaaagc acaagtgtct ggacaaggcg atagtttaca     2160
tgaacatatt gcaaatttag ctggtagccc tgctattaaa aaaggtattt tacagactgt     2220
aaaagttgtt gatgaattgg tcaaagtaat ggggcggcat aagccagaaa atatcgttat     2280
tgaaatggca cgtgaaaatc agacaactca aaagggccag aaaaattcgc gagagcgtat     2340
gaaacgaatc gaagaaggta tcaaagaatt aggaagtcag attcttaaag agcatcctgt     2400
tgaaaatact caattgcaaa atgaaaagct ctatctctat tatctccaaa atggaagaga     2460
catgtatgtg gaccaagaat tagatattaa tcgtttaagt gattatgatg tcgatcacat     2520
tgttccacaa agtttcctta aagacgattc aatagacaat aaggtcttaa cgcgttctga     2580
taaaaatcgt ggtaaatcgg ataacgttcc aagtgaagaa gtagtcaaaa agatgaaaaa     2640
ctattggaga caacttctaa acgccaagtt aatcactcaa cgtaagtttg ataatttaac     2700
gaaagctgaa cgtggaggtt tgagtgaact tgataaagct ggttttatca aacgccaatt     2760
ggttgaaact cgccaaatca ctaagcatgt ggcacaaatt ttggatagtc gcatgaatac     2820
taaatacgat gaaaatgata aacttattcg agaggttaaa gtgattacct taaaatctaa     2880
attagtttct gacttccgaa aagatttcca attctataaa gtacgtgaga ttaacaatta     2940
ccatcatgcc catgatgcgt atctaaatgc cgtcgttgga actgctttga ttaagaaata     3000
tccaaaactt gaatcggagt ttgtctatgg tgattataaa gtttatgatg ttcgtaaaat     3060
gattgctaag tctgagcaag aaataggcaa agcaaccgca aaatatttct tttactctaa     3120
tatcatgaac ttcttcaaaa cagaaattac acttgcaaat ggagagattc gcaaacgccc     3180
tctaatcgaa actaatgggg aaactggaga aattgtctgg gataaagggc gagattttgc     3240
cacagtgcgc aaagtattgt ccatgcccca agtcaatatt gtcaagaaaa cagaagtaca     3300
gacaggcgga ttctccaagg agtcaatttt accaaaaaga aattcggaca gcttattgc     3360 tcgtaaaaaa gactgggatc caaaaaaata tggtggtttt gatagtccaa cggtagctta     3420
ttcagtccta gtggttgcta aggtggaaaa agggaaatcg aagaagttaa aatccgttaa     3480
agagttacta gggatcacaa ttatggaaag aagttccttt gaaaaaaatc cgattgactt     3540
tttagaagct aaaggatata aggaagttaa aaaagactta atcattaaac tacctaaata     3600
tagtcttttt gagttagaaa acggtcgtaa acggatgctg gctagtgccg gagaattaca     3660
aaaaggaaat gagctggctc tgccaagcaa atatgtgaat tttttatatt tagctagtca     3720
ttatgaaaag ttgaagggta gtccagaaga taacgaacaa aaacaattgt ttgtggagca     3780
gcataagcat tatttagatg agattattga gcaaatcagt gaattttcta gcgtgttat     3840 tttagcagat gccaatttag ataaagttct tagtgcatat aacaaacata gagacaaacc     3900
aatacgtgaa caagcagaaa atattattca tttatttacg ttgacgaatc ttggagctcc     3960
cgctgctttt aaatattttg atacaacaat tgatcgtaaa cgatatacgt ctacaaaaga     4020
```

-continued

```
agttttagat gccactctat ccatcaatcc atcactggtc tttatgaaac acgcattgat      4080
ttgagtcagc taggaggtga ctga                                            4104
```

<210> SEQ ID NO 14
<211> LENGTH: 1054
<212> TYPE: PRT
<213> ORGANISM: Artificial Sequence
<220> FEATURE:
<223> OTHER INFORMATION: A synthetic amino acid sequence

<400> SEQUENCE: 14

```
Met Lys Glu Lys Tyr Ile Leu Gly Leu Asp Leu Gly Ile Thr Ser Val
1               5                   10                  15

Gly Tyr Gly Ile Ile Asn Phe Glu Thr Lys Lys Ile Ile Asp Ala Gly
                20                  25                  30

Val Arg Leu Phe Pro Glu Ala Asn Val Asp Asn Asn Glu Gly Arg Arg
            35                  40                  45

Ser Lys Arg Gly Ser Arg Arg Leu Lys Arg Arg Ile His Arg Leu
        50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                85                  90                  95

Ser Glu Ile Leu Ser Lys Asp Glu Leu Ala Ile Ala Leu Leu His Leu
            100                 105                 110

Ala Lys Arg Arg Gly Ile His Asn Ile Asn Val Ser Ser Glu Asp Glu
            115                 120                 125

Asp Ala Ser Asn Glu Leu Ser Thr Lys Glu Gln Ile Asn Arg Asn Asn
        130                 135                 140

Lys Leu Leu Lys Asp Lys Tyr Val Cys Glu Val Gln Leu Gln Arg Leu
145                 150                 155                 160

Lys Glu Gly Gln Ile Arg Gly Glu Lys Asn Arg Phe Lys Thr Thr Asp
                165                 170                 175

Ile Leu Lys Glu Ile Asp Gln Leu Leu Lys Val Gln Lys Asp Tyr His
            180                 185                 190

Asn Leu Asp Ile Asp Phe Ile Asn Gln Tyr Lys Glu Ile Val Glu Thr
            195                 200                 205

Arg Arg Glu Tyr Phe Glu Gly Pro Gly Gln Gly Ser Pro Phe Gly Trp
        210                 215                 220

Asn Gly Asp Leu Lys Lys Trp Tyr Glu Met Leu Met Gly His Cys Thr
225                 230                 235                 240

Tyr Phe Pro Gln Glu Leu Arg Ser Val Lys Tyr Ala Tyr Ser Ala Asp
                245                 250                 255

Leu Phe Asn Ala Leu Asn Asp Leu Asn Asn Leu Ile Ile Gln Arg Asp
            260                 265                 270

Asn Ser Glu Lys Leu Glu Tyr His Glu Lys Tyr His Ile Ile Glu Asn
        275                 280                 285

Val Phe Lys Gln Lys Lys Lys Pro Thr Leu Lys Gln Ile Ala Lys Glu
        290                 295                 300

Ile Gly Val Asn Pro Glu Asp Ile Lys Gly Tyr Arg Ile Thr Lys Ser
305                 310                 315                 320

Gly Thr Pro Gln Phe Thr Glu Phe Lys Leu Tyr His Asp Leu Lys Ser
                325                 330                 335

Ile Val Phe Asp Lys Ser Ile Leu Glu Asn Glu Ala Ile Leu Asp Gln
            340                 345                 350
```

```
Ile Ala Glu Ile Leu Thr Ile Tyr Gln Asp Glu Gln Ser Ile Lys Glu
        355                 360                 365

Glu Leu Asn Lys Leu Pro Glu Ile Leu Asn Glu Gln Asp Lys Ala Glu
        370                 375                 380

Ile Ala Lys Leu Ile Gly Tyr Asn Gly Thr His Arg Leu Ser Leu Lys
385                 390                 395                 400

Cys Ile His Leu Ile Asn Glu Glu Leu Trp Gln Thr Ser Arg Asn Gln
                405                 410                 415

Met Glu Ile Phe Asn Tyr Leu Asn Ile Lys Pro Asn Lys Val Asp Leu
                420                 425                 430

Ser Glu Gln Asn Lys Ile Pro Lys Asp Met Val Asn Asp Phe Ile Leu
        435                 440                 445

Ser Pro Val Val Lys Arg Thr Phe Ile Gln Ser Ile Asn Val Ile Asn
        450                 455                 460

Lys Val Ile Glu Lys Tyr Gly Ile Pro Glu Asp Ile Ile Ile Glu Leu
465                 470                 475                 480

Ala Arg Glu Asn Asn Ser Asp Asp Arg Lys Lys Phe Ile Asn Asn Leu
                485                 490                 495

Gln Lys Lys Asn Glu Ala Thr Arg Lys Arg Ile Asn Glu Ile Ile Gly
        500                 505                 510

Gln Thr Gly Asn Gln Asn Ala Lys Arg Ile Val Glu Lys Ile Arg Leu
        515                 520                 525

His Asp Gln Gln Glu Gly Lys Cys Leu Tyr Ser Leu Glu Ser Ile Ala
        530                 535                 540

Leu Met Asp Leu Leu Asn Asn Pro Gln Asn Tyr Glu Val Asp His Ile
545                 550                 555                 560

Ile Pro Arg Ser Val Ala Phe Asp Asn Ser Ile His Asn Lys Val Leu
                565                 570                 575

Val Lys Gln Ile Glu Asn Ser Lys Lys Gly Asn Arg Thr Pro Tyr Gln
        580                 585                 590

Tyr Leu Asn Ser Ser Asp Ala Lys Leu Ser Tyr Asn Gln Phe Lys Gln
        595                 600                 605

His Ile Leu Asn Leu Ser Lys Ser Lys Asp Arg Ile Ser Lys Lys Lys
        610                 615                 620

Lys Asp Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Ser Tyr Leu Lys Ala Tyr Phe Ser Ala Asn Asn Met Asp
                660                 665                 670

Val Lys Val Lys Thr Ile Asn Gly Ser Phe Thr Asn His Leu Arg Lys
        675                 680                 685

Val Trp Arg Phe Asp Lys Tyr Arg Asn His Gly Tyr Lys His His Ala
        690                 695                 700

Glu Asp Ala Leu Ile Ile Ala Asn Ala Asp Phe Leu Phe Lys Glu Asn
705                 710                 715                 720

Lys Lys Leu Gln Asn Ala Asn Lys Ile Leu Glu Lys Pro Thr Ile Glu
                725                 730                 735

Asn Asn Thr Lys Lys Val Thr Val Glu Lys Glu Glu Asp Tyr Asn Asn
                740                 745                 750

Val Phe Glu Thr Pro Lys Leu Val Glu Asp Ile Lys Gln Tyr Arg Asp
        755                 760                 765
```

-continued

```
Tyr Lys Phe Ser His Arg Val Asp Lys Lys Pro Asn Arg Gln Leu Ile
    770             775             780

Asn Asp Thr Leu Tyr Ser Thr Arg Met Lys Asp Glu His Asp Tyr Ile
785             790             795             800

Val Gln Thr Ile Thr Asp Ile Tyr Gly Lys Asp Asn Thr Asn Leu Lys
                805             810             815

Lys Gln Phe Asn Lys Asn Pro Glu Lys Phe Leu Met Tyr Gln Asn Asp
            820             825             830

Pro Lys Thr Phe Glu Lys Leu Ser Ile Ile Met Lys Gln Tyr Ser Asp
            835             840             845

Glu Lys Lys Pro Leu Ala Lys Tyr Tyr Glu Glu Thr Gly Glu Tyr Leu
    850             855             860

Thr Lys Tyr Ser Lys Lys Asn Asn Gly Pro Ile Val Lys Lys Ile Lys
865             870             875             880

Leu Leu Gly Asn Lys Val Gly Asn His Leu Asp Val Thr Asn Lys Tyr
            885             890             895

Glu Asn Ser Thr Lys Lys Leu Val Lys Leu Ser Ile Lys Asn Tyr Arg
            900             905             910

Phe Asp Val Tyr Leu Thr Glu Lys Gly Tyr Lys Phe Val Thr Ile Ala
            915             920             925

Tyr Leu Asn Val Phe Lys Lys Asp Asn Tyr Tyr Tyr Ile Pro Lys Asp
    930             935             940

Lys Tyr Gln Glu Leu Lys Glu Lys Lys Ile Lys Asp Thr Asp Gln
945             950             955             960

Phe Ile Ala Ser Phe Tyr Lys Asn Asp Leu Ile Lys Leu Asn Gly Asp
            965             970             975

Leu Tyr Lys Ile Ile Gly Val Asn Ser Asp Asp Arg Asn Ile Ile Glu
            980             985             990

Leu Asp Tyr Tyr Asp Ile Lys Tyr Lys Asp Tyr Cys Glu Ile Asn Asn
            995             1000            1005

Ile Lys Gly Glu Pro Arg Ile Lys Lys Thr Ile Gly Lys Lys Thr Glu
    1010            1015            1020

Ser Ile Glu Lys Phe Thr Thr Asp Val Leu Gly Asn Leu Tyr Leu His
1025            1030            1035            1040

Ser Thr Glu Lys Ala Pro Gln Leu Ile Phe Lys Arg Gly Leu
            1045            1050
```

```
<210> SEQ ID NO 15
<211> LENGTH: 1370
<212> TYPE: PRT
<213> ORGANISM: Artificial Sequence
<220> FEATURE:
<223> OTHER INFORMATION: A synthetic amino acid sequence

<400> SEQUENCE: 15

Met Asn Lys Pro Tyr Ser Ile Gly Leu Asp Ile Gly Thr Asn Ser Val
1               5               10              15

Gly Trp Ser Ile Ile Thr Asp Asp Tyr Lys Val Pro Ala Lys Lys Met
            20              25              30

Arg Val Leu Gly Asn Thr Asp Lys Glu Tyr Ile Lys Lys Asn Leu Ile
        35              40              45

Gly Ala Leu Leu Phe Asp Gly Gly Asn Thr Ala Ser Asp Arg Arg Leu
    50              55              60

Lys Arg Thr Ala Arg Arg Arg Tyr Thr Arg Arg Arg Asn Arg Ile Leu
65              70              75              80
```

-continued

Tyr Leu Gln Glu Ile Phe Ala Glu Glu Met Ser Lys Val Asp Asp Ser
                85                      90                      95

Phe Phe His Arg Leu Glu Asp Ser Phe Leu Val Glu Asp Asp Lys Arg
            100                     105                     110

Gly Ser Lys Tyr Pro Ile Phe Ala Thr Met Gln Glu Glu Lys Asp Tyr
            115                     120                     125

His Glu Lys Phe Pro Thr Ile Tyr His Leu Arg Lys Glu Leu Ala Asp
    130                     135                     140

Lys Lys Glu Lys Ala Asp Leu Arg Leu Phe Tyr Leu Ala Leu Ala His
145                     150                     155                     160

Ile Ile Lys Phe Arg Gly His Phe Leu Ile Glu Asp Asp Ser Phe Asp
                165                     170                     175

Val Arg Asn Thr Asp Ile Gln Arg Gln Tyr Gln Ala Phe Leu Glu Ile
            180                     185                     190

Phe Asp Thr Thr Phe Glu Asn Asn His Leu Leu Ser Gln Asn Ile Asp
            195                     200                     205

Val Glu Gly Ile Leu Thr Asp Lys Ile Ser Lys Ser Ala Lys Lys Asp
    210                     215                     220

Arg Ile Leu Ala Gln Tyr Pro Asn Gln Lys Ser Thr Gly Ile Phe Ala
225                     230                     235                     240

Glu Phe Leu Lys Leu Ile Val Gly Asn Gln Ala Asp Phe Lys Lys His
            245                     250                     255

Phe Asn Leu Glu Asp Lys Thr Pro Leu Gln Phe Ala Lys Asp Ser Tyr
            260                     265                     270

Asp Glu Asp Leu Glu Asn Leu Leu Gly Gln Ile Gly Asp Glu Phe Ala
            275                     280                     285

Asp Leu Phe Ser Val Ala Lys Lys Leu Tyr Asp Ser Val Leu Leu Ser
    290                     295                     300

Gly Ile Leu Thr Val Thr Asp Leu Ser Thr Lys Ala Pro Leu Ser Ala
305                     310                     315                     320

Ser Met Ile Gln Arg Tyr Asp Glu His Arg Glu Asp Leu Lys Gln Leu
                325                     330                     335

Lys Gln Phe Val Lys Ala Ser Leu Pro Glu Lys Tyr Gln Glu Ile Phe
            340                     345                     350

Thr Asp Ser Ser Lys Asp Gly Tyr Ala Gly Tyr Ile Glu Gly Lys Thr
            355                     360                     365

Asn Gln Gly Ala Phe Tyr Lys Tyr Leu Ser Lys Leu Leu Thr Lys Gln
    370                     375                     380

Glu Gly Ser Glu Tyr Phe Leu Glu Lys Ile Lys Asn Glu Asp Phe Leu
385                     390                     395                     400

Arg Lys Gln Arg Thr Phe Asp Asn Gly Ser Ile Pro His Gln Val His
            405                     410                     415

Leu Thr Glu Leu Lys Ala Ile Ile Arg Arg Gln Ser Glu Tyr Tyr Pro
            420                     425                     430

Phe Leu Lys Glu Asn Leu Asp Arg Ile Glu Lys Ile Leu Thr Phe Arg
            435                     440                     445

Ile Pro Tyr Tyr Val Gly Pro Leu Ala Arg Glu Lys Ser Asp Phe Ala
    450                     455                     460

Trp Met Thr Arg Lys Thr Asp Asp Ser Ile Arg Pro Trp Asn Phe Glu
465                     470                     475                     480

Glu Leu Val Asp Lys Glu Ala Ser Ala Glu Ala Phe Ile His Arg Met
            485                     490                     495

Thr Asn Asn Asp Leu Tyr Leu Pro Glu Glu Lys Val Leu Pro Lys His

-continued

```
                 500              505              510

Ser Leu Ile Tyr Glu Lys Phe Thr Val Tyr Asn Glu Leu Thr Lys Val
        515              520              525

Arg Tyr Lys Asn Glu Gln Gly Glu Thr Tyr Phe Phe Asp Ser Asn Ile
        530              535              540

Lys Gln Glu Ile Phe Asp Gly Val Phe Lys Glu His Arg Lys Val Ser
545              550              555              560

Lys Lys Lys Leu Leu Asp Phe Leu Ala Lys Glu Tyr Glu Glu Phe Arg
                 565              570              575

Ile Val Asp Val Ile Gly Leu Asp Lys Glu Asn Lys Ala Phe Asn Ala
                 580              585              590

Ser Leu Gly Thr Tyr His Asp Leu Lys Lys Ile Leu Asp Lys Asp Phe
        595              600              605

Leu Asp Asn Pro Asp Asn Glu Ser Ile Leu Glu Asp Ile Val Gln Thr
        610              615              620

Leu Thr Leu Phe Glu Asp Arg Glu Met Ile Lys Lys Arg Leu Glu Asn
625              630              635              640

Tyr Lys Asp Leu Phe Thr Glu Ser Gln Leu Lys Lys Leu Tyr Arg Arg
                 645              650              655

His Tyr Thr Gly Trp Gly Arg Leu Ser Ala Lys Leu Ile Asn Gly Ile
                 660              665              670

Arg Asp Lys Glu Ser Gln Lys Thr Ile Leu Asp Tyr Leu Ile Asp Asp
        675              680              685

Gly Lys Ser Asn Arg Asn Phe Met Gln Leu Ile His Asp Asp Gly Leu
        690              695              700

Ser Phe Lys Ser Ile Ile Ser Lys Ala Gln Ala Gly Ser His Ser Asp
705              710              715              720

Asn Leu Lys Glu Val Val Gly Glu Leu Ala Gly Ser Pro Ala Ile Lys
                 725              730              735

Lys Gly Ile Leu Gln Ser Leu Lys Ile Val Asp Glu Leu Val Lys Val
                 740              745              750

Met Gly Tyr Glu Pro Glu Gln Ile Val Val Glu Met Ala Arg Glu Asn
        755              760              765

Gln Thr Thr Asn Gln Gly Arg Arg Asn Ser Arg Gln Arg Tyr Lys Leu
        770              775              780

Leu Asp Asp Gly Val Lys Asn Leu Ala Ser Asp Leu Asn Gly Asn Ile
785              790              795              800

Leu Lys Glu Tyr Pro Thr Asp Asn Gln Ala Leu Gln Asn Glu Arg Leu
                 805              810              815

Phe Leu Tyr Tyr Leu Gln Asn Gly Arg Asp Met Tyr Thr Gly Lys Ala
                 820              825              830

Leu Asp Ile Asp Asn Leu Ser Gln Tyr Asp Ile Asp His Ile Ile Pro
        835              840              845

Gln Ala Phe Ile Lys Asp Asp Ser Ile Asp Asn Arg Val Leu Val Ser
        850              855              860

Ser Ala Lys Asn Arg Gly Lys Ser Asp Asp Val Pro Ser Leu Glu Ile
865              870              875              880

Val Lys Asp Cys Lys Val Phe Trp Lys Lys Leu Leu Asp Ala Lys Leu
                 885              890              895

Met Ser Gln Arg Lys Tyr Asp Asn Leu Thr Lys Ala Glu Arg Gly Gly
                 900              905              910

Leu Thr Ser Asp Asp Lys Ala Arg Phe Ile Gln Arg Gln Leu Val Glu
        915              920              925
```

-continued

```
Thr Arg Gln Ile Thr Lys His Val Ala Arg Ile Leu Asp Glu Arg Phe
    930             935             940

Asn Asn Glu Leu Asp Ser Lys Gly Arg Arg Ile Arg Lys Val Lys Ile
945             950             955             960

Val Thr Leu Lys Ser Asn Leu Val Ser Asn Phe Arg Lys Glu Phe Gly
            965             970             975

Phe Tyr Lys Ile Arg Glu Val Asn Asn Tyr His His Ala His Asp Ala
            980             985             990

Tyr Leu Asn Ala Val Val Ala Lys Ala Ile Leu Thr Lys Tyr Pro Gln
        995             1000            1005

Leu Glu Pro Glu Phe Val Tyr Gly Asp Tyr Pro Lys Tyr Asn Ser Tyr
    1010            1015            1020

Lys Thr Arg Lys Ser Ala Thr Glu Lys Leu Phe Phe Tyr Ser Asn Ile
1025            1030            1035            1040

Met Asn Phe Phe Lys Thr Lys Val Thr Leu Ala Asp Gly Thr Val Val
            1045            1050            1055

Val Lys Asp Asp Ile Glu Val Asn Asn Asp Thr Gly Glu Ile Val Trp
            1060            1065            1070

Asp Lys Lys Lys His Phe Ala Thr Val Arg Lys Val Leu Ser Tyr Pro
            1075            1080            1085

Gln Val Asn Ile Val Lys Lys Thr Glu Ile Gln Thr Gly Gly Phe Ser
    1090            1095            1100

Lys Glu Ser Ile Leu Ala His Gly Asn Ser Asp Lys Leu Ile Pro Arg
1105            1110            1115            1120

Lys Thr Lys Asp Ile Tyr Leu Asp Pro Lys Lys Tyr Gly Gly Phe Asp
            1125            1130            1135

Ser Pro Ile Val Ala Tyr Ser Val Leu Val Val Ala Asp Ile Lys Lys
            1140            1145            1150

Gly Lys Ala Gln Lys Leu Lys Thr Val Thr Glu Leu Leu Gly Ile Thr
            1155            1160            1165

Ile Met Glu Arg Ser Arg Phe Glu Lys Asn Pro Ser Ala Phe Leu Glu
    1170            1175            1180

Ser Lys Gly Tyr Leu Asn Ile Arg Asp Asp Lys Leu Met Ile Leu Pro
1185            1190            1195            1200

Lys Tyr Ser Leu Phe Glu Leu Glu Asn Gly Arg Arg Arg Leu Leu Ala
            1205            1210            1215

Ser Ala Gly Glu Leu Gln Lys Gly Asn Glu Leu Ala Leu Pro Thr Gln
            1220            1225            1230

Phe Met Lys Phe Leu Tyr Leu Ala Ser Arg Tyr Asn Glu Leu Lys Gly
        1235            1240            1245

Lys Pro Glu Glu Ile Glu Gln Lys Gln Glu Phe Val Val Gln His Val
    1250            1255            1260

Ser Tyr Phe Asp Asp Ile Leu Gln Ile Ile Asn Asp Phe Ser Asn Arg
1265            1270            1275            1280

Val Ile Leu Ala Asp Ala Asn Leu Glu Lys Ile Asn Lys Leu Tyr Gln
            1285            1290            1295

Asp Asn Lys Glu Asn Ile Ser Val Asp Glu Leu Ala Asn Asn Ile Ile
        1300            1305            1310

Asn Leu Phe Thr Phe Thr Ser Leu Gly Ala Pro Ala Ala Phe Lys Phe
        1315            1320            1325

Phe Asp Lys Ile Val Asp Arg Lys Arg Tyr Thr Ser Thr Lys Glu Val
    1330            1335            1340
```

-continued

```
Leu Asn Ser Thr Leu Ile His Gln Ser Ile Thr Gly Leu Tyr Glu Thr
1345                1350                1355                1360

Arg Ile Asp Leu Gly Lys Leu Gly Glu Asp
                1365                1370
```

METABOLICALLY STABILIZED DOUBLE STRANDED mRNA

CROSS-REFERENCE TO RELATED APPLICATIONS

This application is a division of U.S. patent application Ser. No. 16/090,468, filed on Oct. 1, 2018, which application is a U.S. National Stage Filing under 35 U.S.C. 371 from International Application No. PCT/US2017/025527, filed on Mar. 31, 2017, and published as WD 2017/173354 on Oct. 5, 2017, which application claims the benefit of the filing date of U.S. application Ser. No. 62/317,142, filed on Apr. 1, 2016, and U.S. application Ser. No. 62/335,186, filed on May 12, 2016, the disclosures of which are incorporated by reference herein.

STATEMENT OF GOVERNMENT RIGHTS

This invention was made with government support under contract GM097093, GM117785 and GM008365 awarded by the National Institutes of Health. The government has certain rights in the invention.

BACKGROUND

The development of a non-viral gene delivery system that efficiently expresses proteins in the liver has been a long-sought goal for over twenty-five years (Wu et al., 1988). Preclinical studies have demonstrated that protein expression in hepatocytes could lead to curative treatments for liver metabolic diseases as well as diseases in other organs (Wooddell et al., 2013; Chuah et al., 2013; Richard et al., 2009). Much of the effort in developing a non-viral gene delivery system for the liver has focused on packaging and targeting plasmid DNA (Pun et al., 2002; Lenter et al., 2004; Read et al., 2005). Despite much effort, systemic delivery of DNA formulations resulted in either negligible or very low gene transfer efficiency in liver hepatocytes (Hu et al., 2013). In contrast, hydrodynamic delivery of naked plasmid DNA to liver achieves expression efficiency equivalent to adenovirus or adeno-associated virus (AAV) (Liu et al., 1999). While hydrodynamic delivery is highly efficient because it overcomes the rate limiting step of delivery of DNA to the nucleus, it is also an invasive delivery method requiring both high volume and pressure (Al Dosari et al., 2005; Zhang et al., 2004; Andrianaivo et al., 2004; Hodges et al., 2003). Alternatively, the delivery of mRNA to the cytosol leading to translation, circumvents the need for delivery to the nucleus. Despite this major advantage, the rapid metabolism of mRNA by ubiquitous RNase remains a significant hurdle to achieving efficient expression of systemically delivered mRNA gene delivery systems (Sahin et al., 2014).

Since the earliest report demonstrating in vivo expression following intramuscularly (i.m.) dosed naked mRNA (Wolff et al., 1990), numerous studies have attempted to increase the stability and expression efficiency of mRNA formulations using cationic lipids (Deering et al., 2014; Phua et al., 2013; Schlake et al., 2012; Kariko et al, 2012; Malone et al., 1989). Intratracheal high pressure spraying of an mRNA Megafectin™ lipoplex resulted in transfection of the lung (Kormann et al., 2011), whereas regeneration following myocardial infarction was achieved by intracardial injection of RNAiMAX™ mRNA (Zangi et al., 2013). Stemfect™ mRNA delivered nasally resulted in tumor vaccination (Phua et al., 2014). Alternatively, systemically delivered Stemfect™ mRNA produced low level expression in the spleen (Phua et al., 2013). While these studies demonstrate that mRNA lipoplexes possess improved in vivo gene transfer over naked mRNA, their efficiency in vivo is still very low due to relatively weak ionic binding of cationic lipids to mRNA. A mannosylated histidinylated lipoplex dosed systemically resulted in expression in spleen macrophages which primed a tumor vaccine response (Perche et al., 2011).

In an attempt to further improve mRNA stability, nanoparticle delivery systems have been developed and tested in vitro (Avci-Adali et al., 2014; Cheng et al., 2012; Debus et al., 2010) and in vivo (Perche et al., 2011; Wang et al., 2013; Uchida et al., 2013). Systemic delivery of targeted stealth mRNA lipoplexes in vivo led to transfection efficiency similar to DNA formulations in solid tumor (Wang et al., 2013). Intrathecally dosed mRNA polyplex nanomicelles produced measurable expression in the cerebrospinal fluid (Uchida et al., 2013). Notably, none of the mRNA cationic lipid or nanoparticle formulations reported to date were able to transfect liver.

There have been only two reports of successful liver transfection with mRNA (McCaffrey et al., 2002; Wilber et al., 2006). The expression of mRNA in the liver was first achieved by McCaffrey et al. (2002) who measured luciferase expression by bioluminescence imaging (BLI) in mice following hydrodynamic (HD)-dosing of 50 μg of naked mRNA to detect low level expression ($10^6$ photons/sec/cm²/steradian). The transient expression in the liver was only detectable at 3 hours and required the co-administration of 30 μg of decoy RNA and 400 units of RNase inhibitor. In an attempt to improve transfection efficiency, Wilber et al. (2006) refined the mRNA by inserting 5' and 3' *Xenopus laevis* □-globin untranslated regions (UTRs) flanking luciferase to increase mRNA cellular half-life (Malone et al., 1989). HD-dosing of 50 □g of UTR mRNA resulted in a 15-fold increase in the expression efficiency at 3 hours relative to mRNA lacking UTRs (Wilber et al., 2006) but failed to significantly extend the expression. Co-administration of decoy mRNA and RNase inhibitors significantly improved efficiency but failed to extend peak expression past 12 hours. While these reports demonstrate the feasibility of expressing proteins in the liver when HD-dosing mRNA, the efficiencies reported are far below that achievable with plasmid DNA due to mRNA's susceptibility to metabolism during delivery.

SUMMARY

As shown herein, double stranded (ds) mRNA is much more metabolically stable than single-stranded (ss) mRNA and so ds mRNA formulations as described herein, can be dosed intravenously and circulate in the blood. ds mRNA is also as efficiently translated into protein as single-stranded mRNA. Thus, ds mRNA that includes single-stranded mRNA may be employed in targeted gene delivery system, e.g., systemic delivery, to express therapeutic proteins in animals, e.g., humans. Persistent expression is achieved by self-amplifying mRNA constructs designed to replicate mRNA in the cytosol and extend its expression.

In particular, as described below, the expression efficiency in liver following hydrodynamic delivery of in vitro transcribed ds mRNA was improved using an exemplary codon-optimized mRNA luciferase construct with flanking 3' and 5' human β-globin untranslated regions (UTR mRNA) over an un-optimized mRNA without β-globin UTRs.

In one embodiment, the disclosure provides isolated double stranded (ds) mRNA encoding a protein of interest, which ds mRNA is highly stable to degradation, e.g., after treatment with RNase or incubation in serum. At least one strand of the ds mRNA has a 5' cap, a start codon, and a polyA sequence, and this strand encodes a protein. The two strands of the ds mRNA are hydrogen bonded (Watson Crick) over at least 10 nucleotides and up to the full length of the shortest strand, if the strands are of different lengths. For example, the two strands of the ds mRNA are hydrogen bonded over at least 25, 50, 100, 200, 500, 1000, 2000 or more, e.g., 10,000 nucleotides (or any integer between 25 and 10,000), or over at least 50%, 60%, 70%, 80%, 85%, 90%, 95%, 98% or more of the length of at least one strand. In one embodiment, at least one strand may include one or more non-natural nucleotides, e.g., a nucleotide that has a non-natural sugar, a non-natural nucleotide base, a non-phosphodiester bond between nucleotides, or any combination thereof. In one embodiment, at least one of the strands may be formed using one or more of 2'-fluoro-2'deoxycytidine-5'-triphosphate, 5-iodocytidine-5'-triphosphate, 5-methylcytidine-5;-triphosphate, 2'-O-methylcytidine-5'-triphosphate, 2'-amino-2'-deoxycytidine-5'-triphosphate, 2'-amino-2'-deoxycytidine-5'-triphosphate, 2'-azido-2'-deoxycytidine-5'-triphosphate, aracytidine-5'-triphosphate, 2-thiocytidine-5'-triphosphate, 6-azacytidine-5'-triphosphate, 5-bromocytidine-5'-triphosphate, 3'-O-methylcytidine-5'-triphosphate, 5-aminoallylcytidine-5'-triphosphate, pseudoisocytidine-5'-triphosphate, N$^4$-methylcytidine-5'-triphosphate, 5-carboxycytidine-5'-triphosphate, 5-formylcytidine-5'-triphosphate, 5-hydroxymethylcytidine-5'-triphosphate, 5-hydroxycytidine-5'-triphosphate, 5-methoxycytidine-5'-triphosphate, thienocytidine-5'-triphosphate, cytidine-5'-triphosphate, 3'-deoxycytidine-5'-triphosphate, biotin-16-aminoallylcytidine-5'-triphosphate, cyanine 3-aminoallylcytidine-5'-triphosphate, cyanine 5-aminoallylcytidine-5'-triphosphate or cytidine-5'-O-(1-thiotriphosphate). In one embodiment, at least one of the strands is formed using one or more of 2'-fluoro-2'-deoxyuridine-5'-triphosphate, 5-iodouridine-5'-triphosphate, 2'-O-methyluridine-5'-triphosphate, pseudouridine-5'-triphosphate, 5-methyluridine-5'-triphosphate, 4-thiouridine-5'-triphosphate, 2'-amino-2'-deoxyuridine-5'-triphosphate, 2'-azido-2'-5'-triphosphate, 2-thiouridine-5'-triphosphate, arauridine-5'-triphosphate, 5,6-dihydrouridine-5'-triphosphate, 6-azauridine-5'-triphosphate, 2'-O-methylpseudouridine-5'-triphosphate, 2'-O-methyl-5-methyluridine-5'-triphosphate, 5-bromouridine-5'-triphosphate, 3'-O-methyluridine-5'-triphosphate, 5-aminoallyluridine-5'-triphosphate, N$^1$-methylpseudouridine-5'-triphosphate, 5,6-dihydro-5-methyluridine-5'-triphosphate, 5-hydroxymethyluridine-5'-triphosphate, 5-formyluridine-5'-triphosphate, 5-carboxyuridine-5'-triphosphate, 5-hydroxyuridine-5'-triphosphate, 5-methoxyuridine-5'-triphosphate, thienouridine-5'-triphosphate, 5-carboxymethylesteruridine-5'-triphosphate, uridine-5'-triphosphate, 3'-deoxy-5-methyluridine-5'-triphosphate, 3'-deoxyuridine-5'-triphosphate, biotin-16-aminoallyluridine-5'-triphosphate, desthiobiotin-16-aminoallyl-uridine-5'-triphosphate, cyanine 3-aminoallyluridine-5'-triphosphate, cyanine 7-aminoallyluridine-5'-triphosphate or uridine-5'-O-(1-thiotriphosphate). In one embodiment, at least one of the strands is formed using one or more of 5-aminoallyl-CTP, 2-amino-ATP, 5-Br-UTP, 5-carboxy-CTP, 5-carboxy-UTP, 5-carboxymethyest-UTP, 7-deaza-ATP, 5-formyl-CTP, 5-formyl-UTP, 5-hydroxy-CTP, 5-hydroxy-UTP, 5-hydroxymethyl-CTP, 5-hydroxymethyl-UTP, 5-iodo-UTP, 5-methoxy-CTP, 5-methoxy-UTP, N6-methyl-amino-ATP, N6-methyl-ATP, 5-methyl-CTP, pseudo-UTP, thieno-CTP, thieno-GTP, 1-thio-ATP or 2-thio-UTP. In one embodiment, one of the strands includes 5-formyl cytidine or pseudouridine. In one embodiment, at least 5%, 10%, 20%, 30%, 40%, 50% 60%, 70%, 80%, 90% or more of the nucleotides are non-natural nucleotides, and in one embodiment, the strands are hydrogen bonded over at least 5%, 10%, 20%, 30%, 40%, 50%, 60%, 70%, 80%, 90%, or more of the length of the strands.

Further provided is a method to prevent, inhibit or treat a disorder in a mammal associated with an absence or deficiency in a protein or in a mammal in need of increased amounts of a protein. The method includes systemically administering to the mammal an effective amount of a composition comprising one or more distinct ds mRNA as described above. In one embodiment, the composition is employed to express human factor VIII (HFVIII) in liver hepatocytes for treating hemophilia A. In one embodiment, the composition may be employed to systemically deliver CRISPR Cas9 or other gene editing systems.

Also provided are methods of making a ds mRNA encoding a protein of interest. In one embodiment, a strand of mRNA having a 5' cap, a start codon, a polyA sequence and an open reading frame for the protein and a strand of RNA that has sequence complementarity with the mRNA over at least 10 nucleotides are provided. The mRNA and the RNA with sequence complementarity are allowed to hydrogen bond, thereby providing the ds mRNA. In one embodiment, the strands are provided by transcription of one or more vectors, e.g. a plasmid vector. In one embodiment, the strands are provided by transcription of a single vector that includes an open reading frame for the protein that is flanked by a first promoter positioned to express the strand of mRNA and a second promoter positioned to express the strand of RNA with sequence complementarity. In one embodiment, at least one of the strands includes one or more non-natural nucleotides or nucleotide modifications. In one embodiment, the one or more nucleotide modifications are introduced post-synthesis of at least one of the strands. In one embodiment, the one or more non-natural nucleotides are incorporated during synthesis of at least one of the strands. In one embodiment, the strands are hydrogen bonded over at least 90% of the length of the strands. In one embodiment, the strands are hydrogen bonded over the entire length of the strands. In one embodiment, wherein the strands are not the same length. For example, when hybridized, the 3' end of the RNA with sequence complementarity overhands the 5' end of the strand of mRNA, or the 3' end of the RNA with sequence complementarity is recessed relative to the 5' end of the strand of mRNA. In one embodiment, the strands are the same length. In one embodiment, at least one of the strands is synthesized in an in vitro transcription reaction. In one embodiment, at least one of the strands is synthesized in a cell.

Further provided is a method of using the ds mRNA, e.g., to express a protein of interest. In one embodiment, a composition comprising a ds mRNA encoding the protein of interest, wherein at least one strand of the ds mRNA has a 5' cap, a start codon, a polyA sequence and encodes the protein, wherein the two strands of the ds mRNA are hydrogen bonded over at least 10 nucleotides is provided and the composition is introduced to cells in an amount effective to express the protein. In one embodiment, the cells are in a mammal for example, the composition is systemically administered to the mammal. In one embodiment, the composition is locally administered to the mammal. In one embodiment, the protein is a therapeutic protein. In one embodiment, the protein is for cancer immunotherapy. In one embodiment, the protein is a cancer antigen. In one embodiment, the protein is a nuclease. In one embodiment, the protein is a microbial protein, for instance, one useful for immunization. In one embodiment, the composition further comprises a carrier protein. In one embodiment, the composition further comprises a synthetic polymer optionally in combination with a carrier protein. In one embodiment, the composition further comprises a liposome. In one embodiment, the ds mRNA forms a nanoparticle, e.g., optionally in combination with a carrier protein, lipid, such as a lipid bilayer surrounding the ds mRNA, or synthetic polymer. In one embodiment, the nanoparticle has a diameter of about 1 nm to about 500 nm, about 50 nm to about 250 nm, or about 100 nm to about 200 nm. In one embodiment, the ds mRNA forms a microparticle, e.g., optionally in combination with a carrier protein, lipid, such as a lipid bilayer surrounding the ds mRNA, or synthetic polymer. In one embodiment, the microparticle has a diameter of about 0.5 μm to about 500 μm, about 10 μm to about 30 μm, or about 20 μm to about 40 μm.

DETAILED DESCRIPTION

Figure 1:
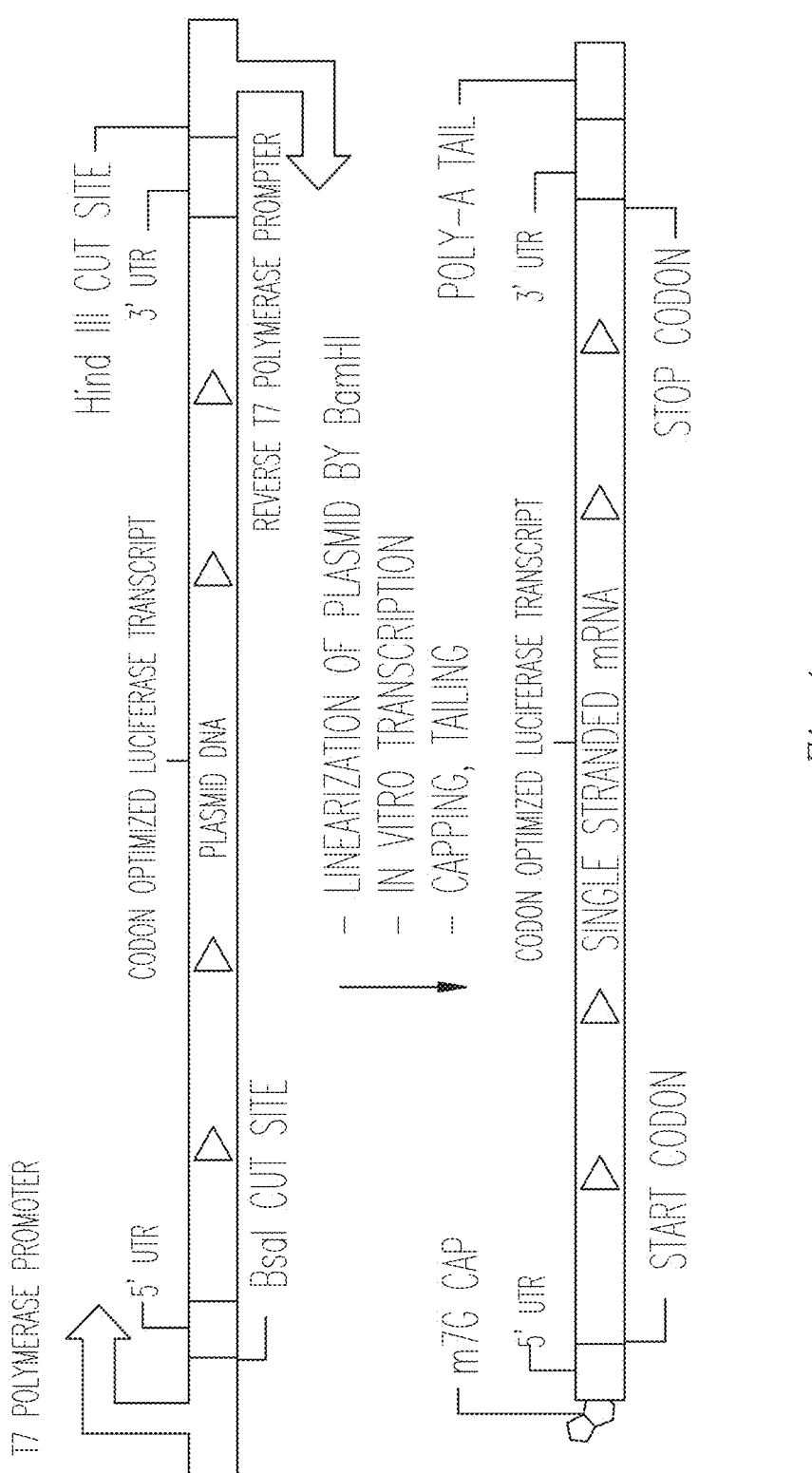
FIG. 1. Schematic of exemplary vector for single-stranded mRNA expression.

Various non-viral vectors can be used to deliver DNA, mRNA and short double-stranded RNA, including small interfering RNA (siRNA) and microRNA (miRNA) mimics. However, delivery of double stranded RNA (not mRNA, siRNA or miRNA) is highly toxic to cells due to triggering of apoptosis. Moreover, in order to be useful for gene therapy, the vectors need to avoid degradation by serum endonucleases and evade immune detection. They also need to avoid renal clearance from the blood and prevent non-specific interactions.

A stabilized ds mRNA containing composition is disclosed herein that is useful for prophylactic or therapeutic gene delivery. The compositions may be employed in methods to prevent, inhibit or treat a disorder or disease in a mammal, such as a canine, feline, bovine, porcine, equine, caprine, ovine, or human, which disorder or disease is amenable to treatment with one or more exogenously delivered genes. For example, the disorder or disease may be associated with a decreased amount of a gene product, the absence of a gene product, or the presence of an aberrant gene product, e.g., one having no activity, aberrant activity, reduced activity or increased activity relative to a mammal without the disorder or disease.

Exemplary Disorders or Diseases for Use with the Compositions

The compositions may be employed to prevent, inhibit or treat a variety of disorders or diseases associated with a deficiency in (or absence of) a protein or an aberrant protein (e.g., with low or no activity or excessive or unregulated activity) (see Table 1 for a list of monogenic disorders). Genes that may be employed include but are not limited to those that prevent, inhibit or treat hemophilia, anemia or other blood disorders, cancer, cardiovascular disease, lysosomal storage diseases, musculoskeletal diseases, neurodegenerative diseases, respiratory disease, and the like. Exemplary genes are shown in Table 2.

TABLE 1

| Monogenic disorders |
| --- |
| Adrenoleukodystrophy |
| α-1 antitrypsin deficiency |
| Becker muscular dystrophy |
| β-thalassaemia |
| Canavan disease |
| Chronic granulomatous disease |
| Cystic fibrosis |
| Duchenne muscular dystrophy |
| Fabry disease |
| Familial adenomatous polyposis |
| Familial hypercholesterolaemia |
| Fanconi anaemia |
| Galactosialidosis |
| Gaucher's disease |
| Gyrate atrophy |
| Haemophilia A and B |
| Hurler syndrome |
| Hunter syndrome |
| Huntington's chorea |
| Junctional epidermolysis bullosa |
| Late infantile neuronal ceroid lipofuscinosis |
| Leukocyte adherence defiency |
| Limb girdle muscular dystrophy |
| Lipoprotein lipase deficiency |
| Mucopolysaccharidosis type VII |
| Ornithine transcarbamylase deficiency |
| Pompe disease |
| Purine nucleoside phosphorylase deficiency |
| Recessive dystrophic epidermolysis bullosa |
| Sickle cell disease |
| Severe combined immunodeficiency |
| Tay Sachs disease |
| Wiskott-Aldrich syndrome |
| Cardiovascular disease |
| Anaemia of end stage renal disease |
| Angina pectoris (stable, unstable, refractory) |
| Coronary artery stenosis |
| Critical limb ischaemia |
| Heart failure |
| Intermittent claudication |
| Myocardial ischaemia |
| Peripheral vascular disease |
| Pulmonary hypertension |
| Venous ulcers |

TABLE 1-continued

Infectious disease

Adenovirus infection
Cytomegalovirus infection
Epstein-Barr virus
Hepatitis B and C
HIV/AIDS
Influenza
Japanese encephalitis
Malaria
Paediatric respiratory disease
Respiratory syncytial virus
Tetanus
Tuberculosis Cancer Gynaecological—breast, ovary, cervix, vulva
Nervous system—glioblastoma,
leptomeningeal carcinomatosis, glioma,
astrocytoma, neuroblastoma, retinoblastoma
Gastrointestinal—colon, colorectal, liver
metastases, post-hepatitis liver cancer,
pancreas, gall bladder
Genitourinary—prostate, renal, bladder,
anogenital neoplasia
Skin—melanoma (malignant/metastatic)
Head and neck—nasopharyngeal carcinoma,
squamous cell carcinoma, oesophageal
cancer
Lung—adenocarcinoma, small cell/nonsmall
cell, mesothelioma
Haematological—leukaemia, lymphoma,
multiple myeloma
Sarcoma
Germ cell
Li-Fraumeni syndrome
Thyroid Neurological diseases Alzheimer's disease
Amyotrophic lateral sclerosis
Carpal tunnel syndrome
Cubital tunnel syndrome
Diabetic neuropathy
Epilepsy
Multiple sclerosis
Myasthenia gravis
Parkinson's disease
Peripheral neuropathy
Pain Ocular diseases Age-related macular degeneration
Diabetic macular edema
Glaucoma
Retinitis pigmentosa
Superficial corneal opacity
Choroideraemia
Leber congenital amaurosis Inflammatory diseases Arthritis (rheumatoid, inflammatory,
degenerative)
Degenerative joint disease
Degenerative joint disease
Ulcerative colitis
Severe inflammatory disease of the rectum Other diseases Chronic renal disease
Erectile dysfunction
Detrusor overactivity
Parotid salivary hypofunction
Oral mucositis

TABLE 1-continued

Fractures
Type I diabetes
Diabetic ulcer/foot ulcer
Graft versus host disease/transplant patients

TABLE 2

| Gene Symbol | Protein name | Related Diseases |
|---|---|---|
| BCL2L11 | BCL2-like 11 (apoptosis facilitator) | Cancer, e.g. human T-cell acute lymphoblastic leukemia and lymphoma |
| BRCA1 | breast cancer 1, early onset | Cancer, e.g. breast cancer, pancreatic cancer |
| F8 | coagulation factor VIII, procoagulant component | Hemophilia |
| FLI1 | Friend leukemia virus integration 1 | cancer, e.g. Ewing's sarcoma, and myelodysplasia |
| FMR1 | fragile X mental retardation 1 | Fragile X syndrome and premature ovarian failure |
| FNDC5 | fibronectin type III domain containing 5 | Obesity, Type 2 Diabetes |
| GCK | glucokinase (hexokinase 4) | Obesity, Type 2 Diabetes, and Hyperinsulinemic hypoglycemia |
| GLP1R | glucagon-like peptide 1 receptor | Type 2 Diabetes |
| GRN | granulin | autoimmune, inflammatory, dementia/CNS disease, cancer, e.g. hepatic cancer |
| HAMP | hepcidin antimicrobial peptide | hemochromatosis, thalassemia |
| HPRT1 | hypoxanthine phosphoribosyl-transferase 1 | Lesch-Nyhan disease and HPRT-related gout |
| IDO1 | indoleamine 2,3-dioxygenase 1 | autoimmune and inflammatory diseases |
| IGF1 | insulin-like growth factor 1 (somatomedin C) | metabolic disease, delayed growth, cancer |
| IL10 | interleukin 10 | Autoimmune and inflammatory diseases, e.g. graft vs. host disease and rheumatoid arthritis |
| LDLR | low density lipoprotein receptor | dyslipidemias, atherosclerosis, and hypercholesterolemia |
| NANOG | Nanog homeobox | tissue regeneration |
| PTGS2 | prostaglandin-endoperoxide synthase 2 (prostaglandin G/H synthase and cyclooxygenase) | inflammation, cancer, infectious disease |
| RB1 | retinoblastoma 1 | cancer, e.g. bladder cancer, osteosarcoma, retinoblastoma, small cell lung cancer |
| SERPINF1 | serpin peptidase inhibitor; Glade F (alpha-2 antiplasmin, pigment epithelium derived factor), member 1 | cancer, choroidal neovascularization, cardiovascular disease, diabetes, and osteogenesis imperfecta |
| SIRT1 | sirtuin 1 | Metabolic disease, aging |

TABLE 2-continued

| Gene Symbol | Protein name | Related Diseases |
|---|---|---|
| SIRT6 | sirtuin 6 | antioxidative pathway, anti-NFKB |
| SMAD7 | SMAD family member 7 | Acute kidney injury (anti-TGPb), colorectal cancer |
| ST7 | suppression of tumorigenicity 7 | cancer, e.g. myeloid cancer, head and neck squamous cell carcinomas, breast cancer, colon carcinoma, and prostate cancer |
| STAT3 | signal transducer and activator of transcription 3 (acute-phase response factor) | tissue regeneration and Hyper-IgE recurrent infection syndrome |
| CFTR | Cystic fibrosis transmembrane conductance regulator | Cystic fibrosis (CF) and congenital bilateral absence of vas deferens (CBAVD) |
| PAH | Phenylalanine hydroxylase | Phenylketonuria (PKU) |
| CEP290 | Centrosomal protein of 290 kDa | Leber's congenital amaurosis (LCA), Bardet-Bledl syndrome (BBS). Joubert syndrome, Meckel syndrome, Sior-Loken syndrome |
| CD274 (also known as PD-L1) | cluster of differentiation 274 (also known as Programmed cell death 1 ligand 1) | Autoimmune disease, transplant rejection. allergies or asthma |
| ADIPOQ | adiponectin, C1Q and collagen domain containing (also known as adiponectin) | Obesity and obesity-linked diseases (e.g., hypertension, metabolic dysfunction, type 2 diabetes, atherosclerosis, and ischemic heart disease) |

Hemophilia-F8, F9, F11, VWF

Hemophilia is a group of hereditary genetic disorders that impair the body's ability to control blood clotting or coagulation, which is used to stop bleeding when a blood vessel is broken. Like most recessive sex-linked. X chromosome disorders, hemophilia is more likely to occur in males than females. For example, Hemophilia A (clotting factor VIII deficiency), the most common form of the disorder, is present in about 1 in 5,000-10,000 male births. Hemophilia 8 (factor IX deficiency) occurs in around 1 in about 20,000-34,000 male births. Hemophilia lowers blood plasma clotting factor levels of the coagulation factors, e.g. F8, needed for a normal clotting process. Thus when a blood vessel is injured, a temporary scab does form, but the missing coagulation factors prevent fibrin formation, which is necessary to maintain the blood clot F8, for example, encodes Factor VIII (FVIII), an essential blood clotting protein. Factor VIII participates in blood coagulation, it is a cofactor for factor IXa which, in the presence of $Ca^{+2}$ and phospholipids forms a complex that converts factor X to the activated form Xa.

Aspects of the invention disclosed herein provide methods and compositions that are useful for upregulating F8 for the treatment and/or prevention of diseases associated with reduced F8 expression or function such as hemophilia. Aspects of the invention disclosed herein provide methods and compositions that are useful for upregulating F9 for the treatment and/or prevention of diseases associated with reduced F9 expression or function such as hemophilia. Aspects of the invention disclosed herein provide methods and compositions that are useful for upregulating F11 for the treatment and/or prevention of diseases associated with reduced F11 expression or function such as hemophilia. Aspects of the invention disclosed herein provide methods and compositions that are useful for upregulating VWF for the treatment and/or prevention of diseases associated with reduced VFW expression or function such as Von Willebrand's Disease Thus, in one embodiment, the compositions may be employed to prevent, inhibit or treat hemophilia including but not limited to hemophilia A, characterized by low levels of or the absence of factor 8 (Also called FVIII or factor VIII deficiency), hemophilia B, characterized by low levels of or the absence of factor 9 (Also called FIX or factor IX deficiency), hemophilia C, characterized by low levels of or the absence of factor 11 (Also called FXI or factor XI deficiency), or Von Willebrands Disease, characterized by a deficiency of a blood clotting protein Von Willebrand factor.

Lysosomal Storage Diseases

In one embodiment, the compositions may be employed to prevent, inhibit or treat a lysosomal storage disease. Lysosomal storage diseases include, but are not limited to, mucopolysaccharidosis (MPS) diseases, for instance, mucopolysaccharidosis type I, e.g., Hurler syndrome and the variants Scheie syndrome and Hurler-Scheie syndrome (a deficiency in alpha-L-iduronidase); Hunter syndrome (a deficiency of iduronate-2-sulfatase); mucopolysaccharidosis type III, e.g., Sanfilippo syndrome (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV e.g., mucopolysaccharidosis type IV, e.g., Morquio syndrome (a deficiency of galactosamine-6-sulfate sulfatase or beta-galactosidase); mucopolysaccharidosis type VI, e.g., Maroteaux-Lamy syndrome (a deficiency of arylsulfatase B); mucopolysaccharidosis type II; mucopolysaccharidosis type III (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV (A or B; a deficiency of galactosamine-6-sulfatase and beta-galatacosidase); mucopolysaccharidosis type VI (a deficiency of arylsulfatase B); mucopolysaccharidosis type VII (a deficiency in beta-glucuronidase); mucopolysaccharidosis type VIII (a deficiency of glucosamine-6-sulfate sulfatase); mucopolysaccharidosis type IX (a deficiency of hyaluronidase); Tay-Sachs disease (a deficiency in alpha subunit of beta-hexosaminidase); Sandhoff disease (a deficiency in both alpha and beta subunit of beta-hexosaminidase); GM1 gangliosidosis (type I or type II); Fabry disease (a deficiency in alpha galactosidase); metachromatic leukodystrophy (a deficiency of aryl sulfatase A); Pompe disease (a deficiency of acid maltase); fucosidosis (a deficiency of fucosidase); alpha-mannosidosis (a deficiency of alpha-mannosidase); beta-mannosidosis (a deficiency of beta-mannosidase), ceroid lipofuscinosis, and Gaucher disease (types I, II and III; a deficiency in glucocerebrosidase), as well as disorders such as Hermansky-Pudlak syndrome; Amaurotic idiocy; Tangier disease; aspartylglucosaminuria; congenital disorder of glycosylation, type Ia; Chediak-Higashi syndrome; macular dystrophy, corneal, 1; cystinosis, nephropathic; Fanconi-Bickel syndrome; Farber lipogranulomatosis; fibromatosis; geleophysic dysplasia; glycogen storage disease I; glycogen storage disease Ib; glycogen storage disease Ic; glycogen storage disease III; glycogen storage disease IV; glycogen storage disease V; glycogen storage disease VI; glycogen storage disease VII; glycogen storage disease 0; immunoosseous dysplasia, Schimke type; lipidosis; lipase b; mucolipidosis II, including the variant form; mucolipidosis IV; neuraminidase deficiency with beta-galactosidase deficiency; mucolipidosis I; Niemann-Pick disease (a deficiency of sphingomyelinase); Niemann-Pick disease without sphingomyelinase deficiency (a deficiency of a npc1 gene encoding a cholesterol metabolizing enzyme); Refsum disease; Sea-blue histiocyte disease; Infantile sialic acid storage disorder; sialuria; multiple sulfatase deficiency; triglyceride storage disease with impaired long-chain fatty acid oxidation; Winchester disease; Wolman disease (a deficiency of cholesterol ester hydrolase); Deoxyribonuclease I-like 1 disorder; arylsulfatase E disorder; ATPase, H+ transporting, lysosomal, subunit 1 disorder; glycogen storage disease lib; Ras-associated protein rab9 disorder; chondrodysplasia punctata 1, X-linked recessive disorder; glycogen storage disease VIII; lysosome-associated membrane protein 2 disorder; Menkes syndrome; congenital disorder of glycosylation, type Ic; and sialuria.

Cancer-SERPINF1, BCL2L11, BRCA1, RB1, ST7

In one embodiment, the compositions may be employed to prevent, inhibit or treat cancer. Cancer is a broad group of various diseases, all involving unregulated cell growth. In cancer, cells divide and grow uncontrollably, forming malignant tumors, and invade nearby parts of the body. Several genes, many classified as tumor suppressors, are downregulated during cancer progression. e.g., SERPINF1, BCL2L11, BRCA1, RB1, and ST7, and have roles in inhibiting genomic instability, metabolic processes, immune response, cell growth/cell cycle progression, migration, and/or survival. These cellular processes are important for blocking tumor progression. SERPINF1 encodes an anti-angiogenic factor BCL2L11 encodes an apoptosis facilitator. BRCA1 encodes a RING finger protein involved in DNA damage repair. RB1 prevents excessive cell growth by inhibiting cell cycle progression until a cell is ready to divide. ST7 suppresses tumor growth in mouse models and is involved in regulation of genes involved in differentiation. Aspects of the invention disclosed herein provide methods and compositions that are useful for upregulating SERPINF1, BCL2L11, BRCA1, RB1, and ST7 for the treatment and/or prevention of diseases associated with reduced SERPINF1, BCL2L11, BRCA1, RB1, and ST7 expression or function such as cancer. For example, aspects of the invention disclosed herein provide methods and compositions that are useful for upregulating BCL2L11 for the treatment or prevention of human T-cell acute lymphoblastic leukemia and lymphoma. In another example, aspects of the invention disclosed herein provide methods and compositions that are useful for upregulating BRCA1 for the treatment or prevention of breast cancer or pancreatic cancer. In another example, aspects of the invention disclosed herein provide methods and compositions that are useful for upregulating RB1 for the treatment or prevention of bladder cancer, osteosarcoma, retinoblastoma, or small cell lung cancer. In another example, aspects of the invention disclosed herein provide methods and compositions that are useful for upregulating ST7 for the treatment or prevention of myeloid cancer, head and neck squamous cell carcinomas, breast cancer, colon carcinoma, or prostate cancer.

Examples of cancer include but are not limited to leukemias, lymphomas, myelomas, carcinomas, metastatic carcinomas, sarcomas, adenomas, nervous system cancers and genito-urinary cancers, in some embodiments, the cancer is adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas. Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer. Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors. Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinemia, malignant fibrous histiocytoma, medulloblastoma, melanoma. Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, or Wilms tumor.

Fragile X Syndrome—FMR1

Fragile X syndrome (FXS) (also known as Martin-Bell syndrome, or Escalante's syndrome) is a genetic syndrome that is the most common known single-gene cause of autism and the most common inherited cause of intellectual disability. It results in a spectrum of intellectual disability ranging from mild to severe as well as physical characteristics such as an elongated face, large or protruding ears, and larger testes (macroorchidism), behavioral characteristics such as stereotypical movements (e g hand-flapping), and social anxiety. Fragile X syndrome is associated with the expansion of the CGG trinucleotide repeat affecting the Fragile X mental retardation 1 (FMR1) gene on the X chromosome, resulting reduced expression of the X mental retardation protein (FMRP), which is required for normal neural development. Aspects of the invention disclosed herein provide methods and compositions that are useful for upregulating FMR1 for the treatment and/or prevention of diseases associated with reduced FMR1 expression or function such as Fragile X syndrome.

Premature Ovarian Failure—FMR1

Premature Ovarian Failure (POF), also known as premature ovarian insufficiency, primary ovarian insufficiency, premature menopause, or hypergonadotropic hypogonadism, is the loss of function of the ovaries before age 40. POF can be associated mutations in the Fragile X mental retardation 1 (FMR1) gene on the X chromosome, resulting reduced expression of the X mental retardation protein (FMRP). Aspects of the invention disclosed herein provide methods and compositions that are useful for upregulating FMR1 for the treatment and/or prevention of diseases associated with reduced FMR1 expression or function such as Premature Ovarian Failure.

Obesity-FNDC5, GCK, ADIPOQ

Obesity is a medical condition in which excess body fat has accumulated to the extent that it may have an adverse effect on health, leading to reduced life expectancy and/or increased health problems. A person is considered obese when his or her weight is 20% or more above normal weight. The most common measure of obesity is the body mass index or BMI. A person is considered overweight if his or her BMI is between 25 and 29.9; a person is considered obese if his or her BMI is over 30 Obesity increases the likelihood of various diseases, particularly heart disease, type 2 diabetes, obstructive sleep apnea, certain types of cancer, and osteoarthritis. Obesity is most commonly caused by a combination of excessive food energy intake, lack of physical activity, and genetic susceptibility. Overexpression of FNDC5, fibronectin type II containing 5, has been shown in animal models to reduce body weight in obese mice. GCK, glucokinase (hexokinase 4), phosphorylates glucose to produce glucose-6-phosphate, the first step in most glucose metabolism pathways. Mutations in the GCK gene have been found to be associated with obesity in humans. Aspects of the invention disclosed herein provide methods and compositions that are useful for upregulating FNDC5 for the treatment and/or prevention of diseases associated with reduced FNDC5 expression or function such as obesity. Aspects of the invention disclosed herein provide methods and compositions that are useful for upregulating GCK for the treatment and/or prevention of diseases associated with reduced GCK expression or function such as obesity.

Adiponectin, encoded by the ADIPOQ gene, is a hormone that regulates metabolism of lipids and glucose. Adipocytes found in adipose tissue secrete adiponectin into the bloodstream where it self-associates into larger structures by binding of multiple adiponectin trimers to form hexamers and dodecamers. Adiponectin levels are inversely related to the amount of body fat in an individual and positively associated with insulin sensitivity both in healthy subjects and in diabetic patients. Adiponectin has a variety of protective properties against obesity-linked complications, such as hypertension, metabolic dysfunction, type 2 diabetes, atherosclerosis, and ischemic heart disease through its anti-inflammatory and anti-atherogenic properties. Specifically with regard to type 2 diabetes, administration of adiponectin has been accompanied by a reduction in plasma glucose and an increase in insulin sensitivity. Aspects of the invention disclosed herein provide methods and compositions that are useful for upregulating ADIPOQ for the treatment and/or prevention of diseases associated with reduced ADIPOQ expression or function such as obesity or an obesity-linked disease or disorders such as hypertension, metabolic dysfunction, type 2 diabetes, atherosclerosis, and ischemic heart disease.

Type 2 Diabetes—FNDC5, GCK, GLP1R, SIRT1, ADIPOQ

Type 2 diabetes (also called Diabetes mellitus type 2 and formally known as adult-onset diabetes) a metabolic disorder that is characterized by high blood glucose in the context of insulin resistance and relative insulin deficiency. Type 2 diabetes makes up about 90% of cases of diabetes with the other 10% due primarily to diabetes mellitus type 1 and gestational diabetes. Obesity is thought to be the primary cause of type 2 diabetes in people who are genetically predisposed to the disease. The prevalence of diabetes has increased dramatically in the last 50 years. As of 2010 there were approximately 285 million people with the disease compared to around 30 million in 1985. Overexpression of FNDC5, fibronectin type II containing 5, has been shown in animal models to improve their insulin sensitivity GCK, glucokinase (hexokinase 4), phosphorylates glucose to produce glucose-6-phosphate, the first step in most glucose metabolism pathways. Mutations in the GCK gene are known to be associated with Type 2 Diabetes. Glucagon-like peptide 1 receptor (GLP1R) is known to be expressed in pancreatic beta cells. Activated GLP1R stimulates the adenylyl cyclase pathway which results in increased insulin synthesis and release of insulin SIRT1 (Sirtuin 1, also known as NAD-dependent deacetylase sirtuin-1) is an enzyme that deacetylates proteins that contribute to cellular regulation. Sirtuin 1 is downregulated in cells that have high insulin resistance and inducing its expression increases insulin sensitivity, suggesting the molecule is associated with improving insulin sensitivity. Aspects of the invention disclosed herein provide methods and compositions that are useful for upregulating FNDC5 for the treatment and/or prevention of diseases associated with reduced FNDC5 expression or function such as Type 2 Diabetes. Aspects of the invention disclosed herein provide methods and compositions that are useful for upregulating GCK for the treatment and/or prevention of diseases associated with reduced GCK expression or function such as Type 2 Diabetes. Aspects of the invention disclosed herein provide methods and compositions that are useful for upregulating GLP1R for the treatment and/or prevention of diseases associated with reduced GLP1R expression or function such as Type 2 Diabetes. Aspects of the invention disclosed herein provide methods and compositions that are useful for upregulating SIRT1 for the treatment and/or prevention of diseases associated with reduced SIRT1 expression or function such as Type 2 Diabetes. Aspects of the invention disclosed herein provide methods and compositions that are useful for upregulating ADIPOQ for the treatment and/or prevention of diseases associated with reduced ADIPOQ expression or function such as Type 2 Diabetes.

Metabolic Disease—IGF1, SIRT1

Inborn errors of metabolism comprise a large class of genetic diseases involving disorders of metabolism. The majority are due to defects of single genes that code for enzymes that facilitate conversion of various substances (substrates) into others (products). In most of the disorders, problems arise due to accumulation of substances which are toxic or interfere with normal function, or to the effects of reduced ability to synthesize essential compounds. Inborn errors of metabolism are now often referred to as congenital metabolic diseases or inherited metabolic diseases. IGF-1, Insulin growth factor-1, is a hormone similar in molecular structure to insulin. IGF-1 plays an important role in childhood growth and continues to have anabolic effects in adults. Reduced IGF-1 and mutations in the IGF-1 gene are associated with metabolic disease SIRT1 (Sirtuin 1, also known as NAD-dependent deacetylase sirtuin-1) is an enzyme that deacetylates proteins that contribute to cellular regulation. SIRT1 has been shown to de-acetylate and affect the activity of both members of the PGC1-alpha/ERR-alpha complex, which are essential metabolic regulatory transcription factors. Aspects of the invention disclosed herein provide methods and compositions that are useful for upregulating IGF-1 for the treatment and/or prevention of diseases associated with reduced IGF-1 expression or function such as metabolic disease. Aspects of the invention disclosed herein provide methods and compositions that are useful for upregulating SIRT1 for the treatment and/or prevention of diseases associated with reduced SIRT1 expression or function such as metabolic disease.

Aging/Senescence—SIRT1

Senescence is the state or process of aging. Cellular senescence is a phenomenon where isolated cells demonstrate a limited ability to divide in culture, while organismal senescence is the aging of organisms. After a period of near perfect renewal (in humans, between 20 and 35 years of age), organismal senescence/aging is characterised by the declining ability to respond to stress, increasing homeostatic imbalance and increased risk of disease. This currently irreversible series of changes inevitably ends in death. SIRT1 (Sirtuin 1, also known as NAD-dependent deacetylase sirtuin-1) is an enzyme that deacetylates proteins that contribute to cellular regulation. Mice overexpressing SIRT1 present lower levels of DNA damage, decreased expression of the ageing-associated gene p16Ink4a, a better general health and fewer spontaneous carcinomas and sarcomas. Aspects of the invention disclosed herein provide methods and compositions that are useful for upregulating SIRT1 for the treatment and/or prevention of biological processes associated with reduced SIRT1 expression or function such as aging.

Autoimmune—GRN, IDO1, CD274

Autoimmune diseases arise from an inappropriate immune response of the body against substances and tissues normally present in the body. In other words, the immune system mistakes some part of the body as a pathogen and attacks its own cells. Autoimmune diseases are classified by corresponding types of hypersensitivity: type II, type III, or type IV. Examples of autoimmune disease include, but are not limited to, Ankylosing Spondylitis. Autoimmune cardiomyopathy. Autoimmune hemolytic anemia, Autoimmune hepatitis. Autoimmune inner ear disease, immune lymphoproliferative syndrome, Autoimmune peripheral neuropathy. Autoimmune pancreatitis. Autoimmune polyendocrine syndrome, Autoimmune thrombocytopenic purpura. Celiac disease, Cold agglutinin disease, Contact dermatitis, Crohn's disease, Dermatomyositis, Diabetes mellitus type 1, Eosinophilic fasciitis, Gastrointestinal pemphigoid, Goodpasture's syndrome, Graves' disease, Guillain-Barré syndrome, Hashimoto's encephalopathy, Hashimoto's thyroiditis, Idiopathic thrombocytopenic purpura, Lupus erythematosus, Miller-Fisher syndrome, Myasthenia gravis, Pemphigus vulgaris, Pernicious anaemia, Polymyositis, Primary biliary cirrhosis, Psoriasis, Psoriatic arthritis, Relapsing polychondritis, Rheumatoid arthritis, Sjögren's syndrome, Temporal arteritis, Transverse myelitis, Ulcerative colitis, Undifferentiated connective tissue disease, Vasculitis, Vitiligo, and Wegener's granulomatosis, IDO1 encodes indoleamine 2,3-dioxygenase (IDO)—a heme enzyme that catalyzes the first and rate-limiting step in tryptophan catabolism to N-formylkynurenine. This enzyme acts on multiple tryptophan substrates including D-tryptophan. L-tryptophan, 5-hydroxytryptophan, tryptamine, and serotonin. This enzyme is thought to play a role in a variety of pathophysiological processes such as antimicrobial and antitumor defense, neuropathology, immunoregulation, and antioxidant activity, increased catabolism of tryptophan by IDO1 suppresses T cell responses in a variety of diseases or states, including autoimmune disorders. GRN encodes a precursor protein called Progranulin, which is then cleaved to form the secreted protein granulin. Granulin regulates cell division, survival, motility and migration. Granulin has roles in cancer, inflammation, host defense, cartilage development and degeneration, and neurological functions. Downregulation of GRN has been shown to increase the onset of autoimmune diseases like rheumatoid arthritis. Aspects of the invention disclosed herein provide methods and compositions that are useful for upregulating IDO1 for the treatment and/or prevention of diseases associated with reduced IDO1 expression or function such as autoimmune diseases. Aspects of the invention disclosed herein provide methods and compositions that are useful for upregulating GRN for the treatment and/or prevention of diseases associated with reduced GRN expression or function such as autoimmune diseases.

CD274 (also known as PDL1) is a transmembrane protein containing IgV-like and IgC-like extracellular domains expressed on immune cells and non-hematopoietic cells, and is a ligand for the programmed death receptor (PD-1) expressed on lymphocytes and macrophages. PD-1 and CD274 interactions are essential in maintaining the balance of T-cell activation, tolerance, and immune-mediated tissue damage. CD274 is involved in inhibiting the initial phase of activation and expansion of self-reactive T cells, and restricting self-reactive T-cell effector function and target organ injury. More specifically, activation of PD-1 by CD274 inhibits T-cell proliferation, cytokine production, and cytolytic function by blocking the induction of phosphatidylinositol-3-kinase (PI3K) activity and downstream activation of Akt.

Decreased expression of CD274 results in autoimmunity in animal models. For example, mice deficient for the CD274 receptor, PD-1, developed features of late onset lupus. In another instance, blockade of CD274 activity in a mouse model of Type 1 diabetes resulted in accelerated progression of diabetes. In yet another example, CD274 blockade in an animal model of multiple sclerosis resulted in accelerated disease onset and progression.

Increasing expression of CD274 offers a novel approach for treating diseases related to inappropriate or undesirable activation of the immune system, including in the context of translation rejection, allergies, asthma and autoimmune disorders. Aspects of the invention disclosed herein provide methods and compositions that are useful for upregulating CD274 for the treatment and/or prevention of diseases associated with reduced CD274 expression or function such as autoimmune disease, transplant rejection, allergies or asthma.

Inflammation (Chronic Inflammation)—GRN, IDO1, IL10

Inflammation is part of the complex biological response of vascular tissues to harmful stimuli, such as pathogens, damaged cells, or irritants. Inflammation is a protective attempt by the organism to remove the injurious stimuli and to initiate the healing process. However, chronic inflammation can also lead to a host of diseases, such as hay fever, periodontitis, atherosclerosis, and rheumatoid arthritis. Prolonged inflammation, known as chronic inflammation, leads to a progressive shift in the type of cells present at the site of inflammation and is characterized by simultaneous destruction and healing of the tissue from the inflammatory process. Inflammatory disorder include, but are not limited to: acne vulgaris, asthma, autoimmune diseases, celiac disease, chronic prostatitis, glomerulonephritis, inflammatory bowel diseases, pelvic inflammatory disease, reperfusion injury, rheumatoid arthritis, sarcoidosis, transplantation rejection (graft vs host disease), vasculitis and interstitial cystitis.

GRN encodes a precursor protein called Progranulin, which is then cleaved to form the secreted protein granulin. Granulin regulates cell division, survival, motility and migration. Granulin has roles in cancer, inflammation, host defense, cartilage development and degeneration, and neurological functions. GRN has been shown to alleviate inflammatory arthritis symptoms in mouse models. Indoleamine 2,3-dioxygenase 1 (IDO1; previously referred as IDO or INDO) is the main inducible and rate-limiting enzyme for the catabolism of the amino acid tryptophan through the kynurenine pathway. Increased catabolism of tryptophan by IDO1 suppresses T cell responses in a variety of diseases, such as allograft rejection.

Aspects of the invention disclosed herein provide methods and compositions that are useful for upregulating GRN for the treatment and/or prevention of diseases associated with reduced GRN expression or function such as chronic inflammation. Aspects of the invention disclosed herein provide methods and compositions that are useful for upregulating GRN for the treatment and/or prevention of diseases associated with reduced GRN expression or function such as rheumatoid arthritis. Aspects of the invention disclosed herein provide methods and compositions that are useful for upregulating IDO1 for the treatment and/or prevention of diseases associated with reduced IDO1 expression or function such as chronic inflammation. Aspects of the invention disclosed herein provide methods and compositions that are useful for upregulating IDO1 for the treatment and/or prevention of diseases associated with reduced IDO1 expression or function such as graft vs host disease.

IL-10 is capable of inhibiting synthesis of pro-inflammatory cytokines such as IFN-γ, IL-2, IL-3, TNFα and GM-CSF made by cells such as macrophages and regulatory T-cells. It also displays a potent ability to suppress the antigen-presentation capacity of antigen presenting cells. Treatment with IL-10 (e.g. as a recombinant protein given to patients) is currently in clinical trials for Crohn's disease. Genetic variation in the IL-10 pathway modulates severity of acute graft-versus-host disease. Mouse models of arthritis have been shown to have decreased levels of IL-10. Aspects of the invention disclosed herein provide methods and compositions that are useful for upregulating GRN for the treatment and/or prevention of diseases associated with reduced GRN expression or function such as chronic inflammation.

Aspects of the invention disclosed herein provide methods and compositions that are useful for upregulating IL-10 for the treatment and/or prevention of diseases associated with reduced IL-10 expression or function such as chronic inflammation. Aspects of the invention disclosed herein provide methods and compositions that are useful for upregulating IL-10 for the treatment and/or prevention of diseases associated with reduced IL-10 expression or function such as rheumatoid arthritis. Aspects of the invention disclosed herein provide methods and compositions that are useful for upregulating IL-10 for the treatment and/or prevention of diseases associated with reduced IL-10 expression or function such as graft vs host disease. Aspects of the invention disclosed herein provide methods and compositions that are useful for upregulating IL-10 for the treatment and/or prevention of diseases associated with reduced IL-10 expression or function such as Crohn's disease.

Infectious Disease—PTGS2

Infectious diseases, also known as transmissible diseases or communicable diseases comprise clinically evident illness (i.e., characteristic medical signs and/or symptoms of disease) resulting from the infection, presence and growth of pathogenic biological agents in an individual host organism. Infectious pathogens include some viruses, bacteria, fungi, protozoa, multicellular parasites, and aberrant proteins known as prions. A contagious disease is a subset of infectious disease that is especially infective or easily transmitted. Prostaglandin-endoperoxide synthase 2, also known as cyclooxygenase-2 or simply COX-2, is an enzyme that in humans is encoded by the PTGS2 gene. Prostaglandin endoperoxide H synthase, COX 2, converts arachidonic acid (AA) to prostaglandin endoperoxide H2. COX-2 is elevated during inflammation and infection. Aspects of the invention disclosed herein provide methods and compositions that are useful for upregulating PTGS2 for the treatment and/or prevention of diseases associated with reduced PTGS2 expression or function such as infectious disease.

CNS Disease—IGF1, GRN

Central nervous system (CNS) disease can affect either the spinal cord (myelopathy) or brain (encephalopathy), both of which are part of the central nervous system. CNS diseases include Encephalitis, Meningitis, Tropical spastic paraparesis, Arachnoid cysts, Amyotrophic lateral sclerosis, Huntington's disease, Alzheimer's disease, Dementia, Locked-in syndrome, Parkinson's disease, Tourette', and Multiple sclerosis, CNS diseases have a variety of causes including Trauma, Infections, Degeneration, Structural defects, Tumors, Autoimmune Disorders, and Stroke, Symptoms range from persistent headache, loss of feeling, memory loss, loss of muscle strength, tremors, seizures, slurred speech, and in some cases, death, IGF-1, insulin growth factor-1, is a hormone similar in molecular structure to insulin. IGF-I deficiency is associated with neurodegenerative disease and has been shown to improve survival of neurons both in vitro and in vivo. Aspects of the invention disclosed herein provide methods and compositions that are useful for upregulating IGF1 for the treatment and/or prevention of diseases associated with reduced IGF1 expression or function such as CNS disease.

GRN encodes a precursor protein called Progranulin, which is then cleaved to form the secreted protein granulin. Granulin regulates cell division, survival, motility and migration. Granulin has roles in cancer, inflammation, host defense, cartilage development and degeneration, and neurological functions. Mutations in granulin are associated with dementia. Aspects of the invention disclosed herein provide methods and compositions that are useful for upregulating GRN for the treatment and/or prevention of diseases associated with reduced GRN expression or function such as CNS disease.

Hemochromatosis—HAMP

Hemochromatosis is the abnormal accumulation of iron in parenchymal organs, leading to organ toxicity. This is the most common inherited liver disease in Caucasians and the most common autosomal recessive genetic disorder. HAMP (hepcidin antimicrobial peptide) encodes the protein hepcidin, which plays a major role in maintaining iron balance in the body. Hepcidin circulates in the blood and inhibits iron absorption by the small intestine when the body's supply of iron is too high. Hepcidin interacts primarily with other proteins in the intestines, liver, and certain white blood cells to adjust iron absorption and storage. At least eight mutations in the HAMP-gene have been identified that result in reduced levels of hepcidin and hemochromatosis. Aspects of the invention disclosed herein provide methods and compositions that are useful for upregulating HAMP for the treatment and/or prevention of diseases associated with reduced HAMP expression or function such as hemochromatosis.

Acute Kidney Injury—SMAD7

Acute kidney injury (AKI), previously called acute renal failure (ARF), is a rapid loss of kidney function, its causes are numerous and include low blood volume from any cause, exposure to substances harmful to the kidney, and obstruction of the urinary tract. AKI may lead to a number of complications, including metabolic acidosis, high potassium levels, uremia, changes in body fluid balance, and effects to other organ systems. SMAD7 (Mothers against decapentaplegic homolog 7) is a protein that, as its name describes, is a homolog of the *Drosophila* gene: "Mothers against decapentaplegic". It belongs to the SMAD family of proteins, which belong to the TGFβ superfamily of ligands. Like many other TGFβ family members, SMAD7 is involved in cell signalling. It is a TGFβ type 1 receptor antagonist. It blocks TGFβ1 and activin associated with the receptor, blocking access to SMAD2. It is an inhibitory SMAD (I-SMAD) and is enhanced by SMURF2. Upon TGF-β treatment. SMAD7 binds to discrete regions of Pellino-1 via distinct regions of the SMAD MH2 domains. The interaction block formation of the IRAK1-mediated IL-1R/TLR signaling complex therefore abrogates NF-r B activity, which subsequently causes reduced expression of pro-inflammatory genes. Overexpression of SMAD7 in the kidney using gene therapy inhibited renal fibrosis and inflammatory pathways. Aspects of the invention disclosed herein provide methods and compositions that are useful for upregulating SMAD7 for the treatment and/or prevention of diseases associated with reduced SMAD7 expression or function such as acute kidney injury.

Thalassemia—HAMP

Thalassemia is a group of inherited autosomal recessive blood disorders, resulting in a reduced rate of synthesis or no synthesis of one of the globin chains that make up hemoglobin. This can cause the formation of abnormal hemoglobin molecules or reduced numbers of hemoglobin, thus causing anemia, the characteristic presenting symptom of the thalassemias. HAMP (hepcidin antimicrobial peptide) encodes the protein hepcidin, which plays a major role in maintaining iron balance in the body. Hepcidin circulates in the blood and inhibits iron absorption by the small intestine when the body's supply of iron is too high. HAMP expression has been shown to be lower in patients with thalassemia and is associated with iron-overload (sometimes called hemochromatosis) in these patients. Aspects of the invention disclosed herein provide methods and compositions that are useful for upregulating HAMP for the treatment and/or prevention of diseases associated with reduced HAMP expression or function such as thalassemia.

Lesch-Nyhan Disease—HPRT1

Lesch-Nyhan syndrome (LNS), also known as Nyhan's syndrome, Kelley-Seegmiller syndrome and Juvenile gout, is a rare inherited disorder caused by a deficiency of the enzyme hypoxanthine-guanine phosphoribosyltransferase (HGPRT), produced by mutations in the HPRT gene located on the X chromosome. LNS affects about one in 380.000 live births. The HGPRT deficiency causes a build-up of uric acid in all body fluids. This results in both hyperuricemia and hyperuricosuria, associated with severe gout and kidney problems. Neurological signs include poor muscle control and moderate mental retardation. Aspects of the invention disclosed herein provide methods and compositions that are useful for upregulating HPRT for the treatment and/or prevention of diseases associated with reduced HPRT expression or function such as Lesch-Nyhan syndrome.

Delayed Growth—IGF-1

Delayed growth is poor or abnormally slow height or weight gains in a child typically younger than age 5, IGF-1, Insulin growth factor-1, is a hormone similar in molecular structure to insulin, IGF-1 plays an important role in childhood growth and continues to have anabolic effects in adults IGF1 deficiency has been shown to be associated with delayed growth and short stature in humans. Aspects of the invention disclosed herein provide methods and compositions that are useful for upregulating IGF1 for the treatment and/or prevention of diseases associated with reduced IGF1 expression or function such as delayed growth.

Dyslipidemias and Atherosclerosis—LDLR

Accumulation of lipids in the blood can cause a variety of conditions and diseases, e.g. dyslipidemia and atherosclerosis. Atherosclerosis in particular is the leading cause of death in industrialized societies, making prevention and treatment a high public health concern. Low-density lipoprotein (LDL) is a major transporter of fat molecules, e.g., cholesterol, in the blood stream that delivers fat molecules to cells. High-density lipoprotein (HDL) is another transporter of fat molecules that moves lipids, e.g. cholesterol, from cells to the liver. High levels of LDL are associated with health problems such as dyslipidemia and atherosclerosis, while HDL is protective against atherosclerosis and is involved in maintenance of cholesterol homeostasis.

Dyslipidemia generally describes a condition when an abnormal amount of lipids is present in the blood. Hyperlipidemia, which accounts for the majority of dyslipidemias, refers to an abnormally high amount of lipids in the blood. Hyperlipidemia is often associated with hormonal diseases such as diabetes, hypothyroidism, metabolic syndrome, and Cushing syndrome. Examples of common lipids in dyslipidemias include triglycerides, cholesterol and fat. Abnormal amounts lipids or lipoproteins in the blood can lead to atherosclerosis, heart disease, and stroke.

Atherosclerosic diseases, e.g. coronary artery disease (CAD) and myocardial infarction (MI), involve a thickening of artery walls caused by accumulation of fat in the blood, most commonly cholesterol. This thickening is thought to be the result of chronic inflammation of arteriole walls due to accumulation of LDLs in the vessel walls. LDL molecules can become oxidized once inside vessel walls, resulting in cell damage and recruitment of immune cells like macrophages to absorb the oxidized LDL. Once macrophages internalize oxidized LDL, they become saturated with cholesterol and are referred to as foam cells. Smooth muscle cells are then recruited and form a fibrous region. These processes eventually lead to formation of plaques that block arteries and can cause heart attack and stroke. HDL is capable of transporting cholesterol from foam cells to the liver, which aids in inhibition of inflammation and plaque formation.

The LDLR gene encodes the Low-Density Lipoprotein (LDL) Receptor, which is a mosaic protein of about 840 amino acids (after removal of signal peptide) that mediates the endocytosis of cholesterol-rich LDL it is a cell-surface receptor that recognizes the apoprotein B 100 which is embedded in the phospholipid outer layer of LDL particles. LDL receptor complexes are present in clathrin-coated pits (or buds) on the cell surface, which when bound to LDL-cholesterol via adaptin, are pinched off to form clathrin-coated vesicles inside the cell. This allows LDL-cholesterol to be bound and internalized in a process known as endocytosis. This occurs in all nucleated cells (not erythrocytes), but mainly in the liver which removes about 70% of LDL from the circulation. Aspects of the invention disclosed herein provide methods and compositions that are useful for upregulating LDLR for the treatment and/or prevention of diseases associated with reduced LDLR expression or function such as dyslipidemia or atherosclerosis.

Tissue Regeneration—NANOG

Regeneration is the process of renewal, restoration, and growth of cells and organs in response to disturbance or damage. Strategies for regeneration of tissue include the rearrangement of pre-existing tissue, the use of adult somatic stem cells and the dedifferentiation and/or transdifferentiation of cells, and more than one mode can operate in different tissues of the same animal. During the developmental process, genes are activated that serve to modify the properties of cells as they differentiate into different tissues. Development and regeneration involves the coordination and organization of populations cells into a blastema, which is a mound of stem cells from which regeneration begins. Dedifferentiation of cells means that they lose their tissue-specific characteristics as tissues remodel during the regeneration process. Transdifferentiation of cells occurs when they lose their tissue-specific characteristics during the regeneration process, and then re-differentiate to a different kind of cell. These strategies result in the re-establishment of appropriate tissue polarity, structure and form. NANOG is a transcription factor critically involved with self-renewal of undifferentiated embryonic stem cells through maintenance of pluripotency. Aspects of the invention disclosed herein provide methods and compositions that are useful for upregulating NANOG for tissue regeneration.

Oxidative Stress/Antioxidative Pathway—SIRT6

Cells are protected against oxidative stress by an interacting network of antioxidant enzymes. Oxidation reactions can produce superoxides or free radicals. In turn, these radicals can start chain reactions. When the chain reaction occurs in a cell, it can cause damage or death to the cell. Antioxidants terminate these chain reactions by removing free radical intermediates, and inhibit other oxidation reactions. The superoxide released by processes such as oxidative phosphorylation is first converted to hydrogen peroxide and then further reduced to give water. This detoxification pathway is the result of multiple enzymes, with superoxide dismutases catalysing the first step and then catalases and various peroxidases removing hydrogen peroxide. As oxidative stress appears to be an important part of many human diseases, the use of antioxidants in pharmacology is highly attractive. Mono-ADP-ribosyltransferase sirtuin-6 is an enzyme that in humans is encoded by the SIRT6 gene. Sirtuin-6 has been shown to have a protective role against metabolic damage caused by a high fat diet. SIRT6 deficiency is associated with metabolic defects that lead to oxidative stress. Aspects of the invention disclosed herein provide methods and compositions that are useful for upregulating SIRT6 for tissue regeneration. Aspects of the invention disclosed herein provide methods and compositions that are useful for upregulating SIRT6 for the treatment and/or prevention of diseases associated with reduced SIRT6 expression or function such as oxidative stress.

Choroidal Neovascularization—SERPINF1

Choroidal neovascularization (CNV) is the creation of new blood vessels in the choroid layer of the eye. This is a common symptom of the degenerative maculopathy wet AMD (age-related macular degeneration). Serpin F1 (SERPINF1), also known as Pigment epithelium-derived factor (PEDF), is a multifunctional secreted protein that has anti-angiogenic, anti-tumorigenic, and neurotrophic functions. The anti-angiogenic properties of SERPINF1 allow it to block new blood vessel formation. Aspects of the invention disclosed herein provide methods and compositions that are useful for upregulating SERPINF1 for the treatment and/or prevention of diseases associated with reduced SERPINF1 expression or function such as Choroidal neovascularization.

Cardiovascular Disease—SERPINF1

Cardiovascular disease is a class of diseases that involve the heart or blood vessels (arteries and veins). Cardiovascular diseases remain the biggest cause of deaths worldwide. Types of cardiovascular disease include, Coronary heart disease, Cardiomyopathy, Hypertensive heart disease, Heart failure, Corpulmonale, Cardiac dysrhythmias, Inflammatory heart disease, Valvular heart disease, Stroke and Peripheral arterial disease. Serpin F1 (SERPINF1), also known as Pigment epithelium-derived factor (PEDF), is a multifunctional secreted protein that has anti-angiogenic, anti-tumorigenic, and neurotrophic functions SERPINF1 has been shown to have a protective role in atherosclerosis, the main cause of coronary heart disease, myocardial infarction and heart failure due to its anti-inflammatory, antioxidant and antithrombotic effects in the vessel wall and platelets. Additionally SERPINF1 has strong antiangiogenic effects by inducing apoptosis in endothelial cells and by regulating the expression of other angiogenic factors. Aspects of the invention disclosed herein provide methods and compositions that are useful for upregulating SERPINF1 for the treatment and/or prevention of diseases associated with reduced SERPINF1 expression or function such as cardiovascular disease.

Hyperimmunoglobulin E Syndrome—STAT3

Loss-of-function mutations in the STAT3 gene result in Hyperimmunoglobulin E syndrome, associated with recurrent infections as well as disordered bone and tooth development.

Leber's Congenital Amaurosis (LCA), Bardet-Biedl Syndrome (BBS), Joubert Syndrome, Meckel Syndrome, Sior-Loken Syndrome-CEP290

Leber's congenital amaurosis (LCA) is a rare autosomal recessive eye disease resulting in a severe form of retinal dystrophy that is present from birth LCA results in slow or non-existent pupillary responses, involuntary eye movement, and severe loss of vision. LCA is thought to be caused by abnormal photoreceptor cell development or degeneration. Bardet-Biedl syndrome (BBS) is characterized by retinal dystrophy and retinitis pigmentosa. Other manifestations include polydactyly and renal abnormalities. Both LCA and BBS are associated with mutations in Centrosomal protein 290 kDA (CEP290).

CEP290 is a large coiled-coil protein found in the centrosome and cilia of cells. CEP290 modulates ciliary formation and is involved in trafficking ciliary proteins between the cell body and the cilium of a cell. Reduction or abolishment of CEP290 activity, results in retinal and photoreceptor degeneration. This generation is thought to be the result of defects in ciliogenesis is CEP290 is also associated with Joubert syndrome, Meckel syndrome, and Sior-Loken syndrome. Aspects of the invention disclosed herein provide methods and compositions that are useful for upregulating CEP290 for the treatment and/or prevention of diseases associated with reduced CEP290 expression or function such as Leber's congenital amaurosis (LCA), Bardet-Biedl syndrome (BBS), Joubert syndrome, Meckel syndrome, Sior-Loken syndrome.

Phenylketonuria—PAH

Phenylketonuria (PKU) is an autosomal recessive metabolic disease caused by elevated levels of Phenyalanine (Phe) in the blood. Phe is a large neutral amino acid (LNAA) that interacts with the LNAA transporter in order to cross the blood-brain barrier. When Phe is in excess in the blood, it saturates the LNAA transporter, prevent other essential LNAAs from crossing the blood-brain barrier. This results in depletion of these amino acids in the brain, leading to slowing of the development of the brain and Mental retardation PKU can be managed by strictly controlling and monitoring Phe levels in the diet in infants and children. However, if left untreated, severe mental retardation, irregular motor functions, and behavioral disorders result from Phe accumulation in the blood.

Phe accumulation in the blood is the result of mutations in the Phenylalanine hydroxylase (PAH) gene, which encodes phenylalanine hydroxylase protein. Phenylalanine hydroxylase is an enzyme that generates tyrosine through hydroxylation of the aromatic side-chain of Phe. Phenylalanine hydroxylase is the rate-limiting enzyme in the degradation of excess Phe. When phenylalanine hydroxylase levels are decreased or enzyme functionality is compromised, Phe begins to accumulate in the blood, resulting in PKU. Aspects of the invention disclosed herein provide methods and compositions that are useful for upregulating PAH for the treatment and/or prevention of diseases associated with reduced PAH expression or function such as PKU.

Congenital Bilateral Absence of Vas Deferens (CBAVD) and Cystic Fibrosis (CF)—CFTR CFTR is a cyclic-AMP activated ATP-gated anion channel that transports ions across cell membranes CFTR is predominantly found in epithelial cells in the lung, liver, pancreas, digestive tract, reproductive tract, and skin. A main function of CFTR is to move chloride and thiocyanate ions out of epithelial cells. In order to maintain electrical balance, sodium ions move with the chloride and thiocyanate ions, resulting in an increase of electrolytes outside of the cell. This increase results in movement of water out of the cell by osmosis, creating bodily fluids such as mucus, sweat, and digestive juices, depending on the organ. When CFTR activity is reduced or abolished, ion transport is affected, resulting in reduced water movement out of cells and abnormally viscous bodily fluids (e.g. sticky and viscous mucus, sweat, or digestives juices).

Mutations in CFTR are associated with congenital bilateral absence of vas deferens (CBAVD) and cystic fibrosis. Males with congenital bilateral absence of the vas deferens often have mutations that result in reduced CFTR activity. As a result of these mutations, the movement of water and salt into and out of cells is disrupted. This disturbance leads to the production of a large amount of thick mucus that blocks the developing vas deferens (a tube that carries sperm from the testes) and causes it to degenerate, resulting in infertility.

Cystic fibrosis (CF) is an autosomal recessive disease characterized by overly viscous secretions in the lungs, pancreas, liver, and intestine, in the lungs, difficulty breathing and frequent infection are common results of mucus build-up. Viscous secretions in the pancreas lead to scarring, fibrosis, and cyst formation which can subsequently lead to diabetes. Additionally, absorption of nutrients in the intestine is decreased due to a lack of digestive enzymes provided by the pancreas. Blockage of the intestine is also common due to thickening of the feces. Aspects of the invention disclosed herein provide methods and compositions that are useful for upregulating CFTR for the treatment and/or prevention of diseases associated with reduced CFTR expression or function such CBAVD or CF.

Exemplary Nucleotide Analogs

Each strand of the ds mRNA molecule can independently Include one or more nucleotide analogs, e.g., having modifications to the base, e.g., nucleobases including but not limited to 1,5-dimethyluracil, 1-methyluracil, 2-amino-6-hydroxyaminopurine, 2-aminopurine, 3-methyluracil, 5-(hydroxymethyl)cytosine, 5-bromouracil, 5-carboxycytosine, 5-fluoroorotic acid, 5-fluorouracil, 5-formylcytosine, 8-azaadenine, 8-azaguanine, M-hydroxyadenine, allopurinol, hypoxanthine, or thiouracil, modifications of the sugar group or modifications of the phosphate group. In one embodiment, at least one strand of the ds mRNA molecule includes, but is not limited to, 1-methyladenosine, 2-methylthio-$N^6$-hydroxynorvalylcarbamoyladenosine, 2-methyladenosine, 2-O-ribosylphosphate adenosine, $N^6$-methyl-$N^6$-threonylcarbamoyladenosine, $N^6$-acetyladenosine, $N^6$-glycinylcarbamoyladenosine, $N^6$-isopentenyladenosine, $N^6$-methyladenosine, $N^6$-threonylcarbamoyladenosine, $N^6$, $N^6$-dimethyladenosine, N $N^6$-(cis-hydroxyisopentenyl)adenosine, $N^6$-hydroxynorvalylcarbamoyladenosine, 1,2-O-dimethyladenosine, $N^6$,2-O-dimethyladenosine, 2-O-methyladenosine, $N^6$, $N^6$,O-2-trimethyladenosine, 2-methylthio-$N^6$-(cis-hydroxyisopentenyl) adenosine, 2-methylthio-$N^6$-methyladenosine, 2-methylthio-$N^6$-isopentenyladenosine, 2-methylthio-$N^6$-threonyl carbamoyladenosine, 2-thiocytidine, 3-methylcytidine, $N^4$-acetylcytidine, 5-formylcytidine, $N^4$-methylcytidine, 5-methylcytidine, 5-hydroxymethylcytidine, lysidine, $N^4$-acetyl-2-O-methylcytidine, 5-formyl-2-O-methylcytidine, 5,2-O-dimethylcytidine, 2-O-methylcytidine, $N^4$,2-O-dimethylcytidine, $N^4$, $N^4$,2-O-trimethylcytidine, 1-methylguanosine, $N^4$,7-dimethylguanosine, $N^4$-methylguanosine, 2-O-ribosylphosphate guanosine, 7-methylguanosine, under modified hydroxywybutosine, 7-aminomethyl-7-deazaguanosine, 7-cyano-7-deazaguanosine, $N^2$, $N^2$-dimethylguanosine, 4-demethylwyosine, epoxyqueuosine, hydroxywybutosine, isowyosine, $N^2$,7,2-O-trimethylguanosine, $N^2$,2-O-dimethylguanosine, 1,2-O-dimethylguanosine, 2-O-methylguanosine, $N^2$ $N^2$2,2-O-trimethylguanosine, N2,N2,7-trimethylguanosine, peroxywybutosine, galactosyl-queuosine, mannosyl-queuosine, queuosine, archaeosine, wybutosine, methylwyosine, wyosine, 2-thiouridine, 3-(3-amino-3-carboxypropyl)uridine, 3-methyluridine, 4-thiouridine, 5-methyl-2-thiouridine, 5-methylaminomethyluridine, 5-carboxymethyluridine, 5-carboxymethylaminomethyluridine, 5-hydroxyuridine, 5-methyluridine, 5-taurinomethyluridine, 5-carbamoylmethyluridine, 5-(carboxyhydroxymethyl)uridine methyl ester, dihydrouridine, 5-methyldihydrouridine, 5-methylaminomethyl-2-thiouridine, 5-(carboxyhydroxymethyl)uridine, 5-(isopentenylaminomethyl)uridine, 5-(isopentenylaminomethyl)-2-thiouridine, 3,2-O-dimethyluridine, 5-carboxymethylaminomethyl-2-O-methyluridine, 5-carbamoylmethyl-2-O-methyluridine, 5-methoxycarbonylmethyl-2-O-methyluridine, 5-(isopentenylaminomethyl)-2-O-methyluridine, 5,2-O-dimethyluridine, 2-O-methyluridine, 2-thio-2-O-methyluridine, uridine 5-oxyacetic acid, 5-methoxycarbonylmethyluridine, uridine 5-oxyacetic acid methyl ester, 5-methoxyuridine, 5-aminomethyl-2-thiouridine, 5-carboxymethylaminomethyl-2-thiouridine, 5-methylaminomethyl-2-selenouridine, 5-methoxycarbonylmethyl-2-thiouridine, 5-taurinomethyl-2-thiouridine, pseudouridine, 1-methyl-3-(3-amino-3-carboxypropyl)pseudouridine, 1-methylpseudouridine, 3-methylpseudouridine, 2-O-methylpseudouridine, inosine, 1-methylinosine, 1,2-O-dimethylinosine and 2-O-methyl-inosine, or any combination thereof.

In one embodiment, at least one strand of the ds mRNA molecule includes, but is not limited to, cytosine arabinoside or fludarabine. In one embodiment, at least one strand of the ds mRNA molecule includes, but is not limited to, cladrib-ine, acyclovir, 2',3'-dideoxyinosine; 9-β-D-ribofuranosylad-enine; .beta.-arabinofuranosylcytosine; arabinosylcytosine; 4-amino-5-fluoro-1-[(2R,5S)-2-(hydroxymethyl)-1,3-oxa-thiolan-5-yl]-1,2-dim hydropyrimidin-2-one; 2',3'-dideoxy-3'-thiacytidine; 2'-3'-dideoxycytidine; {(1S,4R)-4-[2-amino-8-(cyclopropylamino)-9H-purin-9-yl]cyclopent-2-en-1-yl}methanol; 2-Amino-9-[(1S,3R,4S)-4-hydroxy-3-(hydroxymethyl)-2-methylidenecyclopentyl]-6,9-dihydro-3H-purin-6-one; 2'-3'-didehydro-2'-3'-dideoxythymidine; 1-(2-deoxy-.beta.-L-erythro-pentofuranosyl)-5-methylpy-rimidine-2,4(1H,3H)-dione; 1-[(2R,4S,5S)-4-azido-5-(hy-droxymethyl)oxolan-2-yl]-5-methylpyrimidine-2,4-dione; 1-[(2R,4S,5R)-4-hydroxy-5-(hydroxymethyl)oxolan-2-yl]-5-iodo-1,2,3,4-tetrahydropyrimidine-2,4-dione; 1-[4-hy-droxy-5-(hydroxymethyl)oxolan-2-yl]-5-(trifluoromethyl)pyrimidine-2,4-dione; 5-Fluoro-2'-deoxycytidine; 5-Fluoro-deoxycytidine; Floxuridine (5-Fluoro-1-[4-hydroxy-5-(hy-droxymethyl)tetrahydrofuran-2-yl]-1H-pyrimidine-2,4-di-one); 4-amino-1-(2-deoxy-2,2-difluoro-β-D-erythro-pentofuranosyl)pyrmidin-2(1H)-one; or 2',2'-difluoro-2'-deoxycytidine; (8R)-3-(2-deoxy-β-D-erythro-pentofuranosyl)-3,4,7,8-tetrahydroimidazo[4,5-d][1,3]diazepin-8-ol, or any combination thereof.

In one embodiment, a strand of the ds mRNA may include analogs such as 2'-O-methyl-substituted RNA, locked nucleic acid (LNA) or BNA (Bridged Nucleic Acid), mor-pholino, or peptide nucleic acid (PNA), or any combination thereof.

In one embodiment, nucleotide analogs include phospho-rothioate nucleotides or deazapurine nucleotides and other nucleotide analogs.

In one embodiment, one or more strands of the ds mRNA molecule can independently include a modified nucleotide selected from a deoxyribonucleotide, a dideoxyribonucle-otide, an acyclonucleotide, a 3'-deoxyadenosine (cordyce-pin), a 3'-azido-3'-deoxythymidine (AZT), a 2',3'-dide-oxyinosine (ddI), a 2',3'-dideoxy-3'-thiacytidine (3TC), a 2',3'-didehydro-2',3'-dideoxythymidine (d4T), a monophos-phate nucleotide of 3'-azido-3'-deoxythymidine (AZT), a 2',3'-dideoxy-3'-thiacytidine (3TC) and a monophosphate nucleotide of 2',3'-didehydro-2',3'-dideoxythymidine (d4T), a 4-thiouracil, a 5-bromouracil, a 5-iodouracil, a 5-(3-ami-noallyl)-uracil, a 2'-O-alkyl ribonucleotide, a 2'-O-methyl ribonucleotide, a 2'-amino ribonucleotide, a 2'-fluoro ribo-nucleotide, or a locked nucleic acid; or any combination thereof.

In one embodiment, the nucleotide modification includes 2' modifications, e.g., 2' F on pyrimidines or 2' H or 2' OMe on purines.

In one embodiment, the nucleotide modification includes a phosphate backbone modification selected from a phos-phonate, a phosphorothioate, a phosphotriester; a mor-pholino nucleic acid; or a peptide nucleic acid (PNA).

Sugar modifications in the strand(s) include, but are not limited to, replacing the heteroatoms at the 2' and 3' carbons with hydrogen, another heteroatom or an alkyl group; replacing the H's at the 2' carbon with a heteroatom or alkyl group; replacing the 2' and 3' carbons with a heteroatom, most commonly S or O; removing the 2' and/or 3' carbons to generate acyclic sugars; replacing the 4'-OH with N, S, or an alkyl group; adding alkyl groups to the 4'-carbon; replac-ing the 5'-hydroxyl with N or a phosphonate, or intercon-version of both the sugar stereochemistry (D vs. L) and anomeric configuration (α vs. β).

The invention will be described by the following non-limiting examples.

Example 1

A codon-optimized firefly luciferase gene with 5' and 3' human beta globin untranslated regions (UTRs) was installed onto the pcDNA3.1 plasmid (FIG. 1). This firefly luciferase gene was transcribed by in vitro transcription. A 5' 7-methyl guanosine cap and 3' poly-A tail was added by enzymatic synthesis. The 5' m'G cap, 3' poly-A tail, both UTRs, and codon optimization have been shown to dramati-cally increased luciferase expression in vivo.

Figure 2:
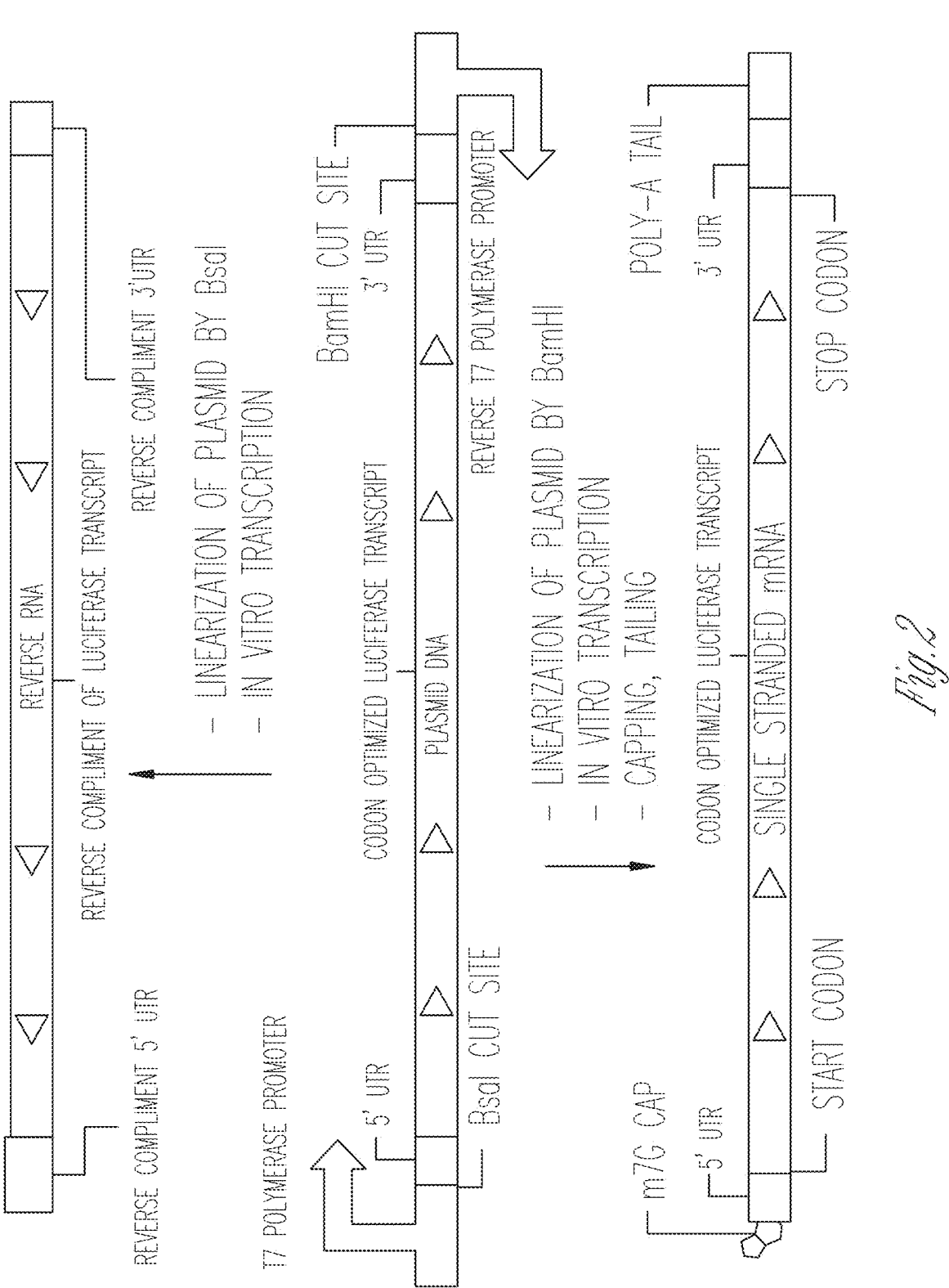
FIG. 2. Schematic of use of exemplary vector for reverse RNA expression.

Double stranded mRNA was produced by constructing a plasmid with two T7 promoters in reverse orientations, both flanking the codon-optimized luciferase gene. Sense and antisense strands were produced in separate reactions by cutting the plasmid in different positions (FIG. 2). The sense strand was capped with 7-methyl guanosine and poly-A tailed. The sense and antisense strands were annealed by heating to 65° C. with slow cooling. Uridine was replaced with pseudouridine to reduce the immune response.

Figure 3:
FIG. 3. Resistance of ssRNA and ds mRNA to RNase.

The relative stability of ss mRNA and ds mRNA when challenged by digestion with RNase A was compared. ss mRNA and ds mRNA were incubated with increasing amounts of RNase A for 10 minutes at 37° C. and products were immediately separated on an agarose gel. The rela-tively stability of ds mRNA versus ss mRNA approaches infinity when both are digested with 10 μg of RNAse A (FIG. 3).

Figure 4:
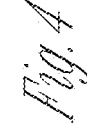
FIG. 4. Resistance of ssRNA and ds mRNA to serum nucleases.

Serum nucleases degrade RNA. The relative stability of ds mRNA versus ss mRNA was compared when digested with increasing amounts of mouse serum. ss mRNA and ds mRNA were incubated with 0.0008% to 8% vol/vol ratio of mouse serum for 10 minutes at 37° C. then analyzed on an agarose gel (FIG. 4). ds mRNA is shown to be highly stable compared to ss mRNA. The relative increase in stability approaches infinity by comparing ss mRNA and ds mRNA digested with 0.8% serum.

Figure 5:
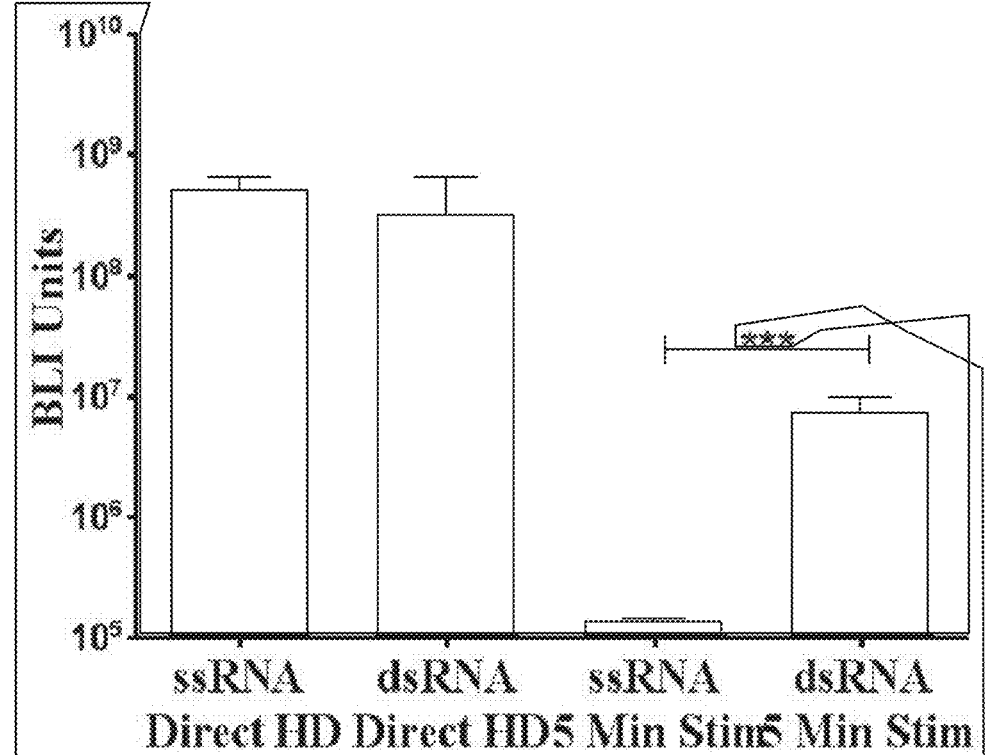
FIG. 5. Stability in vivo of ds mRNA-PEG-peptide complexes.

The relative translation of ss mRNA and ds mRNA into protein was compared by administering a 1 □g dose of each into mice via the tail vein by direct hydrodynamic injection. The expression of luciferase in the liver was determined at times ranging from 4 to 72 hours by serially measuring the light produced from the liver by in vivo bioluminescence imaging following i.p. dosing of luciferin (FIG. 5). The level of luciferase expression for both ss mRNA and ds mRNA peaked at 4 hours and was maintained for 24 hours before declining over 48 and 72 hours. The results demonstrate that ds mRNA and ss mRNA produce equivalent expression of luciferase at times ranging from 4-72 hours.

Example 2

Double stranded mRNA may be produced by constructing a plasmid with two T7 promoters in reverse orientations, both flanking a gene of interest, e.g., one useful for appli-cations including but not limited to cancer immunotherapy, such as Melan-A, tyrosinase, gp100, MAGE-A1, MAGE-A3 or surivin, infectious disease, e.g., a viral or bacterial protein, protein replacement or augmentation, e.g., EPO, IL-10, VEGF-A, surface B protein or Foxp3, somatic reprogramming, or genome editing. Sense and antisense strands may be produced in separate reactions by cutting the plasmid in different positions. The sequences may be codon optimized, e.g., to improve translation or to decrease endonuclease activity, for instance, one or more uridine residues may be replaced with pseudouridine to reduce the immune response, or natural residues may be replaced with other analogs such as 2-thiouridine, 5-methyluridine, 5-methylcytidine or N6-methyl adenosine, or any combination thereof. The sense strand may be capped with 7-methyl guanosine or with cap analogs, and poly-A tailed. The sense and antisense strands are annealed by heating to 65° C. with slow cooling.

For example, for cancer immunotherapy, a double stranded mRNA having a sense strand that encodes a mammalian melanoma antigen recognized by T-cells (MART-1), e.g., where the sense strand has nucleic acid sequences with at least 90%, 92%, 95%, 97%, 98%, 99% or 100% nucleic acid sequence identity to coding sequences in SEQ ID NO:1 or a nucleic acid sequence that encodes a protein with at least 80% amino acid sequence identity to a protein encoded by SEQ ID NO:1; a double stranded mRNA having a sense strand that encodes a mammalian tyrosinase, e.g., where the sense strand has nucleic acid sequences with at least 90%, 92%, 95%, 97%, 98%, 99% or 100% nucleic acid sequence identity to coding sequences in SEQ ID NO:2 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:2; a double stranded mRNA having a sense strand that encodes a mammalian melanoma antigen, e.g., where the sense strand has nucleic acid sequences with at least 90%, 92%, 95%, 97%, 98%, 99% or 100% nucleic acid sequence identity to coding sequences in SEQ ID NO:3 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:3; or a double stranded mRNA having a sense strand that encodes a mammalian survivin, e.g., where the sense strand has nucleic acid sequences with at least 90%, 92%, 95%, 97%, 98%, 99% or 100% nucleic acid sequence identity to coding sequences in SEQ ID NO:4 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:4, may be employed.

(SEQ ID NO: 1)

```
AGCAGACAGAGGACTCTCATTAAGGAAGGTGTCCTGTGCCCTGACCCTACAAGATGCCAA

GAGAAGATGCTCACTTCATCTATGGTTACCCCAAGAAGGGGCACGGCCACTCTTACACCA

CGGCTGAAGAGGCCGCTGGGATCGGCATCCTGACAGTGATCCTGGGAGTCTTACTGCTCA

TCGGCTGTTGGTATTGTAGAAGACGAAATGGATACAGAGCCTTGATGGATAAAAGTOTTC

ATGTTGGCACTCAATGTGCCTTAACAAGAAGATGCCCACAAGAAGGGTTTGATCATCGGG

ACAGCAAAGTGTCTCTTCAAGAGAAAAACTGTGAACCTGTGGTTCCCAATGCTCCACCTG

CTTATGAGAAACTCTCTGCAGAACAGTCACCACCACCTTATTCACCTTAAGAGCCAGCGA

GACACCTGAGACATGCTGAAATTATTTCTCTCACACTTTTGCTTGAATTTAATACAGACA

TCTAATGTTCTCCTTTGGAATGGTGTAGGAAAAATGCAAGCCATCTCTAATAATAAGTCA

GTGTTAAAATTTTAGTAGGTCCGCTAGCAGTACTAATCATGTGAGGAAATGATGAGAAAT

ATTAAATTGGGAAAACTCCATCAATAAATGTTGCAATGCATGATACTATCTGTGCCAGAG

GTAATGTTAGTAAATCCATGGTGTTATTTTCTGAGAGACAGAATTCAAGTGGGTATTCTG

GGGCCATCCAATTTCTCTTTACTTGAAATTTGGCTAATAACAAACTAGTCAGGTTTTCGA

ACCTTGACCGACATGAACTGTACACAGAATTGTTCCAGTACTATGGAGTGCTCACAAAGG

ATACTTTTACAGGTTAAGACAAAGGGTTGACTGGCCTATTTATCTGATCAAGAACATGTC

AGCAATGTCTCTTTGTGCTCTAAAATTCTATTATACTACAATAATATATTGTAAAGATCC

TATAGCTCTTTTTTTTTGAGATGGAGTTTCGCTTTTGTTGCCCAGGCTGGAGTGCAATGG

CGCGATCTTGGCTCACCATAACCTCCGCCTCCCAGGTTCAAGCAATTCTCCTGCCTTAGC

CTCCTGAGTAGCTGGGATTACAGGCGTGCGCCACTATGCCTGACTAATTTTGTAGTTTTA

GTAGAGACGGGGTTTCTCCATGTTGGTCAGGCTGGTCTCAAACTCCTGACCTCAGGTGAT

CTGCCCGCCTCAGCCTCCCAAAGTGCTGGAATTACAGGCGTGAGCCACCACGCCTGGCTG

GATCCTATATCTTAGGTAAGACATATAACGCAGTCTAATTACATTTCACTTCAAGGCTCA

ATGCTATTCTAACTAATGACAAGTATTTTCTACTAAACCAGAAATTGGTAGAAGGATTTA
```

-continued

AATAAGTAAAAGCTACTATGTACTGCCTTAGTGCTGATGCCTGTGTACTGCCTTAAATGT

ACCTATGGCAATTTAGCTCTCTTGGGTTCCCAAATCCCTCTCACAAGAATGTGCAGAAGA

AATCATAAAGGATCAGAGATTCTG (SEQ ID NO: 2)

TATTGAGTTCTTCAAACATTGTAGCCTCTTTATGGTCTCTGAGAAATAACTACCTTAAAC

CCATAATCTTTAATACTTCCTAAACTTTCTTAATAAGAGAAGCTCTATTCCTGACACTAC

CTCTCATTTGCAAGGTCAAATCATCATTAGTTTTGTAGTCTATTAACTGGGTTTGCTTAG

GTCAGGCATTATTATTACTAACCTTATTGTTAATATTCTAACCATAAGAATTAAACTATT

AATGGTGAATAGAGTTTTTCACTTTAACATAGGCCTATCCCACTGGTGGGATACGAGCCA

ATTCGAAAGAAAAGTCAGTCATGTGCTTTTCAGAGGATGAAAGCTTAAGATAAAGACTAA

AAGTGTTTGATGCTGGAGGTGGGAGTGGTATTATATAGGTCTCAGCCAAGACATGTGATA

ATCACTGTAGTAGTAGCTGGAAAGAGAAATCTGTGACTCCAATTAGCCAGTTCCTGCAGA

CCTTGTGAGGACTAGAGGAAGAATGCTCCTGGCTGTTTTGTACTGCCTGCTGTGGAGTTT

CCAGACCTCCGCTGGCCATTTCCCTAGAGCCTGTGTCTCCTCTAAGAACCTGATGGAGAA

GGAATGCTGTCCACCGTGGAGCGGGGACAGGAGTCCCTGTGGCCAGCTTTCAGGCAGAGG

TTCCTGTCAGAATATCCTTCTGTCCAATGCACCACTTGGGCCTCAATTTCCCTTCACAGG

GGTGGATGACCGGGAGTCGTGGCCTTCCGTCTTTTATAATAGGACCTGCCAGTGCTCTGG

CAACTTCATGGGATTCAACTGTGGAAACTGCAAGTTTGGCTTTTGGGGACCAAACTGCAC

AGAGAGACGACTCTTGGTGAGAAGAAACATCTTCGATTTGAGTGCCCCAGAGAAGGACAA

ATTTTTTGCCTACCTCACTTTAGCAAAGCATACCATCAGCTCAGACTATGTCATCCCCAT

AGGGACCTATGGCCAAATGAAAAATGGATCAACACCCATGTTTAACGACATCAATATTTA

TGACCTCTTTGTCTGGATGCATTATTATGTGTCAATGGATGCACTGCTTGGGGGATCTGA

AATCTGGAGAGACATTGATTTTGCCCATGAAGCACCAGCTTTTCTGCCTTGGCATAGACT

CTTCTTGTTGCGGTGGGAACAAGAAATCCAGAAGCTGACAGGAGATGAAAACTTCACTAT

TCCATATTGGGACTGGCGGGATGCAGAAAAGTGTGACATTTGCACAGATGAGTACATGGG

AGGTCAGCACCCCACAAATCCTAACTTACTCAGCCCAGCATCATTCTTCTCCTCTTGGCA

GATTGTCTGTAGCCGATTGGAGGAGTACAACAGCCATCAGTCTTTATGCAATGGAACGCC

CGAGGGACCTTTACGGCGTAATCCTGGAAACCATGACAAATCCAGAACCCCAAGGCTCCC

CTCTTCAGCTGATGTAGAATTTTGCCTGAGTTTGACCCAATATGAATCTGGTTCCATGGA

TAAAGCTGCCAATTTCAGCTTTAGAAATACACTGGAAGGATTTGCTAGTCCACTTACTGG

GATAGCGGATGCCTCTCAAAGCAGCATGCACAATGCCTTGCACATCTATATGAATGGAAC

AATGTCCCAGGTACAGGGATCTGCCAACGATCCTATCTTCCTTCTTCACCATGCATTTGT

TGACAGTATTTTTGAGCAGTGGCTCCGAAGGCACCGTCCTCTTCAAGAAGTTTATCCAGA

AGCCAATGCACCCATTGGACATAACCGGGAATCCTACATGGTTCCTTTTATACCACTGTA

CAGAAATGGTGATTTCTTTATTTCATCCAAAGATCTGGGCTATGACTATAGCTATCTACA

AGATTCAGACCCAGACTCTTTTCAAGACTACATTAAGTCCTATTTGGAACAAGCGAGTCG

GATCTGGTCATGGCTCCTTGGGGCGGCGATGGTAGGGGCCGTCCTCACTGCCCTGCTGGC

AGGGCTTGTGAGCTTGCTGTGTCGTCACAAGAGAAAGCAGCTTCCTGAAGAAAAGCAGCC

ACTCCTCATGGAGAAAGAGGATTACCACAGCTTGTATCAGAGCCATTTATAAAAGGCTTA

GGCAATAGAGTAGGGCCAAAAAGCCTGACCTCACTCTAACTCAAAGTAATGTCCAGGTTC

CCAGAGAATATCTGCTGGTATTTTTCTGTAAAGACCATTTGCAAAATTGTAACCTAATAC

-continued

AAAGTGTAGCCTTCTTCCAACTCAGGTAGAACACACCTGTCTTTGTCTTGCTGTTTTCAC

TCAGCCCTTTTAACATTTTCCCCTAAGCCCATATGTCTAAGGAAAGGATGCTATTTGGTA

ATGAGGAACTGTTATTTGTATGTGAATTAAAGTGCTCTTATTTT (SEQ ID NO: 3)

CCCACACTCCCGCCTGTTGCCCTGACCAGAGTCATCATGCCTCTTGAGCAGAGGAGTCAG

CACTGCAAGCCTGAAGAAGGCCTTGAGGCCCGAGGAGAGGCCCTGGGCCTGGTGGGTGCG

CAGGCTCCTGCTACTGAGGAGCAGGAGGCTGCCTCCTCCTCTTCTACTCTAGTTGAAGTC

ACCCTGGGGGAGGTGCCTGCTGCCGAGTCACCAGATCCTCCCCAGAGTCCTCAGGGAGCC

TCCAGCCTCCCCACTACCATGAACTACCCTCTCTGGAGCCAATCCTATGAGGACTCCAGC

AACCAAGAAGAGGAGGGGCCAAGCACCTTCCCTGACCTGGAGTCCGAGTTCCAAGCAGCA

CTCAGTAGGAAGGTGGCCGAGTTGGTTCATTTTCTGCTCCTCAAGTATCGAGCCAGGGAG

CCGGTCACAAAGGCAGAAATGCTGGGGAGTGTCGTCGGAAATTGGCAGTATTTCTTTCCT

GTGATCTTCAGCAAAGCTTTCAGTTCCTTGCAGCTGGTCTTTGGCATCGAGCTGATGGAA

GTGGACCCCATCGGCCACTTGTACATCTTTGCCACCTGCCTGGGCCTCTCCTACGATGGC

CTGCTGGGTGACAATCAGATCATGCCCAAGGCAGGCCTCCTGATAATCGTCCTGGCCATA

ATCGCAAGAGAGGGCGACTGTGCCCCTGAGGAGAAAATCTGGGAGGAGCTGAGTGTGTTA

GAGGTGTTTGAGGGGAGGGAAGACAGTATCTTGGGGGATCCCAAGAAGCTGCTCACCCAA

CATTTCGTGCAGGAAAACTACCTGGAGTACCGGCAGGTCCCCGGCAGTGATCCTGCATGT

TATGAATTCCTGTGGGGTCCAAGGGCCCTCGTTGAAACCAGCTATGTGAAAGTCCTGCAC

CATATGGTAAAGATCAGTGGAGGACCTCACATTTCCTACCCACCCCTGCATGAGTGGGTT

TTGAGAGAGGGGGAAGAGTGAGTCTGAGCACGAGTTGCAGCCAGGGCCAGTGGGAGGGGG

TCTGGGCCAGTGCACCTTCCGGGGCCGCATCCCTTAGTTTCCACTGCCTCCTGTGACGTG

AGGCCCATTCTTCACTCTTTGAAGCGAGCAGTCAGCATTCTTAGTAGTGGGTTTCTGTTC

TGTTGGATGACTTTGAGATTATTCTTTGTTTCCTGTTGGAGTTGTTCAAATGTTCCTTTT

AACGGATGGTTGAATGAGCGTCAGCATCCAGGTTTATGAATGACAGTAGTCACACATAGT

GCTGTTTATATAGTTTAGGAGTAAGGGTCTTGTTTTTTACTCAAATTGGGAAATCCATTC

CATTTTGTGAATTGTGACATAATAATAGCAGTGGTAAAAGTATTTGCTTAAAATTGTGAG

CGAATTAGCAATAACATACATGAGATAACTCAAGAAATCAAAAGATAGTTGATTCTTGCC

TTGTACCTCAATCTATTCTGTAAAATTAAACAAATATGCAAACCAGGATTTCCTTGACTT

CTTTGAGAATGCAAGCGAAATTAAATCTGAATAAATAATTCTTCCTCTTCAAAAAAAAAA

AAAAAAAAAAAAAGGCCACA (SEQ ID NO: 4)

GTTGGCAGAGGTGGCGGCGGCGGCATGGGTGCCCCGACGTTGCCCCCTGCCTGGCAGCCC

TTTCTCAAGGACCACCGCATCTCTACATTCAAGAACTGGCCCTTCTTGGAGGGCTGCGCC

TGCACCCCGGAGCGGATGGCCGAGGCTGGCTTCATCCACTGCCCCACTGAGAACGAGCCA

GACTTGGCCCAGTGTTTCTTCTGCTTCAAGGAGCTGGAAGGCTGGGAGCCAGATGACGAC

CCCATAGAGGAACATAAAAAGCATTCGTCCGGTTGCGCTTTCCTTTCTGTCAAGAAGCAG

TTTGAAGAATTAACCCTTGGTGAATTTTTGAAACTGGACAGAGAAAGAGCCAAGAACAAA

ATTGCAAAGGAAACCAACAATAAGAAGAAAGAATTTGAGGAAACTGCGAAGAAAGTGCGC

CGTGCCATCGAGCAGCTGGCTGCCATGGATTGAGGCCTCTGGCCGGAGCTGCCTGGTCCC

AGAGTGGCTGCACCACTTCCAGGGTTTATTCCCTGGTGCCACCAGCCTTCCTGTGGGCCC

CTTAGCAATGTCTTAGGAAAGGAGATCAACATTTTCAAATTAGATGTTTCAACTGTGCTC

-continued

TTGTTTTGTCTTGAAAGTGGCACCAGAGGTGCTTCTGCCTGTGCAGCGGGTGCTGCTGGT

AACAGTGGCTGCTTCTCTCTCTCTCTCTCTTTTTTGGGGGCTCATTTTTGCTGTTTTGAT

TCCCGGGCTTACCAGGTGAGAAGTGAGGGAGGAAGAAGGCAGTGTCCCTTTTGCTAGAGC

TGACAGCTTTGTTCGCGTGGGCAGAGCCTTCCACAGTGAATGTGTCTGGACCTCATGTTG

TTGAGGCTGTCACAGTCCTGAGTGTGGACTTGGCAGGTGCCTGTTGAATCTGAGCTGCAG

GTTCCTTATCTGTCACACCTGTGCCTCCTCAGAGGACAGTTTTTTTGTTGTTGTGTTTTT

TTGTTTTTTTTTTTTTGGTAGATGCATGACTTGTGTGTGATGAGAGAATGGAGACAGAGT

CCCTGGCTCCTCTACTGTTTAACAACATGGCTTTCTTATTTTGTTTGAATTGTTAATTCA

CAGAATAGCACAAACTACAATTAAAACTAAGCACAAAGCCATTCTAAGTCATTGGGGAAA

CGGGGTGAACTTCAGGTGGATGAGGAGACAGAATAGAGTGATAGGAAGCGTCTGGCAGAT

ACTCCTTTTGCCACTGCTGTGTGATTAGACAGGCCCAGTGAGCCGCGGGGCACATGCTGG

CCGCTCCTCCCTCAGAAAAAGGCAGTGGCCTAAATCCTTTTTAAATGACTTGGCTCGATG

CTGTGGGGGACTGGCTGGGCTGCTGCAGGCCGTGTGTCTGTCAGCCCAACCTTCACATCT

GTCACGTTCTCCACACGGGGGAGAGACGCAGTCCGCCCAGGTCCCCGCTTTCTTTGGAGG

CAGCAGCTCCCGCAGGGCTGAAGTCTGGCGTAAGATGATGGATTTGATTCGCCCTCCTCC

CTGTCATAGAGCTGCAGGGTGGATTGTTACAGCTTCGCTGGAAACCTCTGGAGGTCATCT

CGGCTGTTCCTGAGAAATAAAAAGCCTGTCATTTCAAACACAAAAAAAAAAAAAAAAAAA

AAAAAAAAA

Thus, in one embodiment, double stranded RNA having a sense strand that encodes a cancer antigen, e.g., one that is useful to prevent, inhibit or treat cancer or otherwise enhance the immune system, may be introduced to a host organism, e.g., a mammal such as a human, optionally with an adjuvant. The double stranded RNA may be directly administered, or by administration of two plasmids, each encoding one of the strands, optionally in conjunction with positively charged polymers such as PEI, cationic polypeptides, e.g., protamine, or dendrimers, or using a delivery vehicle, e.g., a microparticle or nanoparticle, for instance, a liposome. For instance, double stranded RNA having a sense strand that encodes tyrosinase or survivin may be used to treat a melanoma patient, e.g., as an immunotherapeutic.

For infectious disease, a double stranded mRNA having a sense strand that encodes a microbial protein including a protein or glycoprotein specific for a viral pathogen, a bacterial pathogen, an algal pathogen, or a fungal pathogen, for example, a respiratory syncytial virus (RSV) fusion protein, e.g., where the sense strand has nucleic acid sequences with at least 90%, 92%, 95%, 97%, 98%, 99% or 100% nucleic acid sequence identity to coding sequences in SEQ ID NO:5 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:5, may be employed as a vaccine.

(SEQ ID NO: 5)

ATGGAGCTGCTGATCCACAGGTTAAGTGCAATCTTCCTAACTCTTGCTATTAATGCATTG

TACCTCACCTCAAGTCAGAACATAACTGAGGAGTTTTACCAATCGACATGTAGTGCAGTT

AGCAGAGGTTATTTTAGTGCTTTAAGAACAGGTTGGTATACCAGTGTCATAACAATAGAA

TTAAGTAATATAAAAGAAACCAAATGCAATGGAACTGACACTAAAGTAAAACTTATAAAA

CAAGAATTAGATAAGTATAAGAATGCAGTGACAGAATTACAGCTACTTATGCAAAACACA

CCAGCTGCCAACAACCGGGCCAGAAGAGAAGCACCACAGTATATGAACTATACAATCAAT

ACCACTAAAAACCTAAATGTATCAATAAGCAAGAAGAGGAAACGAAGATTTCTGGGCTTC

TTGTTAGGTGTAGGATCTGCAATAGCAAGTGGTATAGCTGTATCCAAAGTTCTACACCTT

GAAGGAGAAGTGAACAAGATCAAAAATGCTTTGTTATCTACAAACAAAGCTGTAGTCAGT

CTATCAAATGGGGTCAGTGTTTTAACCAGCAAAGTGTTAGATCTCAAGAATTACATAAAT

AACCAATTATTACCCATAGTAAATCAACAGAGCTGTCGCATCTCCAACATTGAAACAGTT

ATAGAATTCCAGCAGAAGAACAGCAGATTGTTGGAAATCAACAGAGAATTCAGTGTCAAT

-continued

```
GCAGGTGTAACAACACCTTTAAGCACTTACATGTTAACAAACAGTGAGTTACTATCATTG

ATCAATGATATGCCTATAACAAATGATCAGAAAAAATTAATGTCAAGCAATGTTCAGATA

GTAAGGCAACAAAGTTATTCTATCATGTCTATAATAAAGGAAGAAGTCCTTGCATATGTT

GTACAGCTACCTATCTATGGTGTAATAGATACACCTTGCTGGAAATTACACACATCACCT

CTATGCACCACCAACATCAAAGAAGGATCAAATATTTGTTTAACAAGGACTGATAGAGGA

TGGTATTGTGATAATGCAGGATCAGTATCCTTCTTTCCACAGGCTGACACTTGTAAAGTA

CAGTCCAATCGAGTATTTTGTGACACTATGAACAGTTTGACATTACCAAGTGAAGTCAGC

CTTTGTAACACTGACATATTCAATTCCAAGTATGACTGCAAAATTATGACATCAAAAACA

GACATAAGCAGCTCAGTAATTACTTCTCTTGGAGCTATAGTGTCATGCTATGGTAAAACT

AAATGCACTGCATCCAACAAAAATCGTGGGATTATAAAGACATTTTCTAATGGTTGTGAC

TATGTGTCAAACAAAGGAGTAGATACTGTGTCAGTGGGCAACACTTTATACTATGTAAAC

AAGCTGGAAGGCAAGAACCTTTATGTAAAAGGGGAACCTATAATAAATTACTATGACCCT

CTAGTGTTTCCTTCTGATGAGTTTGATGCATCAATATCTCAAGTCAATGAAAAAATCAAT

CAAAGTTTAGCTTTTATTCGTAGATCTGATGAATTACTACATAATGTAAATACTGGCAAA

TCTACTACAAATATTATGATAACTACAATTATTATAGTAATCATTGTAGTATTGTTATCA

TTAATAGCTATTGGTTTGCTGTTGTATTGCAAAGCCAAAAACACACCAGTTACACTAAGC

AAAGACCAACTAAGTGGAATCAATAATATTGCATTCAGCAAATAG
```

In one embodiment, double stranded RNA having a sense strand that encodes a microbial antigen, e.g., one that is useful to prevent, inhibit or treat microbial infection, may be introduced to a host organism, e.g., a mammal such as a human, optionally with an adjuvant. The double stranded RNA may be directly administered, or by administration of two plasmids, each encoding one of the strands, optionally in conjunction with positively charged polymers such as PEI, cationic polypeptides, e.g., protamine, or dendrimers, or using a delivery vehicle, e.g., a microparticle or nanoparticle, e.g., a liposome. For instance, double stranded RNA having a sense strand that encodes a RSV fusion protein may be used as a vaccine.

In one embodiment, for protein replacement or augmentation, a double stranded mRNA having a sense strand that encodes Foxp3, e.g., where the sense strand has nucleic acid sequences with at least 90%, 92%, 95%, 97%, 98%, 99% or 100% nucleic acid sequence identity to coding sequences in SEQ ID NO:6 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:6, or a double stranded mRNA having a sense strand that encodes surfactant protein B (Spb), e.g., where the sense strand has nucleic acid sequences with at least 90%, 92%, 95%, 97%, 98%, 99% or 100% nucleic acid sequence identity to coding sequences in SEQ ID NO:7 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:7, may be employed. The double stranded RNA for protein replacement or augmentation may be directly administered, or by administration of two plasmids, each encoding one of the strands, optionally in conjunction with positively charged polymers such as PEI, cationic polypeptides, e.g., protamine, or dendrimers, or using a delivery vehicle, e.g., a microparticle or nanoparticle, e.g., a liposome.

(SEQ ID NO: 6)
```
GTGAGCAGAATCCATGTGCAAGGAGAGCAGGCAGTTCAGGACGAGGGTGAGCTGGTCTCT

GCAGGTTTAGTGCTGTGGCACTGTGCCTGGTATATGCTCCCGGCAACTTCTCCTGACTCT

GCCTTCAGACGAGACTTGGAAGACAGTCACATCTCAGCAGCTCCTCTGCCGTTATCCAGC

CTGCCTCTGACAAGAACCCAATGCCCAACCCTAGGCCAGCCAAGCCTATGGCTCCTTCCT

TGGCCCTTGGCCCATCCCCAGGAGTCTTGCCAAGCTGGAAGACTGCACCCAAGGGCTCAG

AACTTCTAGGGACCAGGGGCTCTGGGGGACCCTTCCAAGGTCGGGACCTGCGAAGTGGGG

CCCACACCTCTTCTTCCTTGAACCCCCTGCCACCATCCCAGCTGCAGCTGCCTACAGTGC

CCCTAGTCATGGTGGCACCGTCTGGGGCCCGACTAGGTCCCTCACCCCACCTACAGGCCC

TTCTCCAGGACAGACCACACTTCATGCATCAGCTCTCCACTGTGGATGCCCATGCCCAGA
```

-continued

```
CCCCTGTGCTCCAAGTGCGTCCACTGGACAACCCAGCCATGATCAGCCTCCCACCACCTT

CTGCTGCCACTGGGGTCTTCTCCCTCAAGGCCCGGCCTGGCCTGCCACCTGGGATCAATG

TGGCCAGTCTGGAATGGGTGTCCAGGGAGCCAGCTCTACTCTGCACCTTCCCACGCTCGG

GTACACCCAGGAAAGACAGCAACCTTTTGGCTGCACCCCAAGGATCCTACCCACTGCTGG

CAAATGGAGTCTGCAAGTGGCCTGGTTGTGAGAAGGTCTTCGAGGAGCCAGAAGAGTTTC

TCAAGCACTGCCAAGCAGATCATCTCCTGGATGAGAAAGGCAAGGCCCAGTGCCTCCTCC

AGAGAGAAGTGGTGCAGTCTCTGGAGCAGCAGCTGGAGCTGGAAAAGGAGAAGCTGGGAG

CTATGCAGGCCCACCTGGCTGGGAAGATGGCGCTGGCCAAGGCTCCATCTGTGGCCTCAA

TGGACAAGAGCTCTTGCTGCATCGTAGCCACCAGTACTCAGGGCAGTGTGCTCCCGGCCT

GGTCTGCTCCTCGGGAGGCTCCAGACGGCGGCCTGTTTGCAGTGCGGAGGCACCTCTGGG

GAAGCCATGGCAATAGTTCCTTCCCAGAGTTCTTCCACAACATGGACTACTTCAAGTACC

ACAATATGCGACCCCCTTTCACCTATGCCACCCTTATCCGATGGGCCATCCTGGAAGCCC

CGGAGAGGCAGAGGACACTCAATGAAATCTACCATTGGTTTACTCGCATGTTCGCCTACT

TCAGAAACCACCCCGCCACCTGGAAGAATGCCATCCGCCACAACCTGAGCCTGCACAAGT

GCTTTGTGCGAGTGGAGAGCGAGAAGGGAGCAGTGTGGACCGTAGATGAATTTGAGTTTC

GCAAGAAGAGGAGCCAACGCCCCAACAAGTGCTCCAATCCCTGCCCTTGACCTCAAAACC

AAGAAAAGGTGGGCGGGGGAGGGGGCCAAAACCATGAGACTGAGGCTGTGGGGGCAAGGA

GGCAAGTCCTACGTGTACCTATGGAAACCGGGCGATGATGTGCCTGCTATCAGGGCCTCT

GCTCCCTATCTAGCTGCCCTCCTAGATCATATCATCTGCCTTACAGCTGAGAGGGGTGCC

AATCCCAGCCTAGCCCCTAGTTCCAACCTAGCCCCAAGATGAACTTTCCAGTCAAAGAGC

CCTCACAACCAGCTATACATATCTGCCTTGGCCACTGCCAAGCAGAAAGATGACAGACAC

CATCCTAATATTTACTCAACCCAAACCCTAAAACATGAAGAGCCTGCCTTGGTACATTCG

TGAACTTTCAAAGTTAGTCATGCAGTCACACATGACTGCAGTCCTACTGACTCACACCCC

AAAGCACTCACCCACAACATCTGGAACCACGGGCACTATCACACATAGGTGTATATACAG

ACCCTTACACAGCAACAGCACTGGAACCTTCACAATTACATCCCCCCAAACCACACAGGC

ATAACTGATCATACGCAGCCTCAAGCAATGCCCAAAATACAAGTCAGACACAGCTTGTCA

GAACACGCTCGTGTGCACGTACACACATGCAGCCCCTCCACTCTATCTCCTGAGTTCCAT

GAATACACACCGACTCTCCAAGATGTACCCCACGTCTCACTTGCCACTGACCCCAGTTCC

CTACCCACAAGCCCCAATCCATGCCTAAGCGTGGCCCACAGAAGAACTTCTCTTTTATTT

GGGATCCAAGGCCCCTGGCCCCCAGTGCCCATCCAATAAACTGTGGTCAGCTGGACAATC

ACCCTGATCAGATATGGGAACATATAAGCAGACAGCTGGGTTTAAGATCCCAGCAGGAGA

AAGCGGATACCAAATGAAAGAGAGTGCTAGAACAGGTGCCTCAGCACTGTCTCCAGCACC

CCAAATTCCTGCCTGTGGTTAGGAGACATCCATCAGGGCTCTAGGCCTCTCGGACCCGGC

CCAAGAGGCCAGCATTCTCCTGGCGAAGGGCTCGGTAGTCCTCACAGATCTTCTCCAGGT

TGCTCAAAGTCTTCTTGCCCATCTCTGTCTCAATCTAAGAAAACAGGATGCACACTTCTT

CAGCCCCTGCAGGCTGCCCCTCTACTGAACTCCTCCCTGCTCCTCCTATTCCCGTAACAG

CAGCCTGTTCCTTCCCATCACTGGGCTTCTGGGTATGTCCTTCCCTCCACTCCACCTAAA

GCAGCAACTTCTGCCATGGGCTCTGGGAGGCATTAGGAGCCGCAAGCTAAAAGCCAGGGC

TCAGAGTAGGCTACTGGCTAGCTTCAGGTCCCAGGCACAGTGGGCACGAAGGCAAAGCCT

CTAGCTGTTAGTTGTCTGGTTTCAAAGACTCTCAGCGCAAAACAAGGAACTATCCCCTGG

CCTGTCTCCATTCCCCTTACCAGTCCCAGGTCTCACCTGCTCCTCAAGATCTCGAACTTC
```

-continued

CCTCATGATAGTGCCTGTGTCCTCAATGGTCTGGATGAGCTGACTGCAATTCTGGAGACA

GCAAGAATACAAGGCTTGCACCTATGCTGGCCCTCTCCAGCCAACCCACCAGGCACATGG

CTCCCCTCACCTCATGCAGGGCAGCTAGGTACTTGTAGGCTTTCCGAACAGCATCATCCT

TCTTAGCATCCTGATAAGACAAAGGGGATCTCCGAGATATCAGCAAGCCATTCCCCCTTT

TCCACTACTCTATGCCCCTATAAGACCACCCTTTACTAGTACTTTGCCTTCATCCTCCAC

AGAGCAAAGCTAGGCCCCAAGCAACAGTGCACCTAAAGGACTCACAGAGGGGCAGGCAAC

AACTCAGTCCCGCCTCCACCCTCCCGGAGGCCAGCCTGCTCCATACCTTGAACACAAGCT

CATCAGTCACTGCAAATGTCCGGTCGAGCTTCCCAGAGAGAGAGTTGATTTCCTTCTGCA

GTTCCTTTGTGTCCGACAAGATCTGGTAGAAACCAGGGTAACTATCAGTGCACATCTTGG

GCAAGGTAGCTGATCAGTGATAACACTCACGTGCCTATACTTACATCCAGTCAGGGCCCA

TGTCGCTGTGTTGGGGTGACTATTATGTGTTGGAGTGTGCCTGAACAGCTCTGCCTAGTA

GTGAGCATAAAGTCCCTGTGT (SEQ ID NO: 7)
GGTACCATGTCTATCCTGACCCTAAGATTAGTTCCTCGGGTTTGAGGATTGCAGCAACAC

TGACCGTTCAGGCCCTGGTCAAGGTGGGGCTGCTGCTTCTTCCTTGGCTTCTTTCCAAGG

AGCCACCAAGAGGCAGAAAGAAATGAAGAGACACAAAGCAAGGCAGAATAGCACTTCGGA

TGACACTGTCCGCATTGCCCGACAGATATGGCACTAGACTGCAGCCAAAGGACTCTCTGA

AACTATTAACAAGGTTGTGAGAACTTGTGACCAGTCTGTGAGGTGCTGTGTCTGGGTGTC

ATGTCACTGGGGACATCATCAGTGTCACCAGTGGCACAGTGGAATGCCTGGTGAGCTGAG

ACACACAAATGAGGCAGGCGTGGTGGGCACACACCTGTAATCCCAACGGAACGTAAACCT

GGTATGGCAGTGCTCACCTGTATGTGGTGGCACTCAGGAAGTGGAGGCAGGAGCATTAGG

AGTCTAAGGTCATCCTCAGCTACATTGACAAATCTGAGACCAGCCTGGGCGACATGAGTC

CTTGTGTTAAAAAAAAAAAAAAAAAAAAAAAAAAAAAAAAAGAGAGAGAGAGAGAGAGAG

AGAATCAGACAGTGGTGGTGCATGCTTTTAATCCAGCACTTGGGAGGCAGAGGCAAACAG

ATTACTGTGAGATCAAGGCCAGCCTGGTCTTCAGAGCAAGTTCCAGGACAAGCAGGGCTA

CATAGAAAAAACCCGTCTCTATAAACAAACAAAACAAAACAAAACAAAAAAAGCAGATC

TCGTGACTCTCTGAAGAAGGCCATTTCCCGCCAGTCCTTGGGGTTAGCCGTAAGTAGCAG

GCTGTAGTGTCTCGAGGCCACAAAAACTAGGAGAACCCTGGGACCACTTCCAGGGTGTCG

TTTTACATCACATGTCCAACTATTTACCTTCATCTTGGGGCTAGCTCCCACCCCATACAG

CCTGTGAGTGCTGGAGGACTTTCTAGGGAGCCTCCGTAGGAAAGGCACTGGCAGGTCTCA

GAAAAGGATCGGGGTCCTGATGGGGGGGCGGGGGTCAGTAGTGCCTAATGCACTCAGACA

AGCACCGGCGCTGCAGCCAGCCCTGAACTGCTTTTTCTCTAAGCCCAGCCAGGTGTGGAC

ATAGCCTCAGAGGACCACGTGTCAGCTGAATCCCATCTCATGCCCAGGAGGGGTGACTGG

GAGAGATGGGCATCTGCTTCTGGGTAAAGCTACCTAAGAGCCACAGGGGACACAGAAATC

TCAGCCTCACAGGGCACTTTCCTGTTTGTCTAATGCTCCTCTCCCTAGCACCAGCCAGGA

GTCTATAGAATCAGAGGATTTTAAAGTAAGGGGGGAGTGGGAGGTCGGTTGGCCCCAGGA

GCACCCTAAGTGTGCCCTTCCGGCACTTACCCTGCGTCAAGAGCCAGGAAGGAAGCTCTC

AAGGGCGTTGCATAAGAGTAGAGGATTGAGAAGCCTGGGGTGGGGCTAGAGAGGCTCATT

CTGACCCCACTCAGCATCCCTTGCACAGTCCAGAGCGTGGGGATCAAACGAGACCCCCTT

GTTTGACGGTGAACAAAGTCAGGCTGAGGGGGTTCGGGAAGGGGGTAAAGGACTAGGAAC

CGACATCGGCCAGCACACGGGAGGTGGACAGGGGTGTCCCTGCTGAGAAGACCTGGAGGG

CTCTCAAGACACAGGCAAACACTGAGGTCAGCCTGTTCCCATGGAGTCCAGCCCCCAGGT

CCTCTCCCCTACTATAAGAGCCCATGACTCAAGTAGGGTACTAAGCAGTAGGCAGCCATG

GCCAAGTCGCACCTACTGCAGTGGCTACTGCTGCTTCCTACCCTCTGCTGCCCAGGTGCA

GGTGAGTCCCCGGCCTCCCTCACAGAGGCCTCTCCAGCACTTACTGAGTCAGCTCCGTGC

CCAGAAAGACCCCAGTCTGCACATAATCCAGAATTTAAACGCCAGTTAGCTGAGGCACAG

AGAAGTCCTAGGGCCTCATCCAAGGTCACAGTTAGTGGATGGATGTTGAAGCAGGAGGAC

TCAGAGCTGCCTGGCAGAAGCAATGGCCACTCCTTTGCAATGAAACTGGGTTGGAGGTGG

GGTGGAGGCAGGGTGCCGAGTGTATGCTGGATCCTGATGAGAGTTGCTCTGACCCCAACT

CCAGCTATCACGTCGGCCTCATCCCTGGAGTGTGCACAAGGCCCTCAATTCTGGTGCCAA

AGCCTGGAGCATGCAGTGCAGTGCAGAGCCCTGGGGCACTGCCTGCAGGAAGTCTGGGGG

CATGCAGGAGCTGTGAGTAGCACCAAGCGGGCACTGGAAATCCAGGGAGGAGGAACTGGG

GTGGATTCTGAGCGGACCTTAGGAAATTGGAGTTCCCACAAGGCTGGGGTGGCAGGGAAT

GATGGAATGGTATAGTGTGACAGGAAATGGTGGGCAGAGTACAATAGAAGGAAACATGGT

GGAATGAGATGAATGGGGTGGGCATGGTGGGTAAGCAGGGTGGATGTGTGGGTAAGACA

GGGTGGATGTGGTGGGTAAGACAGGGTAGATGTGGTGGGTAAGAGGGGGTGAGCATGTGG

GTAAGATGGGGTGGCTGGGGTGAGATGGACAAGATGGAATAGAACAGGGTGGATCAAGTG

GGTGGCACAGAATGGGATGGAATTTGCACAATGGGATGAGATGGGATGATGGGTGGGTAG

CCTTAAGGTACCTGTCAGCCTGTGTCTGAGAAAGCCTCAATCCCTGGAGTTAGGAGCATG

CCCCCAACTCATTAGCCTCACTTGAGACCCTTTCTTCCAGAATGACCTGTGCCAAGAGTG

TGAGGATATTGTCCACCTCCTCACAAAGATGACCAAGGAAGATGCTTTCCAGGTAATGGG

AAACGGTACAGTGTGATCTGGTAGAGGCCTGGCGTCAGGGGACTCTGGTGGGGGCAGACC

TCAGAAAGACCAGGCTAATCCTCCCTTCTCTGCTCTCCCAGGAAGCAATCCGGAAGTTCC

TGGAACAAGAATGTGATATCCTTCCCTTGAAGCTGCTTGTGCCCCGGTGTCGCCAAGTGC

TTGATGTCTACCTGCCCCTGGTTATTGACTACTTCCAGAGCCAGATTGTGAGGACCCTGA

CCTACCTGCCGCACAGTGCATGTGCCTAAGTGGCCACTTACCTATATAAGTGGCACCCCA

ACACATGCACACACACATACACACCCACAGACGCAATAAGACACACACACACACGT

ACACACACACACACACACACACACACACACACACTTCCCACTACAGCCACAGGAAGCT

CAGTCTCTTCATCCAGATACCCAAATCAGAGCCTGCCTGCTCAGCATACTACAGACATTG

AGACCCGCCCTCCATCCCCTCACCCACACATGCCCACATTCTTATTGTCACACAATATGC

TCACACACACTCACTCTTTCCAGACACATGCTCCCAGGCCCTACACAGCCCCATCTCTCT

GTCTTTGTCCCTTTCATAGTGTCCTAAGATGCAGTACTTCACCCAGCCTGCTCCCCATAA

CCCCAGGCTCAAAGACTGTGGCCCTTGTCCCTGAATATGAACCTGGGCAGAGAGGGGTTC

CCTCCTTACCCTAAAACCCCTCACCTGTTCCATGCCCTAGAACCCCAAAGCCATCTGCAA

TCATGTAGGCCTGTGCCCACGTGGGCAGGCTAAGCCAGAACAGAATCCAGGGATGCCGGA

TGCCGTTCCAAACCCTCTGCTGGACAAGCTGGTCCTCCCTGTGCTGCCAGGAGCCCTCTT

GGCAAGGCCTGGGCCTCACACTCAGGTAAGCCAGTCCATTCCCAGCAGCTGCTGGGAATC

CAGAAGGCTAGCATGGCCGCTGAGACGCGTGGGCACCCAGAGAGGCTGAGCTCAAACTAG

GAGGCAGAGATGGCAAGGTCAGGCAAGGTCACACAACCGAGGTAGCTCCCAGCCTAACCA

CACTTCACCGCTTCCTTCCTCAGGACTTCTCTGAGCAACAGCTCCCCATTCCCCTGCCCT

TCTGCTGGCTTTGCAGAACTCTGATCAAGCGGGTTCAAGCCGTGATCCCCAAGGTAAGGA

-continued

```
CCACACAGAGCTCAGAGGGGCCCCCAATAGCTGGCACCTTCCTCCACCTCAACACTCCAA

GAAGGCTGTGAGGAGTTAGATGAGGAGACACCCACACATTGCTCCTACCCAAGGAACCTT

GAGGCTCAGGTATGGGAGGTTAGGTCAGAGCCACCTTCTCTTCCAACAGATCACCATCGG

AAGGCTGAGAAGCACTGGTTGTCACTGTAGGAAAAAAGTACATTAATTTCTCAAAAAAAA

AAAAAAACAGTTCATCAATAGTAAGCATCTCTTCTGTCCTCCAAATCCATGGTAGCCTCT

GCCAGTGCCTTGTCAGATGAGGATTGTTCTCCCCACAAATGGTCATGGCCTATCAACACT

AACACTAAGCCCACATCAGTCATAAAGACAACAGGGCACACAGTCAAGCCTTTCTGAAGC

CTGTGTGATGGAAGGAACGTGCAGACTATAGAGCAGGATGAGCTGAGGGGTCGCACAGAT

AAAAATGGTAACAGACAGGTCAGCCAGGGAGAGGCTCTGAAGAGGGTAACAACTAAGCCA

AGATCTAGGAGAAAACAAGGTCCCCAGGGGCCAAGGACATCCATCCATCAATAAAAAATG

AGCTCAATCAGATGTTGGAGGGAGGGACTCTGTAAGGAGGGACCAGGAGCAGGGGGCAGC

GTTTGGGGTGTAAATGATAGATAAATGCCTTTAAAATGAGCTCAGAGGGCTAGGAAGATG

GCTCGGTGAGTACAGTCCTTGCTGAACCTGAGTTCAGATACTTGCACCCTCATAAAAGTT

GGGGGGTGGGCTGGAGACATGGCTCAGTAGTTAAGAGCACTGACTGCTCTTCTAGAGGTC

CTGAGTTCAATTCCCAGCAACCACTTGGTGGCTCACAACCACCTATAATGGGATCTGATG

CCCTCTTCTGGTGTGTCTGAACTTACATACATAAAATAAAAATAAAAGTTGGGGGTTGCT

CACAGTCAGCTAATGGATGGATCATAGGGCTCCCAATGGAGGAGCTAGAGAAAGTAGCCA

AGGAGCTAAAGGGATCTGCAACCCTATAGGTGGAACAACATTATGAGCTAACCAGTACCC

CGGAGCTCTTGACTCTAGCTGCATATATATCAAAAGATGGCCTAGTCGGCCATCACTGGA

AAGAGAGGCCCATTGGACTTGCAAACTTTATATGCCCCAGTACAGGGGAATACCAGGGCC

AAAAAGGGGGAGTGGGTGGGCAGGGGAGTGGGGGTGGGTGGATATGGGGGACTTTTGGTA

TAGCATTGGAAATGTAAATGAGTTAAATACCTAATAAAAAATGGAAAAAAAAAAAGTTGG

GGGTTAGCAATGAACATTTGTAACCCTACACACTAGGTAGTCAGAAATAGGCAGATCCCT

AGAGCATGCTGGCCAGCCAGTCTAGCCAAATGGATGAGCTTCAGGGTTAGTGTGAGACCT

TGTCTCAAAAAAAAAAAAAAAAAAAAAAAAAAATGGACGGCCTGAAGATTCGGATCGACAG

TTAGGAACATTTGCTGCTTTTCAGAAGAGTGAGTTGGGTACCCAGCACCACTGTCAGGCA

GCTCACAACCCCCTGTAACTGCTGCTCTAGGGAATCCAATGCCCTCTTCTGGCAGCCAAG

GGCACCAGCACATATGTGGCATTCATATACTCAGATACACAGACATATGTAAAAATAAAA

ATAAATCTTTAGAAAATAATTAGGTAGGGAGTGAAGTGACTAAGGAAGACACTCAATCTT

GGCTCTGGCCTCCACACACATGTGCACATGTACTTAAACATCTACGTGCAAAACAAACAA

ACAAACACCCAGCCGTATCAATGTGAACATCACTGAGGACCGAAGGCATGAGCAAGACTG

TTAAGAGACAATGTATAGACAGATGGAGATGGCATCAGAATTGCTGAGAGGGGACAGGCA

GCCAACGGGGGACCGTGCTGCATTGCCAGGGAAGCCAAGAGAGAAGGGTGTTTGACTGAT

TGAAAGGCAGCTGAACCATCAGGCAGGGTGAGAGTTAGGCAGGGGATGTGGAAGTGTTCC

AAAAAGGGGAGCAGGCATGGTGAGGCTTCCTAAGGTCAGAAGCCATTCTAGCGTGTTCTC

CAGGCAGCAGGGACCAGAGAGAGGATAAGGCCAGGGAAAGAGGCATGGGTGGAGGTAATC

CAGGAGTGAAGACCATTTCACCAATGAGCAGCTTGGTCATTGACTACAGTGACTATTGAT

TTACATCACCATGACAGGAGAGCCATGTGTGGGTCAATGATAACAGGTGGGTCTCTTAAG

TGAAGTGCCCCATTTGGGAGCCATCACACTCCAGGGGTGTCCATATTCTGAGTCCTCCCC

CTGCCTCAACCTCCTGGCACTGGGGCTAGCTGGTCACATGGGCTGAATAAGGAGTAAAGG

AAAAAGCCACACCCTGGTGACCTCTGTCACCCTTCAGCTAGAGCCTGCTTGGAATTGGAG
```

-continued

```
TTGAGGTAGGAGATGTGCTGGCTTTCCCAGGGGTTCCAAAAGCCAAAGACATGTCAGCTC

TGGGGGCCAGCAGAAGGAACTGCCTGTCTTCCTGATGCATAAGCATGGGAAGGTAGGTGG

CCCTCGGTCAGGGAATGGGTTTGAATTGGGTCAGGCTGTTAGATGCCATGGCCTTGCAGC

CCCCTTTCAAATGACTCAAGCCTTTAGAGCTAGATCTATATTTGGTGTCAACTGCAGATT

CTCTCAGTGACTCCGGGTGCACCTGAGACCCCTGCTGTCTTGGATGCTCAGTGACCTGTG

GACAGAACTGCTCTTTCCTAGAAGGGAGAAAGGGGATGCATCTGGGGTGCCCACTCAGTT

GGGCACAGTGACATCGTGCCAGAAGAAGGTTCTATGGTTGTCCTTTCTCCACCTTCACCC

CAGGGTGTGCTGGCTGTGGCTGTGTCCCAGGTGTGCCACGTGGTACCCCTGGTGGTGGGT

GGCATCTGCCAGTGCCTGGCTGAGCGCTACACAGTTCTCCTGCTAGACGCACTGCTGGGC

CGTGTGGTGCCCCAGCTAGTCTGTGGCCTTGTCCTCCGATGTTCCACTGAGGATGCCATG

GGCCCTGGTAAGACTTGCCCGTCCCCTCCCCCTCCCCAACTCACATCCCTCCAGTGCACA

TGGGAGGGAACATGGACAAGGTGGGGTTCAGGAACCAACACTTTTTTTAAACTATTTATT

TCTATGGATATGGCTGCTTTTATTTATATAGCTGAGGCTGGCTTTGAACTCCTAATTTCC

CTTCCTCAGCCATTCAAATGTTAGGAAAGGCTAGCAATGACTGTACTCAGCTTCTAGCTC

TCTCCAAGTGGACTTCTCCCAGTTGAGTTAAAGAGTGATGGGGGAGGGGTGGGGAACAGG

GCAGGACCCTGGGAGAAGGCTAAGTTCTTTTTTTGCTCCAGCTTGGACATCTATATACCC

CATGTATGCCTGGCTCCCACAGAGGCCATAAAGGATGTCAAATCCCCTAGAATTGGAATA

ACTGACAGTTATGAGCCATCATGTGGGGCTCTGGGAATCGAACCTCAGCCCTCTGGAAGA

GCAGCCAGTGCTCTTAACCACGGAACCATCTCTCCAGCCCCAGAACCAACACTTGTACAA

GACAGTCCTGGGGGAAAGATTAAAACAGAGTCTTACTACATAGCACAGGTTGGCCTCGAG

CTTGGTGCAATCCTCCTGCCTCAGCCTCTCAAATACTGGCATGACAAGGTATGTGCCTCC

ATACCCAGCTTGCTGGACAATTCTAACTGCTTTCTCTTTAGCCCTCCCTGCTGTGGAGCC

TCTGATAGAAGAATGGCCACTACAGGACACTGAGTGCCATTTCTGCAAGTCTGTGATCAA

CCAGGCCTGGAACACCAGTGAACAGGCTATGCCACAGGCAATGCACCAGGCCTGCCTTCG

CTTCTGGCTAGACAGGCAAAAGGTAGGGGGCCCACGGGTTGGATGTATGTCATATGTGTG

ATGGTGCCGAGCTAGAAGAGACTTTGTAGCTAGACACACGCACGATGCTGGTTCCCAGCC

TGGTGGACAGGCATGTGGGTCAGACAATGATGGGATTGTAACAAATTTAACTGGCTAGGA

GACATCATGGACCCAAGGCTTTGGACTATGGAACATCAGCAGGCCTTCTTTATGGACTAA

GCACAAGAAAAGTCCTGTTAGTCCCAACAGGAAAGGGTCATACTGCCCTTTCTTGGTTTC

ACTCGATGGTGTGTTTGCCACACTGTTCTCCCAGTGTGCCATGTCACCCCCATGATGGGT

GGTAGCATTTGACAGTACCTAGCAGGCACCAGAAAATGAGAAAAGCCAGGGTCAGCTGGA

GCAGAAAAGAACTTAGCCTTTTCCCAGGGTCCTGTTCTGCCCCACCCTGCTCACTCTGT

AGAAGTCCTGCAGGAGAGAGCTGGAAGCTGGTACCATAGTGCTAGCCTGTAATTCTAACA

TTTGGAAAGGCTGAAGAAGGAGAAATGGGAGTTCAAAGCCAGCCTCAGCTATATAAATAA

TGAGTTCAGGGTCAGCCTGGGCTACATGAGACCCTGTCTGGTGAAAGGAGACAGAGATAG

GAAAGAACATGAGGCTTGGGTAAGGCTCACTGGCATGGCCACAACCAAGTTTGATCCCTG

GGATCCGTATGGTAAACAAAGAGAATCAACTCCTGTAAACTTTCCTTATGAACACACACA

CACACGAAAACATAATTTTGAAGCCAGGCTGTGGTGGTGCACACCTTTAGTCCTAGCCCT

TGGGAGGCAGAAGCAGATGGATCTAAGTTTGAGCCCAGCCTGGTCTACAGTGTGAGCTCC

AGGACAGCCAGGGTTACACAGAGAAACCCTGTCTCACAAAACCAAAAAGAAATCAACAAC
```

-continued

```
CACAAAGAACTGAACAGATAGTTCCTTAAGCCTGTGATGAATCCCCTCACTACAGTGGGA

CTTTCTTTAGAGAGGGTCCTATGTAACTTAAACCGCCTCCACCTCCTTTGTACTGAGACT

ACAGGCAGGTACCACTACTGAGTTTCATGTAGTTCTGAAGTTGAAACTAAAGGTTTCATG

CATGCTAGGCAACCATGAGACGATGCTAAGCTGCAAGCCTGCTCCAGCTCCAAGGCCCTG

GCTTCCTCCAAAGCCTGGTTTCAGCCAAACTTAGATAGAGTCCCTTTTTTTAAGACTCAT

TTTATTTGTGTTTTTAGTGCATGTATGTATGGACATCATGTGTGTGTGGTGCCGGGGGGA

GGGGGTCAGAAGAGGCCATCAGATTCCCTGGAACTGGAGTTGAGTGGTTATAAGCCGTCC

TTCCTGTCCTCCAAAGAGCAGCAAGTGCCTAACCCCCGAGCCATCAGCCATTCAGCCCTT

CGGTTGAGTCTTTAATGGTCAGCCAGGCACTGATGGAAAAACACAAACCCACAGTCCGGA

GTGGCAGAGTGAGGTAGAACGCCAGATCTGCAGGTTAAGTTCTCTCCTAGAGGGGGGTCT

ACATATTGTGTCTTTCCTCAGTGTGAACAGTTTGTGGAACAGCACATGCCCCAGCTGCTG

GCCCTGGTGCCTAGGAGCCAGGATGCCCACATCACCTGCCAGGTATGCCCACTCTTCAGC

TGGTCCCAGGAGTCCCCTCTGCTCCCACAGTCCCACCCTCCTTGGTCTATGATCCTCAAG

AGCCCCATTTCTTGGATCCAGGAAGCCTAGGGCTCAGAAGCCCAGAACTAAGTGTACCCA

TAGAACAGGCTTTGGACTTGGAGCAGAAAAGAACACATACTGATTAGGTGGGAGGGGCAA

GTTCATGATGGATGGGCAGCTGGGGGCTGGGGTATGATGCTCCTTATTGCATGTGGTGTG

TTTAGTGACCAGTTTGTTCTATGGTGGGGCTATAGTATGAGGTGGGGGTCCCACTAAGTC

CCAAGGCCATTGACTTAGGGAATGGCACAAGGGGTTCTGAAGGTGAAGGTGAAGTGAGAG

TTGTCTCCATAGCCTTGAGAATTAGACGTAGAAAGCTGAGGCCCACGTGCTGTCTCCAAC

AGGCCCTTGGCGTATGTGAGGCCCCGGCTAGCCCTCTGCAGTGCTTCCAAACCCCACACC

TCTGAGAACGCGGTCTCCAGGTGAGTCCAGCCTCCTGGGGAGAGAGAGGAATGGGTCTTT

GCTTGCTAAGGTTTGGGAACAAGATGGTCATCCTGCCCACTTCTGTGGACTGTGTCATCC

TACCTCTGCCAGGCACAGTTCCAGGCTCCTCGGGGTCTCCAGTGGTTCCATCAGGAAAAG

GCAGTCTTTTGGACCTATCGTCACTCCTTGCTCTCCCACCCCATCCAGCCCTCCACAGCT

TCTATCTAAGGCTTCATCACATCTGAGCTGCCTGACCTTAAAGATACTCCATGTTCGAGC

AATGGCCAACATTTCTTACTTCACTGTCTCGGCTGTCTCTCCCTCAGATGCCAGCAGCAC

CATGGTCACCTGACCTCACCCTGCCCAGGCTCCCTGTTTTCTAAGCCAGAAATAGCTCTG

ACACCAGAGTCAGGAAATGACATGGGGAGTGTGGGGCGAGAAAGGCAACAGTCTCTCAAG

TGACCCTGACAGTAATCTGGTCCAGGTCACAATGTACTTAAAGCCAGCGCTCGCTGGGTA

GTCATTTATCCATTTGTTCCCATTTGTGAAAATCTGCTGGTGTGCACAGCTGGCCCACCA

CTTCTAATGCGAGGAAGGACCCCAGCACTGTCACAGCCACTGTGGGCAGAGGGGCACTTC

AAGTCAGTAAGTCCCTTGGGGGCCAATTTAATGTCTCCCCTCCCATCCCCCATCAAGTCC

ATCTGGGTGCGCGAAGGGAGGCAATCCAGGAGTCACCTTTTTCTAGCTCTCAGGGCTCTA

GGCCTTGCCTGCTGAAGAAGGAATTGTGAGAGACTCCCTGAGTTCTGGTCCCAACTCTGC

TATCAACAGTCAGTGGATCCCCCGGGAAAATCGCACAGCCCCCACCCTTTGCGATATCAC

TAAACTAGCTGCAAGTAGCCCAATGAAGGGAACTTCGGCACTTATGAACTGTCACCATCA

CAGTGACAGTGACCCTACTCCCACCAGTAGCTACTCTCCTTGAAAAAGACCTTACCTCCC

ACCCTAATGCTACTTCCTTTCCCACAGCAGCCTGCTCCAGAGGACAAGCCTCAGCCTGCA

CCCTCAGCCCTGTGTCAGTCTGTATGTCCCAGCTCTAACTACAGACCACCACCACCACCA

CCACCACCACCACCACCACCACCACCACCACCACCACCACCACCACCACCACCACAGTGG

TTTCTGGCTCCCCCCGGTGATGGGGGGCGGCAGGCCCACGTCCTCTGGAAGCCTTCAGAA
```

-continued

GGGGCTTCGGGCCTTCGCCTCCACCAGAGCCAAGCCAGCTCCCATAGCTCCCACAGCCCA

CAGGGACTGAGAAGAACTGTTGTGGCTCCAAGAAGACATCGGGTAGAAGCTGGGTATAGC

CACACCAACCCCTTGCTAACATTTCTATGAAATCCAAACTTGAGAAGAATAAAGAATGGG

AACATGGAGCATTATTCTAAGGGCTGTGGGCGAGGCGCAGTGACAGGGCACTTTCCTAGC

AAGCAGGAAACCTGGGTTGGATCC

For somatic reprogramming, a double stranded mRNA having a sense strand that encodes Oct4, e.g., where the sense strand has nucleic acid sequences with at least 90% nucleic acid sequence identity to coding sequences in SEQ ID NO:8 or a nucleic acid sequence that encodes a protein with at least 80% amino acid sequence identity to a protein that is encoded by SEQ ID NO:8; Sox 2, e.g., where the sense strand has nucleic acid sequences with at least 90%, 92%, 95%, 97%, 98%, 99% or 100% nucleic acid sequence identity to coding sequences in SEQ ID NO:9 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:9; Klf4, e.g., where the sense strand has nucleic acid sequences with at least 90%, 92%, 95%, 97%, 98%, 99% or 100% nucleic acid sequence identity to coding sequences in SEQ ID NO:10 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:10; c-myc, e.g., where the sense strand has nucleic acid sequences with at least 90% nucleic acid sequence identity to coding sequences in SEQ ID NO:11 or a nucleic acid sequence that encodes a protein with at least 80%, 82%, 85%, 87%, 90%, 92%, 95%, 97%, 98%, 99% or 100% amino acid sequence identity to a protein that is encoded by SEQ ID NO:11, or any combination thereof, may be employed.

(SEQ ID NO: 8)
ATGGCGGGACACCTGGCTTCGGATTTCGCCTTCTCGCCCCCTCCAGGTGGTGGAGGTGATGGGCCA

GGGGGGCCGGAGCCGGGCTGGGTTGATCCTCGGACCTGGCTAAGCTTCCAAGGCCCTCCTGGAGG

GCCAGGAATCGGGCCGGGGGTTGGGCCAGGCTCTGAGGTGTGGGGGATTCCCCCATGCCCCCCGC

CGTATGAGTTCTGTGGGGGGATGGCGTACTGTGGGCCCCAGGTTGGAGTGGGGCTAGTGCCCCAA

GGCGGCTTGGAGACCTCTCAGCCTGAGGGCGAAGCAGGAGTCGGGGTGGAGAGCAACTCCGATGG

GGCCTCCCCGGAGCCCTGCACCGTCACCCCTGGTGCCGTGAAGCTGGAGAAGGAGAAGCTGGAGC

AAAACCCGGAGGAGTCCCAGGACATCAAAGCTCTGCAGAAAGAACTCGAGCAATTTGCCAAGCTCCT

GAAGCAGAAGAGGATCACCCTGGGATATACACAGGCCGATGTGGGGCTCACCCTGGGGGTTCTATT

TGGGAAGGTATTCAGCCAAACGACCATCTGCCGCTTTGAGGCTCTGCAGCTTAGCTTCAAGAACATG

TGTAAGCTGCGGCCCTTGCTGCAGAAGTGGGTGGAGGAAGCTGACAACAATGAAAATCTTCAGGAG

ATATGCAAAGCAGAAACCCTCGTGCAGGCCCGAAAGAGAAAGCGAACCAGTATCGAGAACCGAGTG

AGAGGCAACCTGGAGAATTTGTTCCTGCAGTGCCCGAAACCCACACTGCAGCAGATCAGCCACATC

GCCCAGCAGCTTGGGCTCGAGAAGGATGTGGTCCGAGTGTGGTTCTGTAACCGGCGCCAGAAGGG

CAAGCGATCAAGCAGCGACTATGCACAACGAGAGGATTTTGAGGCTGCTGGGTCTCCTTTCTCAGG

GGGACCAGTGTCCTTTCCTCTGGCCCCAGGGCCCCATTTTGGTACCCCAGGCTATGGGAGCCCTCA

CTTCACTGCACTGTACTCCTCGGTCCCTTTCCCTGAGGGGGAAGCCTTTCCCCCTGTCTCCGTCACC

ACTCTGGGCTCTCCCATGCATTCAAACTGA (SEQ ID NO: 9)
ATGTACAACATGATGGAGACGGAGCTGAAGCCGCCGGGCCCGCAGCAAACTTCGGGGGGCGGCGG

CGGCAACTCCACCGCGGCGGCGGCCGGCGGCAACCAGAAAAACAGCCCGGACCGCGTCAAGCGG

CCCATGAATGCCTTCATGGTGTGGTCCCGCGGGCAGCGGCGCAAGATGGCCCAGGAGAACCCCAA

GATGCACAACTCGGAGATCAGCAAGCGCCTGGGCGCCGAGTGGAAACTTTTGTCGGAGACGGAGAA

GCGGCCGTTCATCGACGAGGCTAAGCGGCTGCGAGCGCTGCACATGAAGGAGCACCCGGATTATAA

ATACCGGCCCCGGCGGAAAACCAAGACGCTCATGAAGAAGGATAAGTACACGCTGCCCGGCGGGC

TGCTGGCCCCCGGCGGCAATAGCATGGCGAGCGGGGTCGGGGTGGGCGCCGGCCTGGGCGCGG

-continued

GCGTGAACCAGCGCATGGACAGTTACGCGCACATGAACGGCTGGAGCAACGGCAGCTACAGCATGA

TGCAGGACCAGCTGGGCTACCCGCAGCACCCGGGCCTCAATGCGCACGGCGCAGCGCAGATGCAG

CCCATGCACCGCTACGACGTGAGCGCCCTGCAGTACAACTCCATGACCAGCTCGCAGACCTACATG

AACGGCTCGCCCACCTACAGCATGTCCTACTCGCAGCAGGGCACCCCTGGCATGGCTCTTGGCTCC

ATGGGTTCGGTGGTCAAGTCCGAGGCCAGCTCCAGCCCCCCTGTGGTTACCTCTTCCTCCCACTCC

AGGGCGCCCTGCCAGGCCGGGGACCTCCGGGACATGATCAGCATGTATCTCCCCGGCGCCGAGGT

GCCGGAACCCGCCGCCCCCAGCAGACTTCACATGTCCCAGCACTACCAGAGCGGCCCGGTGCCCG

GCACGGCCATTAACGGCACACTGCCCCTCTCACACATGTGA (SEQ ID NO: 10)

ATGAGGCAGCCACCTGGCGAGTCTGACATGGCTGTCAGCGACGCGCTGCTCCCATCTTTCTCCACG

TTCGCGTCTGGCCCGGCGGGAAGGGAGAAGACACTGCGTCAAGCAGGTGCCCCGAATAACCGCTG

GCGGGAGGAGCTCTCCCACATGAAGCGACTTCCCCCAGTGCTTCCCGGCCGCCCCTATGACCTGGC

GGCGGCGACCGTGGCCACAGACCTGGAGAGCGGCGGAGCCGGTGCGGCTTGCGGCGGTAGCAAC

CTGGCGCCCCTACCTCGGAGAGAGACCGAGGAGTTCAACGATCTCCTGGACCTGGACTTTATTCTCT

CCAATTCGCTGACCCATCCTCCGGAGTCAGTGGCCGCCACCGTGTCCTCGTCAGCGTCAGCCTCCT

CTTCGTCGTCGCCGTCGAGCAGCGGCCCTGCCAGCGCGCCCTCCACCTGCAGCTTCACCTATCCGA

TCCGGGCCGGGAACGACCCGGGCGTGGCGCCGGGCGGCACGGGCGGAGGCCTCCTCTATGGCAG

GGAGTCCGCTCCCCCTCCGACGGCTCCCTTCAACCTGGCGGACATCAACGACGTGAGCCCCTCGG

GCGGCTTCGTGGCCGAGCTCCTGCGGCCAGAATTGGACCCGGTGTACATTCCGCCGCAGCAGCCG

CAGCCGCCAGGTGGCGGGCTGATGGGCAAGTTCGTGCTGAAGGCGTCGCTGAGCGCCCCTGGCAG

CGAGTACGGCAGCCCGTCGGTCATCAGCGTCAGCAAAGGCAGCCCTGACGGCAGCCACCCGGTGG

TGGTGGCGCCCTACAACGGCGGGCCGCCGCGCACGTGCCCCAAGATCAAGCAGGAGGCGGTCTCT

TCGTGCACCCACTTGGGCGCTGGACCCCCTCTCAGCAATGGCCACCGGCCGGCTGCACACGACTTC

CCCCTGGGGCGGCAGCTCCCCAGCAGGACTACCCCGACCCTGGGTCTTGAGGAAGTGCTGAGCAG

CAGGGACTGTCACCCTGCCCTGCCGCTTCCTCCCGGCTTCCATCCCCACCCGGGGCCCAATTACCC

ATCCTTCCTGCCCGATCAGATGCAGCCGCAAGTCCCGCCGCTCCATTACCAAGAGCTCATGCCACCC

GGTTCCTGCATGCCAGAGGAGCCCAAGCCAAAGAGGGGAAGACGATCGTGGCCCCGGAAAAGGAC

CGCCACCCACACTTGTGATTACGCGGGCTGCGGCAAAACCTACACAAAGAGTTCCCATCTCAAGGCA

CACCTGCGAACCCACACAGGTGAGAAACCTTACCACTGTGACTGGGACGGCTGTGGATGGAAATTC

GCCCGCTCAGATGAACTGACCAGGCACTACCGTAAACACACGGGGCACCGCCCGTTCCAGTGCCAA

AAATGCGACCGAGCATTTTCCAGGTCGGACCACCTCGCCTTACACATGAAGAGGCATTTTTAA (SEQ ID NO: 11)

CTGGATTTTTTTCGGGTAGTGGAAAACCAGCAGCCTCCCGCGACGATGCCCCTCAACGTTAGCTTCA

CCAACAGGAACTATGACCTCGACTACGACTCGGTGCAGCCGTATTTCTACTGCGACGAGGAGGAGA

ACTTCTACCAGCAGCAGCAGCAGAGCGAGCTGCAGCCCCCGGCGCCCAGCGAGGATATCTGGAAG

AAATTCGAGCTGCTGCCCACCCCGCCCCTGTCCCCTAGCCGCCGCTCCGGGCTCTGCTCGCCCTCC

TACGTTGCGGTCACACCCTTCTCCCTTCGGGGAGACAACGACGGCGGTGGCGGGAGCTTCTCCACG

GCCGACCAGCTGGAGATGGTGACCGAGCTGCTGGGAGGAGACATGGTGAACCAGAGTTTCATCTGC

GACCCGGACGACGAGACCTTCATCAAAAACATCATCATCCAGGACTGTATGTGGAGCGGCTTCTCGG

CCGCCGCCAAGCTCGTCTCAGAGAAGCTGGCCTCCTACCAGGCTGCGCGCAAAGACAGCGGCAGC

CCGAACCCCGCCCGCGGCCACAGCGTCTGCTCCACCTCCAGCTTGTACCTGCAGGATCTGAGCGCC

-continued

```
GCCGCCTCAGAGTGCATCGACCCCTCGGTGGTCTTCCCCTACCCTCTCAACGACAGCAGCTCGCCC

AAGTCCTGCGCCTCGCAAGACTCCAGCGCCTTCTCTCCGTCCTCGGATTCTCTGCTCTCCTCGACGG

AGTCCTCCCCGCAGGGCAGCCCCGAGCCCCTGGTGCTCCATGAGGAGACACCGCCCACCACCAGC

AGCGACTCTGAGGAGGAACAAGAAGATGAGGAAGAAATCGATGTTGTTTCTGTGGAAAAGAGGCAG

GCTCCTGGCAAAAGGTCAGAGTCTGGATCACCTTCTGCTGGAGGCCACAGCAAACCTCCTCACAGC

CCACTGGTCCTCAAGAGGTGCCACGTCTCCACACATCAGCACAACTACGCAGCGCCTCCCTCCACT

CGGAAGGACTATCCTGCTGCCAAGAGGGTCAAGTTGGACAGTGTCAGAGTCCTGAGACAGATCAGC

AACAACCGAAAATGCACCAGCCCCCAGGTCCTCGGACACCGAGGAGAATGTCAAGAGGCGAACACAC

AACGTCTTGGAGCGCCAGAGGAGGAACGAGCTAAAACGGAGCTTTTTTGCCCTGCGTGACCAGATC

CCGGAGTTGGAAAACAATGAAAAGGCCCCCAAGGTAGTTATCCTTAAAAAAGCCACAGCATACATCC

TGTCCGTCCAAGCAGAGGAGCAAAAGCTCATTTCTGAAGAGGACTTGTTGCGGAAACGACGAGAACA

GTTGAAACACAAACTTGAACAGCTACGGAACTCTTGTGCGTAA.
```

In one embodiment, for genome editing, a double stranded mRNA having a sense strand that encodes a nuclease such as Cas9, e.g., where the sense strand has nucleic acid sequences with at least 90%, 92%, 95%, 97%, 98%, 99% or 100% nucleic acid sequence identity to coding sequences in SEQ ID NO:12 or 13 for a nuclease, or a nucleic acid sequence that encodes a protein with at least 80%, 82%, 85%, 87%, 90%, 92%, 95%, 97%, 98%, 99% or 100% amino acid sequence identity to a nuclease that is encoded by SEQ ID NO:12 or 13, may be employed. The double stranded RNA for a nuclease such as Cas9 may be directly administered, or by administration of two plasmids, each encoding one of the strands, optionally in conjunction with positively charged polymers such as PEI, cationic polypeptides, e.g., protamine, or dendrimers, or using a delivery vehicle, e.g., a microparticle or nanoparticle, e.g., a liposome, optionally in conjunction with guide RNA.

(SEQ ID NO: 12)

```
atggataaga aatactcaat aggcttagat atcggcacaa atagcgtcgg atgggcggtg atcactgatg aatataaggt tccgtctaaa aagttcaagg ttctgggaaa tacagaccgc cacagtatca aaaaaaatct tataggggct cttttatttg acagtggaga gacagcggaa gcgactcgtc tcaaacggac agctcgtaga aggtatacac gtcggaagaa tcgtatttgt tatctacagg agatttttc aaatgagat gcgaaagtag atgatagttt ctttcatcga cttgaagagt cttttttggt ggaagaagac aagaagcatg aacgtcatcc tatttttgga aatatagtag atgaagttgc ttatcatgag aaatatccaa ctatctatca tctgcgaaaa aaattggtag attctactga taaagcggat ttgcgcttaa tctatttggc cttagcgcat atgattaagt ttcgtggtca ttttttgatt gagggagatt aaatcctga taatagtgat gtggacaaac tatttatcca gttggtacaa acctacaatc aattatttga agaaaaccct attaacgcaa gtggagtaga tgctaaagcg attctttctg cacgattgag taaatcaaga cgattagaaa atctcattgc tcagctcccc ggtgagaaga aaaatggctt atttgggaat ctcattgctt tgtcattggg tttgaccccct aattttaaat caaattttga tttggcagaa gatgctaaat tacagctttc aaaagatact tacgatgatg atttagataa tttattggcg caaattggag atcaatatgc tgatttgttt ttggcagcta agaatttatc agatgctatt ttactttcag atatcctaag agtaaatact gaaataacta aggctcccct atcagcttca atgattaaac gctacgatga acatcatcaa gacttgactc ttttaaaagc tttagttcga caacaacttc cagaaaagta taaagaaatc tttttgatc aatcaaaaaa cggatatgca ggttatattg atgggggagc tagccaagaa gaatttata aatttatcaa accaatttta gaaaaaatgg atggtactga ggaattattg gtgaaactaa atcgtgaaga tttgctgcgc aagcaacgga cctttgacaa cggctctatt ccccatcaaa ttcacttggg tgagctgcat
```

-continued

```
gctattttga gaagacaaga agactttat ccatttttaa aagacaatcg tgagaagatt gaaaaaatct tgacttttcg aattccttat tatgttggtc cattggcgcg tggcaatagt cgttttgcat ggatgactcg gaagtctgaa gaaacaatta ccccatggaa tttttgaagaa gttgtcgata aaggtgcttc agctcaatca tttattgaac gcatgacaaa ctttgataaa aatcttccaa atgaaaaagt actaccaaaa catagtttgc tttatgagta ttttacggtt tataacgaat tgacaaaggt caaatatgtt actgaaggaa tgcgaaaacc agcatttctt tcaggtgaac agaagaaagc cattgttgat ttactcttca aaacaaatcg aaaagtaacc gttaagcaat taaaagaaga ttatttcaaa aaaatagaat gttttgatag tgttgaaatt tcaggagttg aagatagatt taatgcttca ttaggtacct accatgattt gctaaaaatt attaaagata aagatttttt ggataatgaa gaaaatgaag atatcttaga ggatattgtt ttaacattga ccttatttga agatagggag atgattgagg aaagacttaa aacatatgct cacctctttg atgataaggt gatgaaacag cttaaacgtc gccgttatac tggttgggga cgtttgtctc gaaaattgat taatggtatt agggataagc aatctggcaa aacaatatta gatttttttga aatcagatgg ttttgccaat cgcaattta tgcagctgat ccatgatgat agtttgacat ttaaagaaga cattcaaaaa gcacaagtgt ctggacaagg cgatagttta catgaacata ttgcaaattt agctggtagc cctgctatta aaaaaggtat tttacagact gtaaaagttg ttgatgaatt ggtcaaagta atggggcggc ataagccaga aaatatcgtt attgaaatgg cacgtgaaaa tcagacaact caaaagggcc agaaaaattc gcgagagcgt atgaaacgaa tcgaagaagg tatcaaagaa ttaggaagtc agattcttaa agagcatcct gttgaaaata ctcaattgca aaatgaaaag ctctatctct attatctcca aaatggaaga gacatgtatg tggaccaaga attagatatt aatcgtttaa gtgattatga tgtcgatcac attgttccac aaagtttcct taaagacgat tcaatagaca ataaggtctt aacgcgttct gataaaaatc gtggtaaatc ggataacgtt ccaagtgaag aagtagtcaa aaagatgaaa aactattgga gacaacttct aaacgccaag ttaatcactc aacgtaagtt tgataattta acgaaagctg aacgtggagg tttgagtgaa cttgataaag ctggttttat caaacgccaa ttggttgaaa ctcgccaaat cactaagcat gtggcacaaa ttttggatag tcgcatgaat actaaatacg atgaaaatga taaacttatt cgagaggtta aagtgattac cttaaaatct aaattagttt ctgacttccg aaaagatttc caattctata aagtacgtga gattaacaat taccatcatg cccatgatgc gtatctaaat gccgtcgttg gaactgcttt gattaagaaa tatccaaaac ttgaatcgga gtttgtctat ggtgattata aagtttatga tgttcgtaaa atgattgcta agtctgagca agaaataggc aaagcaaccg caaaatattt cttttactct aatatcatga acttcttcaa aacagaaatt acacttgcaa atggagagat tcgcaaacgc cctctaatcg aaactaatgg ggaaactgga gaaattgtct gggataaagg cgcgagatttt gccacagtgc gcaaagtatt gtccatgccc caagtcaata ttgtcaagaa aacagaagta cagacaggcg gattctccaa ggagtcaatt ttaccaaaaa gaaattcgga caagcttatt gctcgtaaaa aagactggga tccaaaaaaa tatggtggtt ttgatagtcc aacggtagct tattcagtcc tagtggttgc taaggtggaa aaagggaaat cgaagaagtt aaaatccgtt aaagagttac tagggatcac aattatggaa agaagttcct ttgaaaaaaa tccgattgac ttttttagaag ctaaaggata taaggaagtt aaaaaagact taatcattaa actacctaaa tatagtcttt ttgagttaga aaacggtcgt aaacggatgc tggctagtgc cggagaatta caaaaaggaa atgagctggc tctgccaagc aaatatgtga atttttttata tttagctagt
```

-continued cattatgaaa agttgaaggg tagtccagaa gataacgaac aaaaacaatt gtttgtggag cagcataagc attatttaga tgagattatt gagcaaatca gtgaattttc taagcgtgtt attttagcag atgccaattt agataaagtt cttagtgcat ataacaaaca tagagacaaa ccaatacgtg aacaagcaga aaatattatt catttattta cgttgacgaa tcttggagct cccgctgctt ttaaatattt tgatacaaca attgatcgta aacgatatac gtctacaaaa gaagttttag atgccactct tatccatcaa tccatcactg gtctttatga aacacgcatt gatttgagtc agctaggagg tgactga (SEQ ID NO: 13)

ATGGATAAGAAATACTCAATAGGCTTAGATATCGGCACAAATAGCGTCGGATGGGCGGTGATCACTG

ATGAATATAAGGTTCCGTCTAAAAAGTTCAAGGTTCTGGGAAATACAGACCGCCACAGTATCAAAAAA

AATCTTATAGGGGCTCTTTTATTTGACAGTGGAGAGACAGCGGAAGCGACTCGTCTCAAACGGACAG

CTCGTAGAAGGTATACACGTCGGAAGAATCGTATTTGTTATCTACAGGAGATTTTTTCAAATGAGATG

GCGAAAGTAGATGATAGTTTCTTTCATCGACTTGAAGAGTCTTTTTTGGTGGAAGAAGACAAGAAGCT

GAACGTCATCCTATTTTTGGAAATATAGTAGATGAAGTTGCTTATCATGAGAAATATCCAACTATCTAC

ATCTGCGAAAAAATTGGTAGATTCTACTGATAAAGCGGATTTGCGCTTAATCTATTTGGCCTTAGCG

CATATGATTAAGTTTCGTGGTCATTTTTTGATTGAGGGAGATTTAAATCCTGATAATAGTGATGTGGAC

AAACTATTTATCCAGTTGGTACAAACCTACAATCAATTATTTGAAGAAACCCTATTAACGCAAGTGGA

GTAGATGCTAAAGCGATTCTTTCTGCACGATTGAGTAAATCAAGACGATTAGAAAATCTCATTGCTCA

GCTCCCCGGTGAGAAGAAAAATGGCTTATTTGGGAATCTCATTGCTTTGTCATTGGGTTTGACCCCTA

ATTTTAAATCAAATTTTGATTTGGCAGAAGATGCTAAATTACAGCTTTCAAAAGATACTTACGATGATG

ATTTAGATAATTTATTGGCGCAAATTGGAGATCAATATGCTGATTTGTTTTTGGCAGCTAAGAATTTAT

CAGATGCTATTTTACTTTCAGATATCCTAAGAGTAAATACTGAAATAACTAAGGCTCCCCTATCAGCTT

CAATGATTAAACGCTACGATGAACATCATCAAGACTTGACTCTTTTAAAAGCTTTAGTTCGACAACAAC

TTCCAGAAAAGTATAAAGAAATCTTTTTTGATCAATCAAAAAACGGATATGCAGGTTATATTGATGGGG

GAGCTAGCCAAGAAGAATTTTATAAATTTATCAAACCAATTTTAGAAAAAATGGATGGTACTGAGGAAT

TATTGGTGAAACTAAATCGTGAAGATTTGCTGCGCAAGCAACGGACCTTTGACAACGGCTCTATTCCC

CATCAAATTCACTTGGGTGAGCTGCATGCTATTTTGAGAAGACAAGAAGACTTTTATCCATTTTTAAAA

GACAATCGTGAGAAGATTGAAAAAATCTTGACTTTTCGAATTCCTTATTATGTTGGTCCATTGGCGCGT

GGCAATAGTCGTTTTGCATGGATGACTCGGAAGTCTGAAGAAACAATTACCCCATGGAATTTTGAAGA

AGTTGTCGATAAAGGTGCTTCAGCTCAATCATTTATTGAACGCATGACAAACTTTGATAAAAATCTTCC

AAATGAAAAAGTACTACCAAAACATAGTTTGCTTTATGAGTATTTTACGGTTTATAACGAATTGACAAA

GGTCAAATATGTTACTGAAGGAATGCGAAAACCAGCATTTCTTTCAGGTGAACAGAAGAAAGCCATTG

TTGATTTACTCTTCAAAACAAATCGAAAAGTAACCGTTAAGCAATTAAAAGAAGATTATTTCAAAAAAAT

AGAATGTTTTGATAGTGTTGAAATTTCAGGAGTTGAAGATAGATTTAATGCTTCATTAGGTACCTACCA

TGATTTGCTAAATTATTAAAGATAAAGATTTTTTGGATAATGAAGAAAATGAAGATATCTTAGAGGAT

ATTGTTTTAACATTGACCTTATTTGAAGATAGGGAGATGATTGAGGAAAGACTTAAAACATATGCTCAC

CTCTTTGATGATAAGGTGATGAAACAGCTTAAACGTCGCCGTTATACTGGTTGGGGACGTTTGTCTCG

AAAATTGATTAATGGTATTAGGGATAAGCAATCTGGCAAAACAATATTAGATTTTTTGAAATCAGATGG

TTTTGCCAATCGCAATTTTATGCAGCTGATCCATGATGATAGTTTGACATTTAAAGAAGACATTCAAAA

AGCACAAGTGTCTGGACAAGGCGATAGTTTACATGAACATATTGCAAATTTAGCTGGTAGCCCTGCTA

TTAAAAAAGGTATTTTACAGACTGTAAAAGTTGTTGATGAATTGGTCAAAGTAATGGGGCGGCATAAG

-continued

```
CCAGAAAATATCGTTATTGAAATGGCACGTGAAAATCAGACAACTCAAAAGGGCCAGAAAAATTCGC

GAGAGCGTATGAAACGAATCGAAGAAGGTATCAAAGAATTAGGAAGTCAGATTCTTAAAGAGCATCC

TGTTGAAAATACTCAATTGCAAAATGAAAAGCTCTATCTCTATTATCTCCAAAATGGAAGAGACATGTA

TGTGGACCAAGAATTAGATATTAATCGTTTAAGTGATTATGATGTCGATCACATTGTTCCACAAAGTTT

CCTTAAAGACGATTCAATAGACAATAAGGTCTTAACGCGTTCTGATAAAAATCGTGGTAAATCGGATA

ACGTTCCAAGTGAAGAAGTAGTCAAAAAGATGAAAAACTATTGGAGACAACTTCTAAACGCCAAGTTA

ATCACTCAACGTAAGTTTGATAATTTAACGAAAGCTGAACGTGGAGGTTTGAGTGAACTTGATAAAGC

TGGTTTTTATCAAACGCCAATTGGTTGAAACTCGCCAAATCACTAAGCATGTGGCACAAATTTTGGATA

GTCGCATGAATACTAAATACGATGAAAATGATAAACTTATTCGAGAGGTTAAAGTGATTACCTTAAAT

CTAAATTAGTTTCTGACTTCCGAAAAGATTTCCAATTCTATAAAGTACGTGAGATTAACAATTACCATC

ATGCCCATGATGCGTATCTAAATGCCGTCGTTGGAACTGCTTTGATTAAGAAATATCCAAAACTTGAA

TCGGAGTTTGTCTATGGTGATTATAAAGTTTATGATGTTCGTAAAATGATTGCTAAGTCTGAGCAAGAA

ATAGGCAAAGCAACCGCAAAATATTTCTTTTACTCTAATATCATGAACTTCTTCAAAACAGAAATTACA

CTTGCAAATGGAGAGATTCGCAAACGCCCTCTAATCGAAACTAATGGGGAAACTGGAGAAATTGTCT

GGGATAAAGGGCGAGATTTTGCCACAGTGCGCAAAGTATTGTCCATGCCCCAAGTCAATATTGTCAA

GAAAACAGAAGTACAGACAGGCGGATTCTCCAAGGAGTCAATTTTACCAAAAAGAAATTCGGACAAG

CTTATTGCTCGTAAAAAAGACTGGGATCCAAAAAAATATGGTGGTTTTGATAGTCCAACGGTAGCTTA

TTCAGTCCTAGTGGTTGCTAAGGTGGAAAAAGGGAAATCGAAGAAGTTAAAATCCGTTAAAGAGTTAC

TAGGGATCACAATTATGGAAAGAAGTTCCTTTGAAAAAAAATCCGATTGACTTTTTAGAAGCTAAAGGAT

ATAAGGAAGTTAAAAAAGACTTAATCATTAAACTACCTAAATATAGTCTTTTTGAGTTAGAAAACGGTC

GTAAACGGATGCTGGCTAGTGCCGGAGAATTACAAAAAGGAAATGAGCTGGCTCTGCCAAGCAAATA

TGTGAATTTTTTATATTTAGCTAGTCATTATGAAAAGTTGAAGGGTAGTCCAGAAGATAACGAACAAA

ACAATTGTTTGTGGAGCAGCATAAGCATTATTTAGATGAGATTATTGAGCAAATCAGTGAATTTTCTAA

GCGTGTTATTTTAGCAGATGCCAATTTAGATAAAGTTCTTAGTGCATATAACAAACATAGAGACAAACC

AATACGTGAACAAGCAGAAAATATTATTCATTTATTTACGTTGACGAATCTTGGAGCTCCCGCTGCTTT

TAAATATTTTGATACAACAATTGATCGTAAACGATATACGTCTACAAAAGAAGTTTTAGATGCCACTCT

ATCCATCAATCCATCACTGGTCTTTATGAAACACGCATTGATTTGAGTCAGCTAGGAGGTGACTGA.
```

Exemplary nucleases include but are not limited to those having SEQ ID NO:14 or 15, or a protein with at least 80%, 82%, 85%, 87%, 90%, 92%, 95%, 97%, 98%, 99% or 100% amino acid sequence identity to a nuclease that is encoded by SEQ ID NO:14 or 15:

```
                                   (SEQ ID NO: 14)
mkekyilgld lgitsvgygi infetkkiid agvrlfpean vdnnegrrsk rgsrrlkrrr ihrlervkll lteydlinke qiptsnnpyq irvkglseil skdelaiall hlakrrgihn invssededa snelstkeqi nrnnkllkdk yvcevqlqrt kegqirgekn rfkttdilke idqlikvqkd yhnldidfin qykeivetrr eyfegpgqgs pfgwngdlkk wyemimghct ylpqelrsvk yaysadlfna lndlnnliiq rdnsekleyh ekyhiienvf kqkkkptlkq iakeigvnpe dikgyritks
```

-continued

```
gtpqftefkl yhdlksivfd ksileneail dqiaeeiltiy qdeqsikeel nklpeilneq dkaeiaklig yngthrlslk cihlineelw qtsrnqmeif nylnikpnkv dlseqnkipk dmvndfilsp vvkrtfiqsi nvinkvieky gipediiiel arennsddrk kfinnlqkkn eatrkrinei igqtgnqnak rivekirlhd qqegkclysl esialmdlln npqnyevdhi iprsvafdns ihnkvlvkqi enskkgnrtp yqylnssdak lsynqfkqhi lnlskskdri skkkkdylle erdinkfevq kefinrnlvd tryatrelts ylkayfsann mdvkvkting sftnhlrkvw rfdkyrnhgy khhaedalii anadflfken kklqnankil ekptienntk kvtvekeedy nnvfetpklv
```

-continued

```
edikqyrdyk fshrvdkkpn rqlindtlys trmkdehdyi vqtitdiygk drtnlkkqfn knpekflmyq ndpktfekls iimkqysdek kplakyyeet geyltkyskk nngpivkkik llgnkvgnhl dvtnkyenst kklvklsikn yrfdvyltek gykfvtiayl nvfkkdnyyy ipkdkyqelk ekkkikdtdq fiasfykndl iklngdlyki igvnsddrni ieldyydiky kdyceinnik geprikktig kktesiekft tdvlgnlylh stekapqlif krgl
```

(SEQ ID NO: 15)
```
mnkpysigld igtnsvgwsi itddykvpak kmrvlgntdk eyikknliga llfdggntas drrlkrtarr rytrrrnril ylqeifaeem skvddsffhr ledsflvedd krgskypifa tmqeekdyhe kfptiyhlrk eladkkekad lrlfylalah iikfrghfli eddsfdvrnt diqrqyqafl eifdttfenn hllsqnidve giltdkisks akkdrilaqy pnqkstgifa eflklivgnq adfkkhfnle dktplqfakd sydedlenll gqigdefadl fsvakklyds vllsgiltvt distkaplsa smiqrydehr edlkqlkqfv kaslpekyqe iftdsskdgy agyiegktnq gafykylskl ltkqegseyf lekiknedfl rkqrtfdngs iphqvhltel kaiirrqsey ypflkenldr iekiltfrip yyvgplarek sdfawmtrkt ddsirpwnfe elvdkeasae afihrmtnnd lylpeekvlp khsliyekft vyneltkvry kneqgetyff dsnikqeifd gvfkehrkvs kkklldflak eyeefrivdv igldkenkaf naslgtyhdl kkildkdfld npdnesiled ivqtltlfed remikkrlen ykdlftesql kklyrrhytg wgrlsaklin girdkesqkt ildyliddgk snrnfmqlih ddglsfksii skaqagshsd nlkevvgela gspaikkgil qslkivdelv kvmgyepeqi vvemarenqt tnqgrrnsrq rykliddgvk nlasdlngni lkeyptdnqa lqnerlflyy lqngrdmytg kaldidnlsq ydidhiipqa fikddsidnr vlvssaknrg ksddvpslei vkdckvfwkk lldaklmsqr kydnltkaer ggltsddkar fiqrqlvetr qitkhvaril derfnnelds kgrrirkvki vtlksnlvsn frkefgfyki revnnyhhah daylnavvak ailtkypqle pefvygdypk ynsyktrksa teklffysni mnffktkvtl adgtvvvkdd ievnndtgei vwdkkkhfat vrkvisypqv nivkkteiqt ggfskesila hgnsdklipr ktkdiyldpk kyggfdspiv aysvlvvadi kkgkaqklkt vtellgitim ersrfeknps afleskgyln irddklmilp kyslfeleng rrrllasage lqkgnelalp tqfmkflyla srynelkgkp eeieqkqefv vqhvsyfddi lqiindfsnr
```

-continued
```
viladanlek inklyqdnke nisvdelann iinlftftsl gapaafkffd kivdrkryts tkevlnstli hqsitglyet ridlgklged.
```

Thus, in one embodiment, the ds mRNA encodes a nuclease such as a Cas9 protein e.g., one having SEQ ID NO:14 or 15, or a protein with at least 80%, 82%, 85%, 87%, 90%, 92%, 95%, 97%, 98%, 99% or 100% amino acid sequence identity to a nuclease that is encoded by SEQ ID NO:14 or 15.

Example 3

Influence of Reverse mRNA Length on Gene Expression

Figure 6:
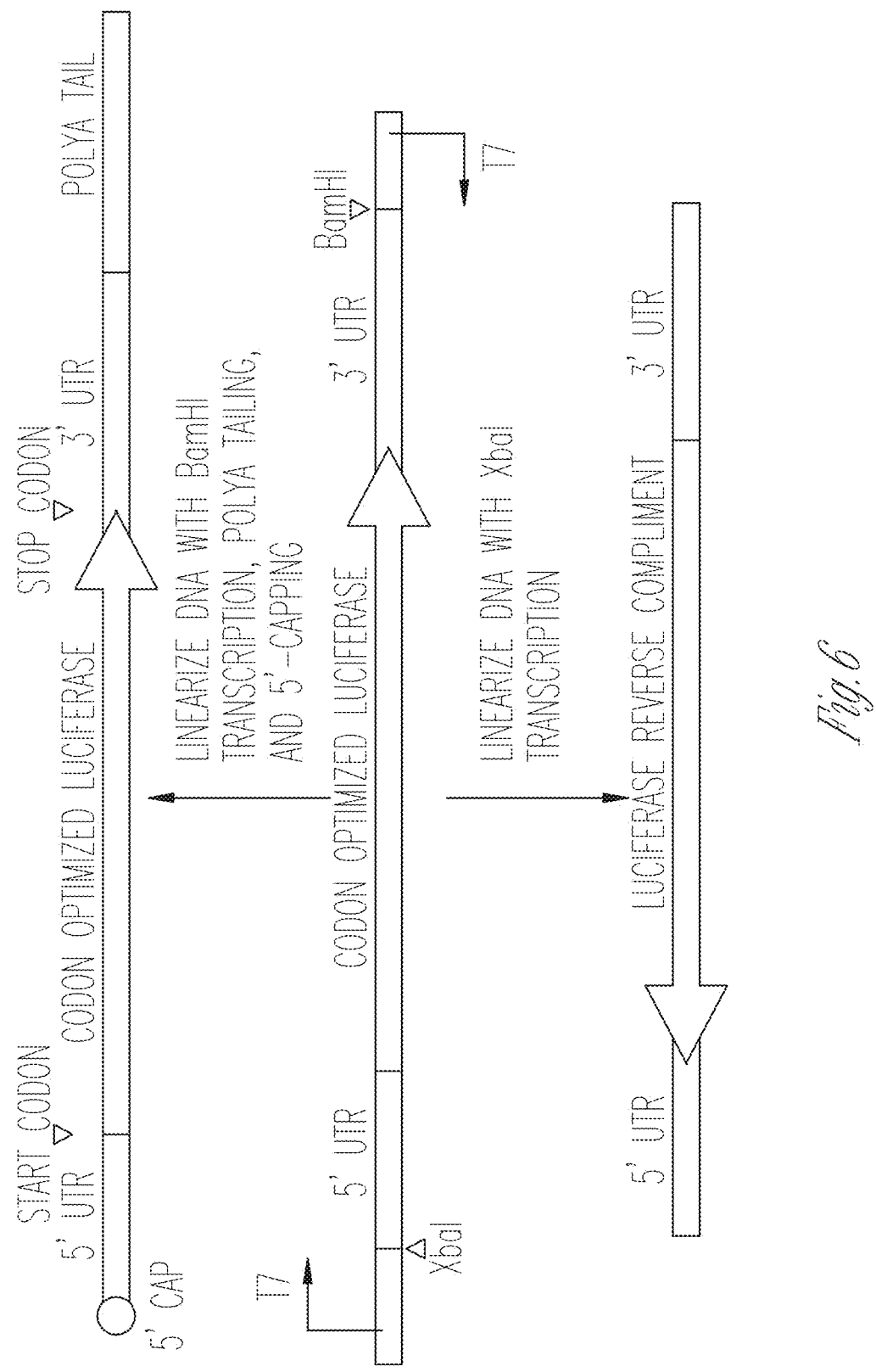
FIG. 6. Biosynthesis of ds mRNA. The preparation of forward and reverse strand mRNA is illustrated. The length or reverse mRNA controlled by the T7 transcriptional start site to the 5' transcription enzyme stop site. Xba1 was used as the full length reverse mRNA.
Figure 7:
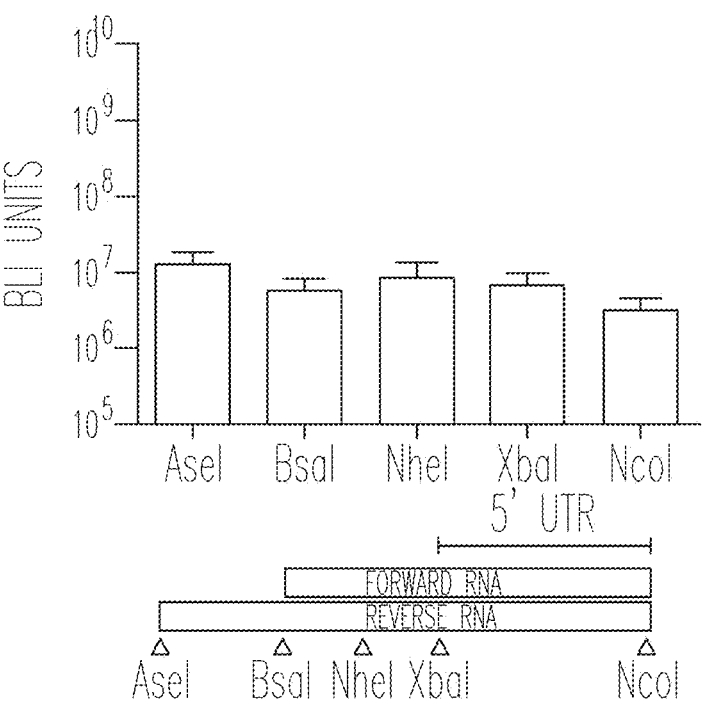
FIG. 7. Gene Expression of ds mRNA. The influence of reverse mRNA length on gene expression of ds mRNA in mice is illustrated.

The influence of the reverse strand length was analyzed by preparing reverse strand mRNA using plasmid DNA linearized with different restriction enzymes to increase or decrease the length of mRNA. XbaI was used to form the full length reverse mRNA that hybridizes with 3'UTR, coding region, and 5' UTR in forward mRNA (FIG. 6). Nhe1, Bsa1 and Ase1 were used to produce progressively longer reverse mRNA that extended beyond the 5' UTR on forward mRNA (FIG. 7). Nco1 was used to prepare a shorter reverse mRNA that hybridized with forward mRNA to expose the 5' UTR (FIG. 7). RNA transcripts (sense strand) may be "tailed" with polyA sequences after being transcribed from the vector or the vector can include sequences that result in polyA tails on transcripts obtained from the vector. Each reverse mRNA was hybridized with forward mRNA to form ds mRNA. The resulting ds mRNAs were then combined with PEG-peptide and a 1 μg dose was administered via the tail vein of triplicate mice. At five minutes post administration, mice were administered a hydrodynamic dose of 1.9 mL of saline in 5 seconds via the tall vein. After 24 hours the mice were dosed i.p. with luciferin and the level of luciferase in liver was determined by quantitative bioluminescence imaging on an IVIS image (FIG. 7). The results established that extending the length of the reverse mRNA relative to Xba1 had a negligible result on the level of gene expression (FIG. 7). Similar, decreasing the length to fully expose the 5' UTR did not significantly influence the level of gene expression (FIG. 7).

Figure 8:
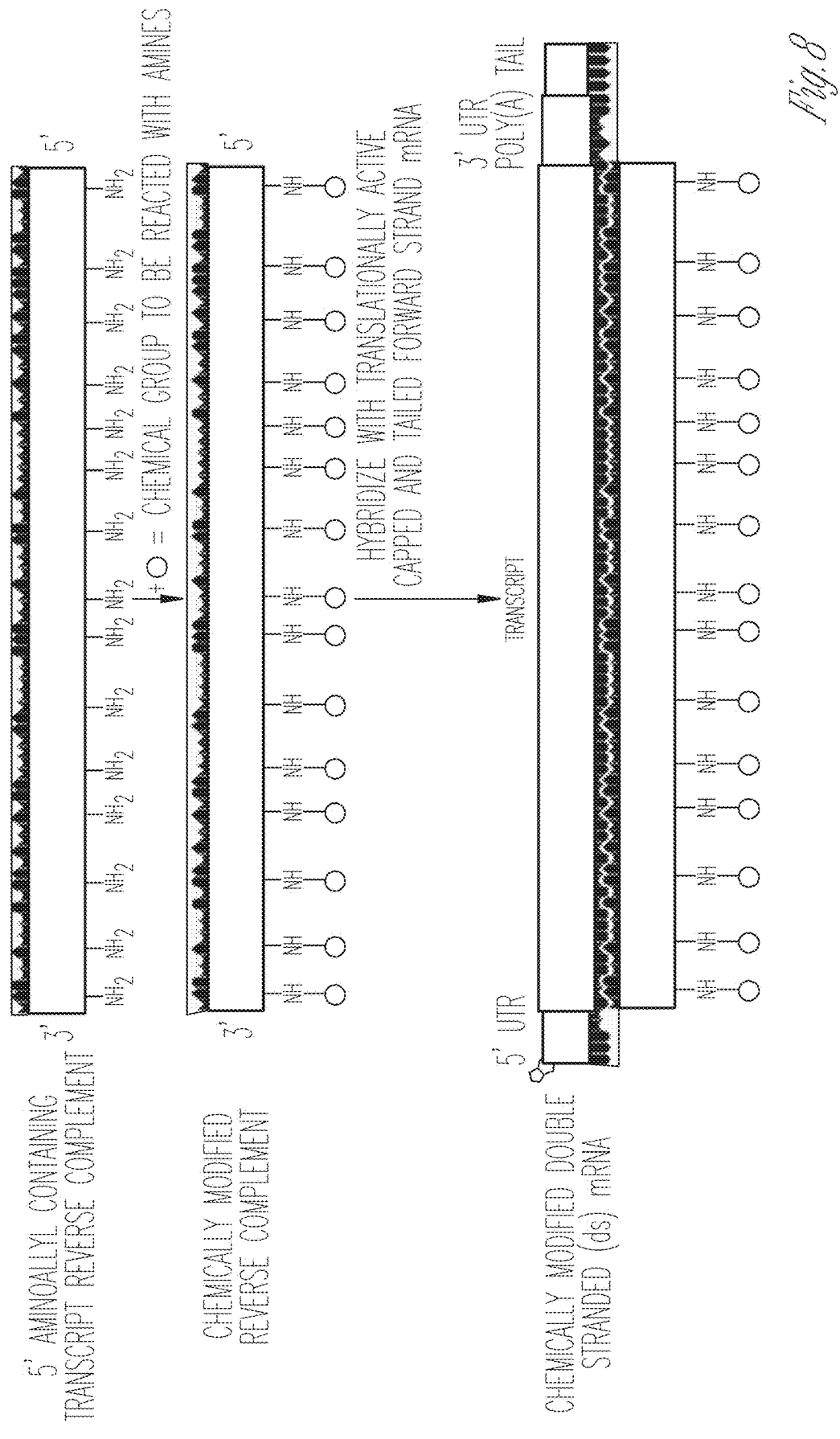
FIG. 8. Generation of Chemically modified ds mRNA.
Figure 9:
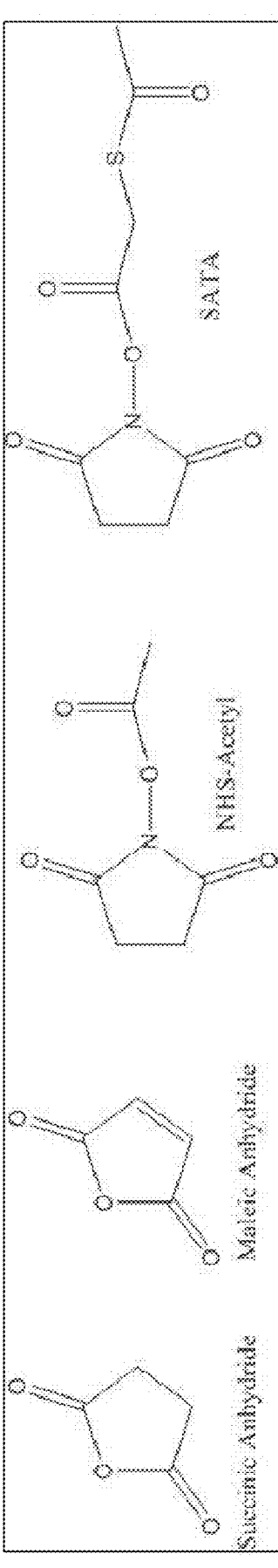
FIG. 9. Reagents Used to Chemically Modify 5' amino allyl Reverse mRNA.

Chemically modified reverse mRNA was biosynthesized using 5' amino allyl modified uridine or cytidine to replace each U or C, and both U and C, to incorporate multiple primary amines in the reverse mRNA strand (FIG. 8). Incorporation of 5'aminoallyl uridine and/or cytidine during in vitro transcription is well/tolerated, resulting in full-length (aa-U Rev-, aa-C Rev- or as-U/C Rev-) RNA with approximately 450 or 900 amines. Reverse strand primary amines May be used as a chemical handle for functionalization with acetyl, maleic acid, succinic acid, thiol-acetate, and PEG. Primary amines were then fully functionalized using anhydrides and N-hydroxysuccinamide esters to generate chemically functionalized reverse mRNA (FIG. 9).

Hybridization of chemically functionalized reverse mRNA with forward mRNA resulted in chemically modified ds mRNA. Biological testing of chemically modified ds mRNA included testing for increased metabolic stability and functional translation to express luciferase in vivo.

5' amino allyl uridine and cytidine modified ds mRNA demonstrated increased RNAse resistance relative to unmodified ds mRNA. However, 5' amino allyl modified ds mRNA was inactive when tested for translation into luciferase. Alternatively, chemical modification of reverse mRNA with the amino reactive agents in FIG. 9 resulted in ds mRNAs that were partially translationally active in expressing luciferase. The greatest translational activity resulted from modification of 5-aminoallyl uridine with acetyl.

Figure 10:
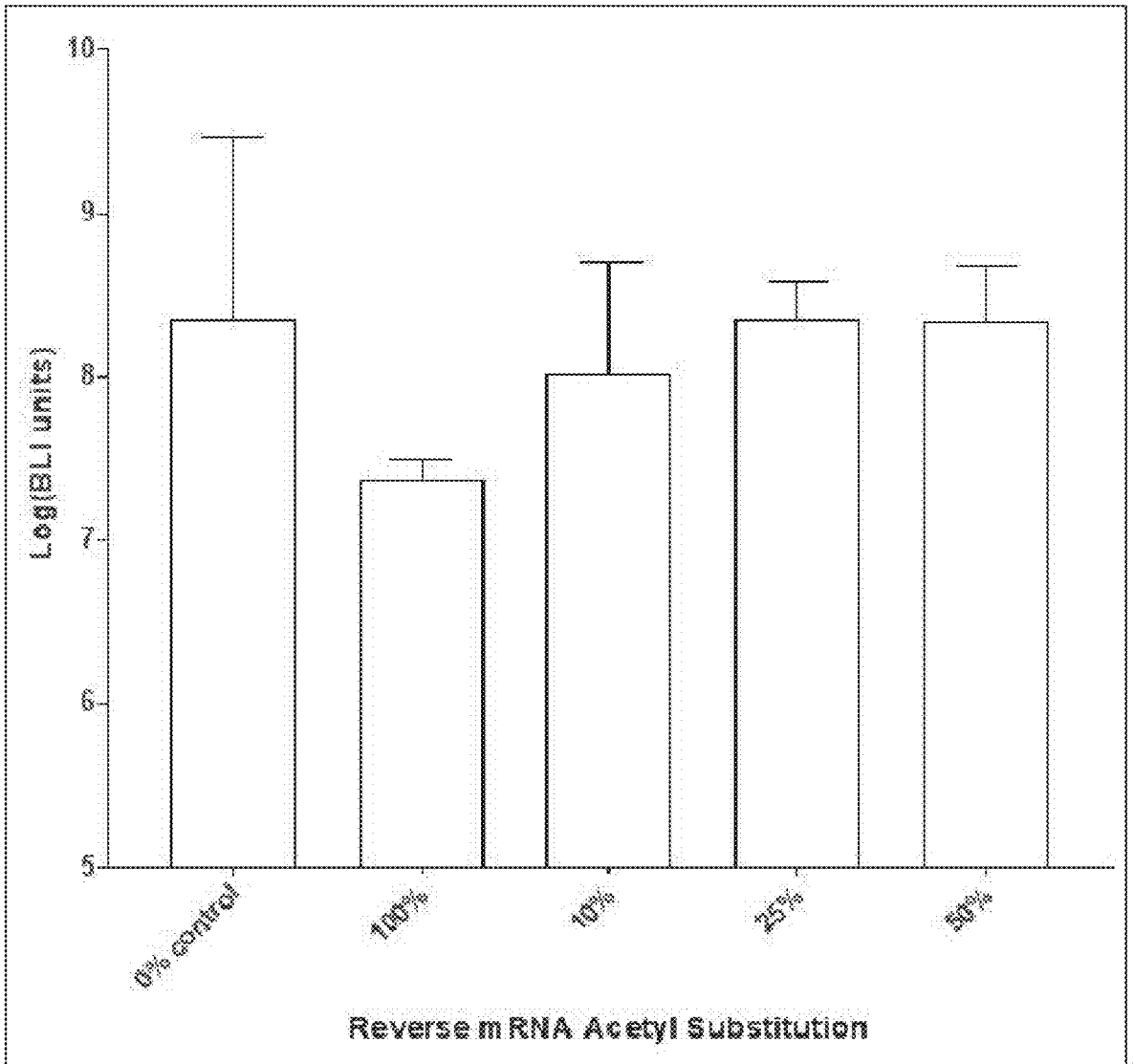
FIG. 10. In Vivo Expression of Luciferase from Chemically Modified ds mRNA. The level of luciferase expression for fully acetylated reverse mRNA with varying 5' amino allyl uridine modification is illustrated.

The magnitude of luciferase expression in liver was compared following hydrodynamic dosing of 1 μg of chemically modified ds mRNA (FIG. 10) Into the tail vein of mice. Fully acetylated 100% 5' amino allyl modified reverse mRNA resulted in a 10-fold decrease of expression relative to control. Substitution of 10-50% of reverse mRNA uridine with 5' amino allyl uridine followed by acetylation resulted in gene expression that was indistinguishable from control.

The results establish that chemical functionalization of ds mRNA can produce translationally active ds mRNA. These or further modifications may produce translationally active ds mRNA with increased metabolic stability.

REFERENCES

Al Dosari et al., Hydrodynamic Delivery, in Advances in Genetics. Academic Press. p. 65 (2005).
Andrianaivo et al., *J. Gene Med.*, 6:877 (2004).
Avci-Adali et al., *J. Biol. Eno.*, 8:8 (2014).
Cheng et al., *Biomaterials*, 33:6868 (2012).
Chuah et al., *J. Thromb. Haemost.*, 11:99 (2013).
Debus et al., *J. Control Release*, 148:334 (2010).
Deering et al., *Expert Opin. Drug Deliv.*, 11:885 (2014).
Hodges et al., *Expert Opin. Biol. Ther.*, 3:911 (2003).
Hu et al., *ACS Nano.* 7:5376 (2013).
Kariko et al., *Mol. Ther.*, 20:948 (2012).
Kormann et al., *Nat. Biotechnol.*, 29:154 (2011).

Lenter et al., *Pharmaceutical Research*, 21:683 (2004).
Liu et al., *Gene Ther.*, 6:1258 (1999).
Malone et al., *Proc. Nall. Acad. Sci. USA*, 86:6077 (1989).
McCaffrey et al., *Mol. Ther.*, 5:676 (2002).
Perche et al., *Nanomedicine*, 7:445 (2011).
Phua et al., *J. Control Release*, 166:227 (2013).
Phus et al., *Sci. Rep.*, 4:5128 (2014).
Pun et al., *Bioconjugate Chemistry*, 13:630 (2002).
Read et al., in Advances in Genetics, J. C. Hall, J. C. Dunlap, T. Friedmann, and V. van Heyningen, Editors. Academic Press. p. 19-46 (2005).
Richard et al., *Gene Ther.*, 16:746 (2009).
Sahin et al., *Nat. Rev. Drug Discov.*, 13:759 (2014).
Schlake et al., *RNA Biol.*, 9:1319 (2012).
Uchida et al., *PLoS One*, 8:e56220 (2013).
Wang et al., *Mol. Ther.*, 21:358 (2013).
Wilber et al., *Mol. Ther.*, 13:625 (2006).
Wolff et al., *Science*, 247:1465 (1990).
Wooddell et al., *Mol. Ther.*, 21:973 (2013).
Wu et al., *J. Biol. Chem.*, 263:14621 (1988).
Zangi et al., *Nat. Biotechnol.*, 31:898 (2013).
Zhang et al., *Gene Ther.*, 11:675 (2004).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention Is susceptible to additional embodiments and that certain of the details herein may be varied considerably without departing from the basic principles of the invention.

What is claimed is:

1. A method to induce an immune response in a mammal, comprising:

administering to the mammal a composition comprising a double-stranded (ds) mRNA encoding a protein, wherein the protein is an antigen, wherein the ds mRNA comprises a forward strand and a reverse strand, wherein the forward strand of the ds mRNA has a 5' cap, a start codon, a poly A sequence and encodes the protein, wherein the reverse strand comprises a 5' amino allyl modified uridine or cytidine, wherein the 5' amino allyl modified uridine or cytidine is functionalized with an anhydride, or an N-hydroxysuccinamide ester, wherein the two strands of the ds mRNA are hydrogen bonded over at least 50% of the length of the strands, wherein the hydrogen bonded strands include at least a portion of the coding region for the protein;

wherein following administration of the composition to the mammal, the mammal expresses the protein, and wherein the protein induces an immune response in the mammal;

wherein the composition further comprises a carrier protein or a synthetic polymer.

2. The method of claim 1, wherein the protein is a cancer antigen.

3. The method of claim 1, wherein the composition is systemically administered to the mammal.

4. The method of claim 1, wherein the composition further comprises a liposome or a nanoparticle.

5. The method of claim 1, wherein at least one strand includes one or more non-natural nucleotides.

6. The method of claim 5, wherein at least one of the non-natural nucleotides has a non-natural sugar or a non-natural nucleobase, or a combination thereof.

7. The method of claim 5, wherein at least 5% of the nucleotides are non-natural nucleotides.

8. The method of claim 5, wherein the non-natural nucleotide is a purine analog.

9. The method of claim 1, wherein at least one strand includes at least one non-phosphodiester bond.

10. The method of claim 1, wherein at least one strand includes 5-formyl cytidine or pseudouridine.

11. The method of claim 1, wherein one of the strands is no more than 5 kb in length.

12. The method of claim 1, wherein at least one strand has two or more different non-natural nucleotides.

13. The method of claim 1, wherein the strands are not the same length.

14. The method of claim 1, wherein the composition is administered intramuscularly (IM).

15. The method of claim 1, wherein the protein is a viral antigen.

16. The method of claim 1, wherein the protein is a bacterial antigen.

*   *   *   *   *